(12) United States Patent
Chen

(10) Patent No.: US 10,391,148 B2
(45) Date of Patent: Aug. 27, 2019

(54) METHOD OF PREVENTION AND INHIBITION OF PRETERM LABOR

(71) Applicant: Wayne State University, Detroit, MI (US)

(72) Inventor: Kang Chen, Detroit, MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 15/692,517

(22) Filed: Aug. 31, 2017

(65) Prior Publication Data

US 2018/0055910 A1  Mar. 1, 2018

Related U.S. Application Data

(60) Provisional application No. 62/381,964, filed on Aug. 31, 2016.

(51) Int. Cl.
*A61K 38/17* (2006.01)
*A61K 38/20* (2006.01)
*A61K 45/06* (2006.01)

(52) U.S. Cl.
CPC .......... *A61K 38/20* (2013.01); *A61K 38/1709* (2013.01); *A61K 45/06* (2013.01)

(58) Field of Classification Search
None
See application file for complete search history.

(56) References Cited

U.S. PATENT DOCUMENTS 9,840,545 B2 * 12/2017 Sharma ................. C07K 14/54

OTHER PUBLICATIONS

Par et al., Am J Obstet Gynecol. Jul. 2000;183(1):126-130 (Year: 2000).*

* cited by examiner

*Primary Examiner* — Daniel C Gamett
(74) *Attorney, Agent, or Firm* — Julie K. Staple; Dinsmore & Shohl LLP

(57) ABSTRACT

Methods for preventing and/or inhibiting preterm labor in a pregnant subject, such as a human subject, are disclosed according to the invention including administering a therapeutically effective amount of a protein selected from the group consisting of: PIBF1, a fragment or variant thereof; IL-33, a fragment or variant thereof; and a combination of any two or more thereof. Pharmaceutical compositions for preventing and/or inhibiting preterm labor in a pregnant subject, such as a human subject, are disclosed according to the invention including a therapeutically effective amount of a protein selected from the group consisting of: PIBF1, a fragment or variant thereof; IL-33, a fragment or variant thereof; and a combination of any two or more thereof.

12 Claims, 35 Drawing Sheets

Specification includes a Sequence Listing.

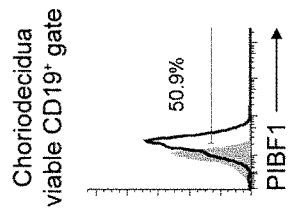
FIG. 3F
FIG. 3G
FIG. 3H

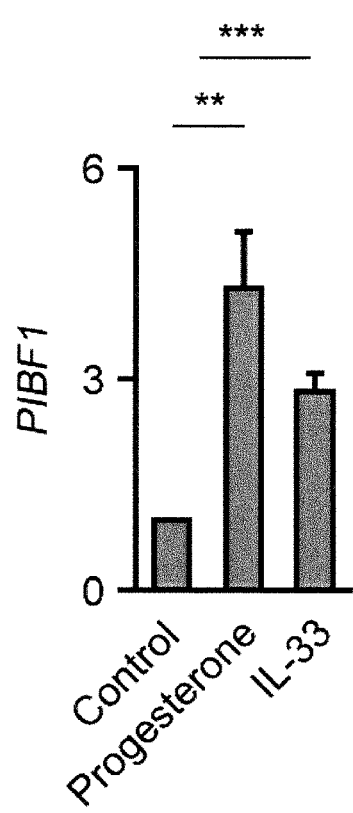
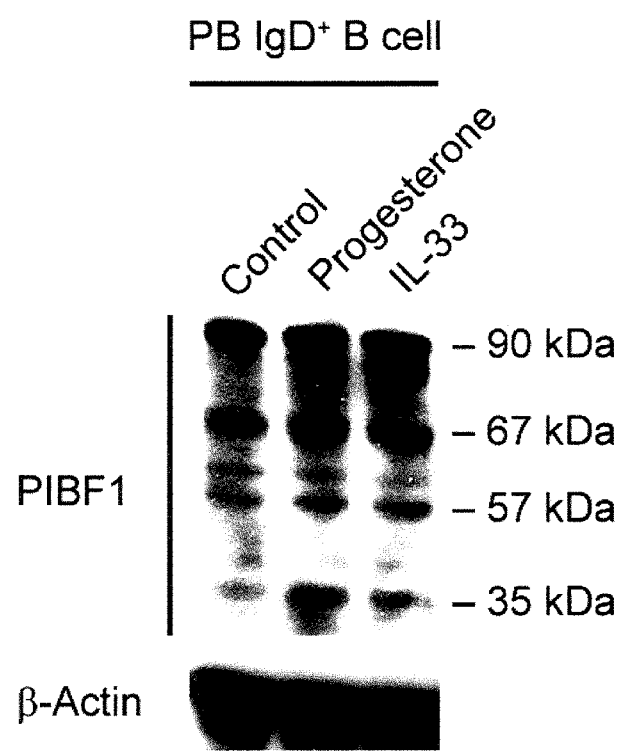
FIG. 4A
FIG. 4B

SEQUENCE LISTING

<160> NUMBER OF SEQ ID NOS: 54

<210> SEQ ID NO 1
<211> LENGTH: 757
<212> TYPE: PRT
<213> ORGANISM: Homo sapiens

<400> SEQUENCE: 1

Met Ser Arg Lys Ile Ser Lys Glu Ser Lys Val Asn Ile Ser Ser
1               5                   10                  15

Ser Leu Glu Ser Glu Asp Ile Ser Leu Glu Thr Thr Val Pro Thr Asp
            20                  25                  30

Asp Ile Ser Ser Ser Glu Glu Arg Glu Gly Lys Val Arg Ile Thr Arg
            35                  40                  45

Gln Leu Ile Glu Arg Lys Glu Leu Leu His Asn Ile Gln Leu Leu Lys
        50                  55                  60

Ile Glu Leu Ser Gln Lys Thr Met Met Ile Asp Asn Leu Lys Val Asp
65                  70                  75                  80

Tyr Leu Thr Lys Ile Glu Glu Leu Glu Glu Lys Leu Asn Asp Ala Leu
                85                  90                  95

His Gln Lys Gln Leu Leu Thr Leu Arg Leu Asp Asn Gln Leu Ala Phe
            100                 105                 110

Gln Gln Lys Asp Ala Ser Lys Tyr Gln Glu Leu Met Lys Gln Glu Met
            115                 120                 125

Glu Thr Ile Leu Leu Arg Gln Lys Gln Leu Glu Glu Thr Asn Leu Gln
            130                 135                 140

Leu Arg Glu Lys Ala Gly Asp Val Arg Arg Asn Leu Arg Asp Phe Glu
145                 150                 155                 160

Leu Thr Glu Glu Gln Tyr Ile Lys Leu Lys Ala Phe Pro Glu Asp Gln
                165                 170                 175

Leu Ser Ile Pro Glu Tyr Val Ser Val Arg Phe Tyr Glu Leu Val Asn
            180                 185                 190

Pro Leu Arg Lys Glu Ile Cys Glu Leu Gln Val Lys Lys Asn Ile Leu
            195                 200                 205

Ala Glu Glu Leu Ser Thr Asn Lys Asn Gln Leu Lys Gln Leu Thr Glu
        210                 215                 220

Thr Tyr Glu Glu Asp Arg Lys Asn Tyr Ser Glu Val Gln Ile Arg Cys
225                 230                 235                 240

Gln Arg Leu Ala Leu Glu Leu Ala Asp Thr Lys Gln Leu Ile Gln Gln
                245                 250                 255

Gly Asp Tyr Arg Gln Glu Asn Tyr Asp Lys Val Lys Ser Glu Arg Asp
            260                 265                 270

Ala Leu Glu Gln Glu Val Ile Glu Leu Arg Arg Lys His Glu Ile Leu
            275                 280                 285

Glu Ala Ser His Met Ile Gln Thr Lys Glu Arg Ser Glu Leu Ser Lys
        290                 295                 300

Glu Val Val Thr Leu Glu Gln Thr Val Thr Leu Leu Gln Lys Asp Lys
305                 310                 315                 320

Glu Tyr Leu Asn Arg Gln Asn Met Glu Leu Ser Val Arg Cys Ala His
                325                 330                 335

Glu Glu Asp Arg Leu Glu Arg Leu Gln Ala Gln Leu Glu Glu Ser Lys
            340                 345                 350

Lys Ala Arg Glu Glu Met Tyr Glu Lys Tyr Val Ala Ser Arg Asp His
            355                 360                 365

Tyr Lys Thr Glu Tyr Glu Asn Lys Leu His Asp Glu Leu Glu Gln Ile
    370                 375                 380

Arg Leu Lys Thr Asn Gln Glu Ile Asp Gln Leu Arg Asn Ala Ser Arg
385                 390                 395                 400

Glu Met Tyr Glu Arg Glu Asn Arg Asn Leu Arg Glu Ala Arg Asp Asn
                405                 410                 415

Ala Val Ala Glu Lys Glu Arg Ala Val Met Ala Glu Lys Asp Ala Leu
            420                 425                 430

Glu Lys His Asp Gln Leu Leu Asp Arg Tyr Arg Glu Leu Gln Leu Ser
        435                 440                 445

Thr Glu Ser Lys Val Thr Glu Phe Leu His Gln Ser Lys Leu Lys Ser
    450                 455                 460

Phe Glu Ser Glu Arg Val Gln Leu Leu Gln Glu Thr Ala Arg Asn
465                 470                 475                 480

Leu Thr Gln Cys Gln Leu Glu Cys Glu Lys Tyr Gln Lys Lys Leu Glu
                485                 490                 495

Val Leu Thr Lys Glu Phe Tyr Ser Leu Gln Ala Ser Ser Glu Lys Arg
            500                 505                 510

Ile Thr Glu Leu Gln Ala Gln Asn Ser Glu His Gln Ala Arg Leu Asp
        515                 520                 525

Ile Tyr Glu Lys Leu Glu Lys Glu Leu Asp Glu Ile Met Gln Thr
    530                 535                 540

Ala Glu Ile Glu Asn Glu Asp Glu Ala Glu Arg Val Leu Phe Ser Tyr
545                 550                 555                 560

Gly Tyr Gly Ala Asn Val Pro Thr Thr Ala Lys Arg Arg Leu Lys Gln
                565                 570                 575

Ser Val His Leu Ala Arg Arg Val Leu Gln Leu Glu Lys Gln Asn Ser
            580                 585                 590

Leu Ile Leu Lys Asp Leu Glu His Arg Lys Asp Gln Val Thr Gln Leu
        595                 600                 605

Ser Gln Glu Leu Asp Arg Ala Asn Ser Leu Leu Asn Gln Thr Gln Gln
    610                 615                 620

Pro Tyr Arg Tyr Leu Ile Glu Ser Val Arg Gln Arg Asp Ser Lys Ile
625                 630                 635                 640

Asp Ser Leu Thr Glu Ser Ile Ala Gln Leu Glu Lys Asp Val Ser Asn
                645                 650                 655

Leu Asn Lys Glu Lys Ser Ala Leu Leu Gln Thr Lys Asn Gln Met Ala
            660                 665                 670

Leu Asp Leu Glu Gln Leu Leu Asn His Arg Glu Glu Leu Ala Ala Met
        675                 680                 685

Lys Gln Ile Leu Val Lys Met His Ser Lys His Ser Glu Asn Ser Leu
    690                 695                 700

Leu Leu Thr Lys Thr Glu Pro Lys His Val Thr Glu Asn Gln Lys Ser
705                 710                 715                 720

Lys Thr Leu Asn Val Pro Lys Glu His Glu Asp Asn Ile Phe Thr Pro
                725                 730                 735

Lys Pro Thr Leu Phe Thr Lys Lys Glu Ala Pro Glu Trp Ser Lys Lys
            740                 745                 750

Gln Lys Met Lys Thr
        755

<210> SEQ ID NO 2
<211> LENGTH: 659
<212> TYPE: PRT

<213> ORGANISM: Homo sapiens

<400> SEQUENCE: 2

```
Met Ser Arg Lys Ile Ser Lys Glu Ser Lys Val Asn Ile Ser Ser
1               5                   10                  15

Ser Leu Glu Ser Glu Asp Ile Ser Leu Glu Thr Thr Val Pro Thr Asp
            20                  25                  30

Asp Ile Ser Ser Ser Glu Glu Arg Glu Gly Lys Val Arg Ile Thr Arg
                35                  40                  45

Gln Leu Ile Glu Arg Lys Glu Leu Leu His Asn Ile Gln Leu Leu Lys
    50                  55                  60

Ile Glu Leu Ser Gln Lys Thr Met Met Ile Asp Asn Leu Lys Val Asp
65                  70                  75                  80

Tyr Leu Thr Lys Ile Glu Glu Leu Glu Glu Lys Leu Asn Asp Ala Leu
                85                  90                  95

His Gln Lys Gln Leu Leu Thr Leu Arg Leu Asp Asn Gln Leu Ala Phe
            100                 105                 110

Gln Gln Lys Asp Ala Ser Lys Tyr Gln Glu Leu Met Lys Gln Glu Met
        115                 120                 125

Glu Thr Ile Leu Leu Arg Gln Lys Gln Leu Glu Glu Thr Asn Leu Gln
130                 135                 140

Leu Arg Glu Lys Ala Gly Asp Val Arg Arg Asn Leu Arg Asp Phe Glu
145                 150                 155                 160

Leu Thr Glu Glu Gln Tyr Ile Lys Leu Lys Ala Phe Pro Glu Asp Gln
                165                 170                 175

Leu Ser Ile Pro Glu Tyr Val Ser Val Arg Phe Tyr Glu Leu Val Asn
            180                 185                 190

Pro Leu Arg Lys Glu Ile Cys Glu Leu Gln Val Lys Lys Asn Ile Leu
        195                 200                 205

Ala Glu Glu Leu Ser Thr Asn Lys Asn Gln Leu Lys Gln Leu Thr Glu
210                 215                 220

Thr Tyr Glu Glu Asp Arg Lys Asn Tyr Ser Glu Val Gln Ile Arg Cys
225                 230                 235                 240

Gln Arg Leu Ala Leu Glu Leu Ala Asp Thr Lys Gln Leu Ile Gln Gln
                245                 250                 255

Gly Asp Tyr Arg Gln Glu Asn Tyr Asp Lys Val Lys Ser Glu Arg Asp
            260                 265                 270

Ala Leu Glu Gln Glu Val Ile Glu Leu Arg Arg Lys His Glu Ile Leu
        275                 280                 285

Glu Ala Ser His Met Ile Gln Thr Lys Glu Arg Ser Glu Leu Ser Lys
290                 295                 300

Glu Val Val Thr Leu Glu Gln Thr Val Thr Leu Leu Gln Lys Asp Lys
305                 310                 315                 320

Glu Tyr Leu Asn Arg Gln Asn Met Glu Leu Ser Val Arg Cys Ala His
                325                 330                 335

Glu Glu Asp Arg Leu Glu Arg Leu Gln Ala Gln Leu Glu Glu Ser Lys
            340                 345                 350

Lys Ala Arg Glu Glu Met Tyr Glu Lys Tyr Val Ala Ser Arg Asp His
        355                 360                 365

Tyr Lys Thr Glu Tyr Glu Asn Lys Leu His Asp Glu Leu Glu Gln Ile
370                 375                 380

Arg Leu Lys Thr Asn Gln Glu Ile Asp Gln Leu Arg Asn Ala Ser Arg
385                 390                 395                 400
```

```
Glu Met Tyr Glu Arg Glu Asn Arg Asn Leu Arg Ala Arg Asp Asn
                405                 410                 415
Ala Val Ala Glu Lys Arg Ala Val Met Ala Glu Lys Asp Ala Leu
            420                 425                 430
Glu Lys His Asp Gln Leu Leu Asp Arg Tyr Arg Glu Leu Gln Leu Ser
        435                 440                 445
Thr Glu Ser Lys Val Thr Glu Phe Leu His Gln Ser Lys Leu Lys Ser
    450                 455                 460
Phe Glu Ser Glu Arg Val Gln Leu Leu Gln Glu Thr Ala Arg Asn
465                 470                 475                 480
Leu Thr Gln Cys Gln Leu Glu Cys Glu Lys Tyr Gln Lys Leu Glu
                485                 490                 495
Val Leu Thr Lys Glu Phe Tyr Ser Leu Gln Ala Ser Ser Glu Lys Arg
            500                 505                 510
Ile Thr Glu Leu Gln Ala Gln Asn Ser Glu His Gln Ala Arg Leu Asp
        515                 520                 525
Ile Tyr Glu Lys Leu Glu Lys Glu Leu Asp Glu Ile Ile Met Gln Thr
    530                 535                 540
Ala Glu Ile Glu Asn Glu Asp Glu Ala Glu Arg Val Leu Phe Ser Tyr
545                 550                 555                 560
Gly Tyr Gly Ala Asn Val Pro Thr Thr Ala Lys Arg Arg Leu Lys Gln
                565                 570                 575
Ser Val His Leu Ala Arg Arg Val Leu Gln Leu Glu Lys Gln Asn Ser
            580                 585                 590
Leu Ile Leu Lys Asp Leu Glu His Arg Lys Asp Gln Val Thr Gln Leu
        595                 600                 605
Ser Gln Glu Leu Asp Arg Ala Asn Ser Leu Leu Asn Gln Thr Gln Gln
    610                 615                 620
Pro Tyr Arg Tyr Leu Ile Glu Ser Val Arg Gln Arg Asp Ser Lys Ile
625                 630                 635                 640
Asp Ser Leu Thr Glu Ser Ile Ala Gln Leu Glu Lys Asp Val Ser Asn
                645                 650                 655
Leu Asn Lys

<210> SEQ ID NO 3
<211> LENGTH: 2274
<212> TYPE: DNA
<213> ORGANISM: Homo sapiens

<400> SEQUENCE: 3
atgtctcgaa aaatttcaaa ggagtcaaaa aaagtgaaca tctctagttc tctggaatct      60
gaagatatta gtttagaaac aacagttcct acgatgata  tttcctcatc agaagagcga     120
gagggcaaag tcagaatcac caggcagcta attgaacgaa agaactact  tcataatatt     180 cagttactaa aaattgagct atcccagaaa actatgatga tcgacaattt gaaagtggat     240
tatcttacaa agattgaaga attggaggag aaacttaatg atgcacttca ccagaagcag     300
ctactaacat tgagattaga caaccaattg gcttttcaac agaaagatgc cagcaaatat     360
caagaattaa tgaaacaaga atggaaacc attttgttga cagaaaaca  actagaagag     420 acaaatcttc agctaagaga aaaagctgga gatgttcgtc gaaacctgcg tgactttgag     480
ttgacagaag agcaatatat taaattaaaa gcttttcctg aagatcagct ttctattcct     540
gaatatgtat ctgttcgctt ctatgagcta gtgaatccat taagaaagga aatctgtgaa     600
ctacaagtga aaaagaatat cctagcagaa gaattaagta caaacaaaaa ccaactgaag     660
```

```
cagctgacag agacatatga ggaagatcga aaaaactact ctgaagttca aattagatgt    720
caacgtttgg ccttagaatt agcagacaca aaacagttaa ttcagcaagg tgactaccgt    780
caagagaact atgataaagt caagagtgaa cgtgatgcac ttgaacagga agtaattgag    840
cttaggagaa acatgaaat acttgaagcc tctcacatga ttcaaacaaa agaacgaagt    900
gaattatcaa agaggtagt caccttagag caaactgtta ctttactgca aaaggataaa    960
gaatatctta atcgccaaaa catggagctt agtgttcgct gtgctcatga agaggatcgc   1020
cttgaaagac ttcaagctca actggaagaa agcaaaaagg ctagagaaga gatgtatgaa   1080
aaatatgtag catccagaga ccattataaa acagaatatg aaaataaact acatgatgaa   1140
ctagaacaaa tcagattgaa aaccaaccaa gaaattgatc aacttcgaaa tgcctctagg   1200
gaaatgtatg aacgagaaaa cagaaatctc cgagaagcaa gggataatgc tgtggctgaa   1260
aaggaacgag cagtgatggc tgaaaaggat gctttagaaa aacacgatca gctcttagac   1320
aggtacagag aactacaact tagtacagaa agcaaagtaa cagaatttct ccatcaaagt   1380
aaattaaaat cttttgaaag tgagcgtgtt caacttctgc aagaggaaac agcaagaaat   1440
ctcacacagt gtcaattgga atgtgaaaaa tatcagaaaa aattggaggt tttaaccaaa   1500
gaattttata gtctccaagc ctcttctgaa aaacgcatta ctgaacttca agcacagaac   1560
tcagagcatc aagcaaggct agacatttat gagaaactgg aaaagagct tgatgaaata   1620 ataatgcaaa ctgcagaaat tgaaaatgaa gatgaggctg aaagggttct tttttcctac   1680
ggctatggtg ctaatgttcc cacaacagcc aaaagacgac taaagcaaag tgttcacttg   1740
gcaagaagag tgcttcaatt agaaaaacaa aactcgctga ttttaaaaga tctggaacat   1800
cgaaaggacc aagtaacaca gctttcacaa gagcttgaca gagccaattc gctattaaac   1860
cagactcaac agccttacag gtatctcatt gaatcagtgc gtcagagaga ttctaagatt   1920
gattcactga cggaatctat tgcacaactt gagaaagatg tcagcaactt aaataaagaa   1980
aagtcagctt tactacagac gaagaatcaa atggcattag atttagaaca acttctaaat   2040
catcgtgagg aattggcagc aatgaaacag attctcgtta agatgcatag taaacattct   2100
gagaacagct tacttctcac taaaacagaa ccaaaacatg tgcagaaaaa tcagaaatca   2160
aagactttga atgtgcctaa agagcatgaa gacaatatat ttacacctaa accaacactc   2220
tttactaaaa aagaagcacc tgagtggtct aagaaacaaa agatgaagac ctag          2274
```

<210> SEQ ID NO 4
<211> LENGTH: 1977
<212> TYPE: DNA
<213> ORGANISM: Homo sapiens

<400> SEQUENCE: 4

```
atgtctcgaa aaatttcaaa ggagtcaaaa aaagtgaaca tctctagttc tctggaatct     60
gaagatatta gttagaaaac aacagttcct acgatgata tttcctcatc agaagagcga    120
gagggcaaag tcagaatcac caggcagcta attgaacgaa agaactact tcataatatt    180 cagttactaa aaattgagct atcccagaaa actatgatga tcgacaattt gaaagtggat    240
tatcttacaa agattgaaga attggaggag aaacttaatg atgcacttca ccagaagcag    300
ctactaacat tgagattaga caaccaattg cttttcaac agaaagatgc cagcaaatat    360
caagaattaa tgaaacaaga aatggaaacc attttgttga cagaaaca actagaagag    420 acaaatcttc agctaagaga aaaagctgga gatgttcgtc gaaacctgcg tgactttgag    480
```

```
ttgacagaag agcaatatat taaattaaaa gcttttcctg aagatcagct ttctattcct    540
gaatatgtat ctgttcgctt ctatgagcta gtgaatccat taagaaagga aatctgtgaa    600
ctacaagtga aaagaatat cctagcagaa gaattaagta caaacaaaaa ccaactgaag     660
cagctgacag agacatatga ggaagatcga aaaaactact ctgaagttca aattagatgt    720
caacgtttgg ccttagaatt agcagacaca aaacagttaa ttcagcaagg tgactaccgt    780
caagagaact atgataaagt caagagtgaa cgtgatgcac ttgaacagga agtaattgag    840
cttaggagaa acatgaaat acttgaagcc tctcacatga ttcaaacaaa agaacgaagt     900
gaattatcaa aagaggtagt caccttagag caaactgtta ctttactgca aaaggataaa    960
gaatatctta atcgccaaaa catggagctt agtgttcgct gtgctcatga agaggatcgc   1020
cttgaaagac ttcaagctca actggaagaa agcaaaaagg ctagagaaga gatgtatgaa   1080
aaatatgtag catccagaga ccattataaa acagaatatg aaaataaact acatgatgaa   1140
ctagaacaaa tcagattgaa aaccaaccaa gaaattgatc aacttcgaaa tgcctctagg   1200
gaaatgtatg aacgagaaaa cagaaatctc cgagaagcaa gggataatgc tgtggctgaa   1260
aaggaacgag cagtgatggc tgaaaaggat gctttagaaa acacgatca gctcttagac    1320
aggtacagag aactacaact tagtacagaa agcaaagtaa cagaatttct ccatcaaagt   1380
aaattaaaat cttttgaaag tgagcgtgtt caacttctgc aagaggaaac agcaagaaat   1440
ctcacacagt gtcaattgga atgtgaaaaa tatcagaaaa aattggaggt ttaaccaaa    1500
gaattttata gtctccaagc ctcttctgaa aaacgcatta ctgaacttca agcacagaac   1560
tcagagcatc aagcaaggct agacatttat gagaaactgg aaaagagct tgatgaaata    1620
ataatgcaaa ctgcagaaat tgaaaatgaa gatgaggctg aaagggttct tttttcctac   1680
ggctatggtg ctaatgttcc cacaacagcc aaaagacgac taaagcaaag tgttcacttg   1740
gcaagaagag tgcttcaatt agaaaaacaa aactcgctga ttttaaaaga tctggaacat   1800
cgaaaggacc aagtaacaca gctttcacaa gagcttgaca gagccaattc gctattaaac   1860
cagactcaac agccttacag gtatctcatt gaatcagtgc gtcagagaga ttctaagatt   1920
gattcactga cggaatctat tgcacaactt gagaaagatg tcagcaactt aaataaa     1977
```

<210> SEQ ID NO 5
<211> LENGTH: 270
<212> TYPE: PRT
<213> ORGANISM: Homo sapiens

<400> SEQUENCE: 5

```
Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Lys Ser
            20                  25                  30

Gln Gln Lys Ala Lys Glu Val Cys Pro Met Tyr Phe Met Lys Leu Arg
        35                  40                  45

Ser Gly Leu Met Ile Lys Lys Glu Ala Cys Tyr Phe Arg Arg Glu Thr
    50                  55                  60

Thr Lys Arg Pro Ser Leu Lys Thr Gly Arg Lys His Lys Arg His Leu
65                  70                  75                  80

Val Leu Ala Ala Cys Gln Gln Gln Ser Thr Val Glu Cys Phe Ala Phe
                85                  90                  95

Gly Ile Ser Gly Val Gln Lys Tyr Thr Arg Ala Leu His Asp Ser Ser
            100                 105                 110
```

```
Ile Thr Gly Ile Ser Pro Ile Thr Glu Tyr Leu Ala Ser Leu Ser Thr
        115                 120                 125

Tyr Asn Asp Gln Ser Ile Thr Phe Ala Leu Glu Asp Glu Ser Tyr Glu
130                 135                 140

Ile Tyr Val Glu Asp Leu Lys Lys Asp Glu Lys Lys Asp Lys Val Leu
145                 150                 155                 160

Leu Ser Tyr Tyr Glu Ser Gln His Pro Ser Asn Glu Ser Gly Asp Gly
                165                 170                 175

Val Asp Gly Lys Met Leu Met Val Thr Leu Ser Pro Thr Lys Asp Phe
            180                 185                 190

Trp Leu His Ala Asn Asn Lys Glu His Ser Val Glu Leu His Lys Cys
        195                 200                 205

Glu Lys Pro Leu Pro Asp Gln Ala Phe Phe Val Leu His Asn Met His
    210                 215                 220

Ser Asn Cys Val Ser Phe Glu Cys Lys Thr Asp Pro Gly Val Phe Ile
225                 230                 235                 240

Gly Val Lys Asp Asn His Leu Ala Leu Ile Lys Val Asp Ser Ser Glu
                245                 250                 255

Asn Leu Cys Thr Glu Asn Ile Leu Phe Lys Leu Ser Glu Thr
            260                 265                 270

<210> SEQ ID NO 6
<211> LENGTH: 266
<212> TYPE: PRT
<213> ORGANISM: Homo sapiens

<400> SEQUENCE: 6

Met Arg Pro Arg Met Lys Tyr Ser Asn Ser Lys Ile Ser Pro Ala Lys
1               5                   10                  15

Phe Ser Ser Thr Ala Gly Glu Ala Leu Val Pro Pro Cys Lys Ile Arg
            20                  25                  30

Arg Ser Gln Gln Lys Thr Lys Glu Phe Cys His Val Tyr Cys Met Arg
        35                  40                  45

Leu Arg Ser Gly Leu Thr Ile Arg Lys Glu Thr Ser Tyr Phe Arg Lys
50                  55                  60

Glu Pro Thr Lys Arg Tyr Ser Leu Lys Ser Gly Thr Lys His Glu Glu
65                  70                  75                  80

Asn Phe Ser Ala Tyr Pro Arg Asp Ser Arg Lys Arg Ser Leu Leu Gly
                85                  90                  95

Ser Ile Gln Ala Phe Ala Ala Ser Val Asp Thr Leu Ser Ile Gln Gly
            100                 105                 110

Thr Ser Leu Leu Thr Gln Ser Pro Ala Ser Leu Ser Thr Tyr Asn Asp
        115                 120                 125

Gln Ser Val Ser Phe Val Leu Glu Asn Gly Cys Tyr Val Ile Asn Val
    130                 135                 140

Asp Asp Ser Gly Lys Asp Gln Glu Gln Asp Gln Val Leu Leu Arg Tyr
145                 150                 155                 160

Tyr Glu Ser Pro Cys Pro Ala Ser Gln Ser Gly Asp Gly Val Asp Gly
                165                 170                 175

Lys Lys Leu Met Val Asn Met Ser Pro Ile Lys Asp Thr Asp Ile Trp
            180                 185                 190

Leu His Ala Asn Asp Lys Asp Tyr Ser Val Glu Leu Gln Arg Gly Asp
        195                 200                 205

Val Ser Pro Pro Glu Gln Ala Phe Phe Val Leu His Lys Lys Ser Ser
    210                 215                 220
```

```
Asp Phe Val Ser Phe Glu Cys Lys Asn Leu Pro Gly Thr Tyr Ile Gly
225                 230                 235                 240

Val Lys Asp Asn Gln Leu Ala Leu Val Glu Glu Lys Asp Glu Ser Cys
            245                 250                 255

Asn Asn Ile Met Phe Lys Leu Ser Lys Ile
            260                 265

<210> SEQ ID NO 7
<211> LENGTH: 801
<212> TYPE: DNA
<213> ORGANISM: Homo sapiens

<400> SEQUENCE: 7
atgagaccta gaatgaagta ttccaactcc aagatttccc cggcaaagtt cagcagcacc        60
gcaggcgaag ccctggtccc gccttgcaaa ataagaagat cccaacagaa gaccaaagaa       120
ttctgccatg tctactgcat gagactccgt tctggcctca ccataagaaa ggagactagt       180
tattttagga aagaacccac gaaaagatat tcactaaaat cgggtaccaa gcatgaagag       240
aacttctctg cctatccacg ggattctagg aagagatcct tgcttggcag tatccaagca       300
tttgctgcgt ctgttgacac attgagcatc caaggaactt cacttttaac acagtctcct       360
gcctccctga gtacatacaa tgaccaatct gttagttttg ttttggagaa tggatgttat       420
gtgatcaatg ttgacgactc tggaaaagac caagagcaag accaggtgct actacgctac       480
tatgagtctc cctgtcctgc aagtcaatca ggcgacggtg tggatgggaa gaagctgatg       540
gtgaacatga gtcccatcaa agacacagac atctggctgc atgccaacga caaggactac       600
tccgtggagc ttcaaagggg tgacgtctcg cctccggaac aggccttctt cgtccttcac       660
aaaaagtcct cggactttgt ttcatttgaa tgcaagaatc ttcctggcac ttacatagga       720
gtaaaagata accagctggc tctagtggag gagaaagatg agagctgcaa caatattatg       780
tttaagctct cgaaaatcta a                                                 801

<210> SEQ ID NO 8
<211> LENGTH: 801
<212> TYPE: DNA
<213> ORGANISM: Homo sapiens

<400> SEQUENCE: 8
atgagaccta gaatgaagta ttccaactcc aagatttccc cggcaaagtt cagcagcacc        60
gcaggcgaag ccctggtccc gccttgcaaa ataagaagat cccaacagaa gaccaaagaa       120
ttctgccatg tctactgcat gagactccgt tctggcctca ccataagaaa ggagactagt       180
tattttagga aagaacccac gaaaagatat tcactaaaat cgggtaccaa gcatgaagag       240
aacttctctg cctatccacg ggattctagg aagagatcct tgcttggcag tatccaagca       300
tttgctgcgt ctgttgacac attgagcatc caaggaactt cacttttaac acagtctcct       360
gcctccctga gtacatacaa tgaccaatct gttagttttg ttttggagaa tggatgttat       420
gtgatcaatg ttgacgactc tggaaaagac caagagcaag accaggtgct actacgctac       480
tatgagtctc cctgtcctgc aagtcaatca ggcgacggtg tggatgggaa gaagctgatg       540
gtgaacatga gtcccatcaa agacacagac atctggctgc atgccaacga caaggactac       600
tccgtggagc ttcaaagggg tgacgtctcg cctccggaac aggccttctt cgtccttcac       660
aaaaagtcct cggactttgt ttcatttgaa tgcaagaatc ttcctggcac ttacatagga       720
gtaaaagata accagctggc tctagtggag gagaaagatg agagctgcaa caatattatg       780
```
tttaagctct cgaaaatcta a                                                                 801

<210> SEQ ID NO 9
<211> LENGTH: 419
<212> TYPE: PRT
<213> ORGANISM: Homo sapiens

<400> SEQUENCE: 9

Met Ser Arg Lys Ile Ser Lys Glu Ser Lys Val Asn Ile Ser Ser
1               5                   10                  15

Ser Leu Glu Ser Glu Asp Ile Ser Leu Glu Thr Thr Val Pro Thr Asp
                20                  25                  30

Asp Ile Ser Ser Ser Glu Glu Arg Glu Gly Lys Val Arg Ile Thr Arg
                35                  40                  45

Gln Leu Ile Glu Arg Lys Glu Leu Leu His Asn Ile Gln Leu Leu Lys
        50                  55                  60

Ile Glu Leu Ser Gln Lys Thr Met Met Ile Asp Asn Leu Lys Val Asp
65                  70                  75                  80

Tyr Leu Thr Lys Ile Glu Glu Leu Glu Lys Leu Asn Asp Ala Leu
                85                  90                  95

His Gln Lys Gln Leu Leu Thr Leu Arg Leu Asp Asn Gln Leu Ala Phe
                100                 105                 110

Gln Gln Lys Asp Ala Ser Lys Tyr Gln Glu Leu Met Lys Gln Glu Met
                115                 120                 125

Glu Thr Ile Leu Leu Arg Gln Lys Gln Leu Glu Glu Thr Asn Leu Gln
130                 135                 140

Leu Arg Glu Lys Ala Gly Asp Val Arg Arg Asn Leu Arg Asp Phe Glu
145                 150                 155                 160

Leu Thr Glu Glu Gln Tyr Ile Lys Leu Lys Ala Phe Pro Glu Asp Gln
                165                 170                 175

Leu Ser Ile Pro Glu Tyr Val Ser Val Arg Phe Tyr Glu Leu Val Asn
                180                 185                 190

Pro Leu Arg Lys Glu Ile Cys Glu Leu Gln Val Lys Lys Asn Ile Leu
                195                 200                 205

Ala Glu Glu Leu Ser Thr Asn Lys Asn Gln Leu Lys Gln Leu Thr Glu
        210                 215                 220

Thr Tyr Glu Glu Asp Arg Lys Asn Tyr Ser Glu Val Gln Ile Arg Cys
225                 230                 235                 240

Gln Arg Leu Ala Leu Glu Leu Ala Asp Thr Lys Gln Leu Ile Gln Gln
                245                 250                 255

Gly Asp Tyr Arg Gln Glu Asn Tyr Asp Lys Val Lys Ser Glu Arg Asp
                260                 265                 270

Ala Leu Glu Gln Glu Val Ile Glu Leu Arg Arg Lys His Glu Ile Leu
        275                 280                 285

Glu Ala Ser His Met Ile Gln Thr Lys Glu Arg Ser Glu Leu Ser Lys
        290                 295                 300

Glu Val Val Thr Leu Glu Gln Thr Val Thr Leu Leu Gln Lys Asp Lys
305                 310                 315                 320

Glu Tyr Leu Asn Arg Gln Asn Met Glu Leu Ser Val Arg Cys Ala His
                325                 330                 335

Glu Glu Asp Arg Leu Glu Arg Leu Gln Ala Gln Leu Glu Glu Ser Lys
                340                 345                 350

Lys Ala Arg Glu Glu Met Tyr Glu Lys Tyr Val Ala Ser Arg Asp His
        355                 360                 365

```
Tyr Lys Thr Glu Tyr Glu Asn Lys Leu His Asp Glu Leu Glu Gln Ile
        370                 375                 380

Arg Leu Lys Thr Asn Gln Glu Ile Asp Gln Leu Arg Asn Ala Ser Arg
385                 390                 395                 400

Glu Met Tyr Glu Arg Glu Asn Arg Asn Leu Arg Glu Ala Arg Asp Asn
                405                 410                 415

Ala Val Ala

<210> SEQ ID NO 10
<211> LENGTH: 1257
<212> TYPE: DNA
<213> ORGANISM: Homo sapiens

<400> SEQUENCE: 10
atgtctcgaa aatttcaaa ggagtcaaaa aaagtgaaca tctctagttc tctggaatct      60
gaagatatta gtttagaaac aacagttcct acggatgata tttcctcatc agaagagcga     120
gagggcaaag tcagaatcac caggcagcta attgaacgaa agaactact tcataatatt     180 cagttactaa aaattgagct atcccagaaa actatgatga tcgacaattt gaaagtggat    240
tatcttacaa agattgaaga attggaggag aaacttaatg atgcacttca ccagaagcag    300
ctactaacat tgagattaga caaccaattg gcttttcaac agaaagatgc cagcaaatat    360
caagaattaa tgaaacaaga atggaaacc attttgttga cagaaaaca actagaagag     420 acaaatcttc agctaagaga aaaagctgga gatgttcgtc gaaacctgcg tgactttgag    480
ttgacagaag agcaatatat taaattaaaa gcttttcctg aagatcagct ttctattcct    540
gaatatgtat ctgttcgctt ctatgagcta gtgaatccat taagaaagga atctgtgaa    600 ctacaagtga aaaagaatat cctagcagaa gaattaagta caaacaaaaa ccaactgaag    660
cagctgacag agacatatga ggaagatcga aaaaactact ctgaagttca aattagatgt    720
caacgtttgg ccttagaatt agcagacaca aaacagttaa ttcagcaagg tgactaccgt    780
caagagaact atgataaagt caagagtgaa cgtgatgcac ttgaacagga gtaattgag    840 cttaggagaa acatgaaat acttgaagcc tctcacatga ttcaaacaaa gaacgaagt    900 gaattatcaa agaggtagt caccttagag caaactgtta ctttactgca aaggataaa    960 gaatatctta tcgccaaaa catggagctt agtgttcgct gtgctcatga gaggatcgc   1020 cttgaaagac ttcaagctca actggaagaa agcaaaaagg ctagagaaga gatgtatgaa   1080
aaatatgtag catccagaga ccattataaa acagaatatg aaatcaaact acatgatgaa   1140
ctagaacaaa tcagattgaa aaccaaccaa gaaattgatc aacttcgaaa tgcctctagg   1200
gaaatgtatg aacgagaaaa cagaaatctc cgagaagcaa gggataatgc tgtggct       1257

<210> SEQ ID NO 11
<211> LENGTH: 989
<212> TYPE: PRT
<213> ORGANISM: Artificial Sequence
<220> FEATURE:
<223> OTHER INFORMATION: Recombinant full-length PIBF1 (fPIBF1) aa
      1-755; with an N-terminal glutathione-S-transferase (GST) tag of
      232 amino acids

<400> SEQUENCE: 11

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30
```

```
Tyr Glu Arg Asp Glu Gly Asp Lys Trp Arg Asn Lys Lys Phe Glu Leu
         35                  40                  45
Gly Leu Glu Phe Pro Asn Leu Pro Tyr Tyr Ile Asp Gly Asp Val Lys
 50                  55                  60
Leu Thr Gln Ser Met Ala Ile Ile Arg Tyr Ile Ala Asp Lys His Asn
 65                  70                  75                  80
Met Leu Gly Gly Cys Pro Lys Glu Arg Ala Glu Ile Ser Met Leu Glu
                 85                  90                  95
Gly Ala Val Leu Asp Ile Arg Tyr Gly Val Ser Arg Ile Ala Tyr Ser
                100                 105                 110
Lys Asp Phe Glu Thr Leu Lys Val Asp Phe Leu Ser Lys Leu Pro Glu
            115                 120                 125
Met Leu Lys Met Phe Glu Asp Arg Leu Cys His Lys Thr Tyr Leu Asn
130                 135                 140
Gly Asp His Val Thr His Pro Asp Phe Met Leu Tyr Asp Ala Leu Asp
145                 150                 155                 160
Val Val Leu Tyr Met Asp Pro Met Cys Leu Asp Ala Phe Pro Lys Leu
                165                 170                 175
Val Cys Phe Lys Lys Arg Ile Glu Ala Ile Pro Gln Ile Asp Lys Tyr
            180                 185                 190
Leu Lys Ser Ser Lys Tyr Ile Ala Trp Pro Leu Gln Gly Trp Gln Ala
            195                 200                 205
Thr Phe Gly Gly Gly Asp His Pro Pro Lys Ser Asp Leu Val Pro Arg
 210                 215                 220
Gly Ser Pro Gly Ile His Arg Asp Met Ser Arg Lys Ile Ser Lys Glu
225                 230                 235                 240
Ser Lys Lys Val Asn Ile Ser Ser Ser Leu Glu Ser Glu Asp Ile Ser
                245                 250                 255
Leu Glu Thr Thr Val Pro Thr Asp Asp Ile Ser Ser Ser Glu Glu Arg
            260                 265                 270
Glu Gly Lys Val Arg Ile Thr Arg Gln Leu Ile Glu Arg Lys Glu Leu
            275                 280                 285
Leu His Asn Ile Gln Leu Leu Lys Ile Glu Leu Ser Gln Lys Thr Met
 290                 295                 300
Met Ile Asp Asn Leu Lys Val Asp Tyr Leu Thr Lys Ile Glu Glu Leu
305                 310                 315                 320
Glu Glu Lys Leu Asn Asp Ala Leu His Gln Lys Gln Leu Leu Thr Leu
                325                 330                 335
Arg Leu Asp Asn Gln Leu Ala Phe Gln Gln Lys Asp Ala Ser Lys Tyr
            340                 345                 350
Gln Glu Leu Met Lys Gln Glu Met Glu Thr Ile Leu Leu Arg Gln Lys
            355                 360                 365
Gln Leu Glu Glu Thr Asn Leu Gln Leu Arg Glu Lys Ala Gly Asp Val
 370                 375                 380
Arg Arg Asn Leu Arg Asp Phe Glu Leu Thr Glu Gln Tyr Ile Lys
385                 390                 395                 400
Leu Lys Ala Phe Pro Glu Asp Gln Leu Ser Ile Pro Glu Tyr Val Ser
                405                 410                 415
Val Arg Phe Tyr Glu Leu Val Asn Pro Leu Arg Lys Glu Ile Cys Glu
            420                 425                 430
Leu Gln Val Lys Lys Asn Ile Leu Ala Glu Glu Leu Ser Thr Asn Lys
            435                 440                 445
```

-continued

Asn Gln Leu Lys Gln Leu Thr Glu Thr Tyr Glu Glu Asp Arg Lys Asn
450                 455                 460
Tyr Ser Glu Val Gln Ile Arg Cys Gln Arg Leu Ala Leu Glu Leu Ala
465                 470                 475                 480
Asp Thr Lys Gln Leu Ile Gln Gln Gly Asp Tyr Arg Gln Glu Asn Tyr
                485                 490                 495
Asp Lys Val Lys Ser Glu Arg Asp Ala Leu Glu Gln Glu Val Ile Glu
            500                 505                 510
Leu Arg Arg Lys His Glu Ile Leu Glu Ala Ser His Met Ile Gln Thr
        515                 520                 525
Lys Glu Arg Ser Glu Leu Ser Lys Glu Val Val Thr Leu Glu Gln Thr
530                 535                 540
Val Thr Leu Leu Gln Lys Asp Lys Glu Tyr Leu Asn Arg Gln Asn Met
545                 550                 555                 560
Glu Leu Ser Val Arg Cys Ala His Glu Glu Asp Arg Leu Glu Arg Leu
                565                 570                 575
Gln Ala Gln Leu Glu Glu Ser Lys Lys Ala Arg Glu Glu Met Tyr Glu
                580                 585                 590
Lys Tyr Val Ala Ser Arg Asp His Tyr Lys Thr Glu Tyr Glu Asn Lys
        595                 600                 605
Leu His Asp Glu Leu Glu Gln Ile Arg Leu Lys Thr Asn Gln Glu Ile
    610                 615                 620
Asp Gln Leu Arg Asn Ala Ser Arg Glu Met Tyr Glu Arg Glu Asn Arg
625                 630                 635                 640
Asn Leu Arg Glu Ala Arg Asp Asn Ala Val Ala Glu Lys Glu Arg Ala
                645                 650                 655
Val Met Ala Glu Lys Asp Ala Leu Glu Lys His Asp Gln Leu Leu Asp
                660                 665                 670
Arg Tyr Arg Glu Leu Gln Leu Ser Thr Glu Ser Lys Val Thr Glu Phe
        675                 680                 685
Leu His Gln Ser Lys Leu Lys Ser Phe Glu Ser Glu Arg Val Gln Leu
    690                 695                 700
Leu Gln Glu Glu Thr Ala Arg Asn Leu Thr Gln Cys Gln Leu Glu Cys
705                 710                 715                 720
Glu Lys Tyr Gln Lys Lys Leu Glu Val Leu Thr Lys Glu Phe Tyr Ser
                725                 730                 735
Leu Gln Ala Ser Ser Glu Lys Arg Ile Thr Glu Leu Gln Ala Gln Asn
                740                 745                 750
Ser Glu His Gln Ala Arg Leu Asp Ile Tyr Glu Lys Leu Glu Lys Glu
        755                 760                 765
Leu Asp Glu Ile Ile Met Gln Thr Ala Glu Ile Glu Asn Glu Asp Glu
    770                 775                 780
Ala Glu Arg Val Leu Phe Ser Tyr Gly Tyr Gly Ala Asn Val Pro Thr
785                 790                 795                 800
Thr Ala Lys Arg Arg Leu Lys Gln Ser Val His Leu Ala Arg Arg Val
                805                 810                 815
Leu Gln Leu Glu Lys Gln Asn Ser Leu Ile Leu Lys Asp Leu Glu His
                820                 825                 830
Arg Lys Asp Gln Val Thr Gln Leu Ser Gln Leu Asp Arg Ala Asn
        835                 840                 845
Ser Leu Leu Asn Gln Thr Gln Gln Pro Tyr Arg Tyr Leu Ile Glu Ser
850                 855                 860
Val Arg Gln Arg Asp Ser Lys Ile Asp Ser Leu Thr Glu Ser Ile Ala

```
               865                 870                 875                 880
        Gln Leu Glu Lys Asp Val Ser Asn Leu Asn Lys Glu Lys Ser Ala Leu
                        885                 890                 895
        Leu Gln Thr Lys Asn Gln Met Ala Leu Asp Leu Glu Gln Leu Leu Asn
                        900                 905                 910
        His Arg Glu Glu Leu Ala Ala Met Lys Gln Ile Leu Val Lys Met His
                        915                 920                 925
        Ser Lys His Ser Glu Asn Ser Leu Leu Leu Thr Lys Thr Glu Pro Lys
                        930                 935                 940
        His Val Thr Glu Asn Gln Lys Ser Lys Thr Leu Asn Val Pro Lys Glu
        945                 950                 955                 960
        His Glu Asp Asn Ile Phe Thr Pro Lys Pro Thr Leu Phe Thr Lys Lys
                        965                 970                 975
        Glu Ala Pro Glu Trp Ser Lys Lys Gln Lys Met Lys Thr
                        980                 985

<210> SEQ ID NO 12
<211> LENGTH: 328
<212> TYPE: PRT
<213> ORGANISM: Homo sapiens

<400> SEQUENCE: 12

Met Ser Pro Ile Leu Gly Tyr Trp Lys Ile Lys Gly Leu Val Gln Pro
        1               5                   10                  15
        Thr Arg Leu Leu Leu Glu Tyr Leu Glu Glu Lys Tyr Glu Glu His Leu
                        20                  25                  30
        Tyr Glu Arg Asp Glu Gly Asp Lys Trp Arg Asn Lys Lys Phe Glu Leu
                        35                  40                  45
        Gly Leu Glu Phe Pro Asn Leu Pro Tyr Tyr Ile Asp Gly Asp Val Lys
                        50                  55                  60
        Leu Thr Gln Ser Met Ala Ile Ile Arg Tyr Ile Ala Asp Lys His Asn
        65                  70                  75                  80
        Met Leu Gly Gly Cys Pro Lys Glu Arg Ala Glu Ile Ser Met Leu Glu
                        85                  90                  95
        Gly Ala Val Leu Asp Ile Arg Tyr Gly Val Ser Arg Ile Ala Tyr Ser
                        100                 105                 110
        Lys Asp Phe Glu Thr Leu Lys Val Asp Phe Leu Ser Lys Leu Pro Glu
                        115                 120                 125
        Met Leu Lys Met Phe Glu Asp Arg Leu Cys His Lys Thr Tyr Leu Asn
                        130                 135                 140
        Gly Asp His Val Thr His Pro Asp Phe Met Leu Tyr Asp Ala Leu Asp
        145                 150                 155                 160
        Val Val Leu Tyr Met Asp Pro Met Cys Leu Asp Ala Phe Pro Lys Leu
                        165                 170                 175
        Val Cys Phe Lys Lys Arg Ile Glu Ala Ile Pro Gln Ile Asp Lys Tyr
                        180                 185                 190
        Leu Lys Ser Ser Lys Tyr Ile Ala Trp Pro Leu Gln Gly Trp Gln Ala
                        195                 200                 205
        Thr Phe Gly Gly Gly Asp His Pro Pro Lys Ser Asp Leu Val Pro Arg
                        210                 215                 220
        Gly Ser Pro Gly Ile His Arg Asp Glu Lys Ser Ala Leu Leu Gln Thr
        225                 230                 235                 240
        Lys Asn Gln Met Ala Leu Asp Leu Glu Gln Leu Leu Asn His Arg Glu
                        245                 250                 255
```

```
Glu Leu Ala Ala Met Lys Gln Ile Leu Val Lys Met His Ser Lys His
                260                 265                 270

Ser Glu Asn Ser Leu Leu Leu Thr Lys Thr Glu Pro Lys His Val Thr
            275                 280                 285

Glu Asn Gln Lys Ser Lys Thr Leu Asn Val Pro Lys Glu His Glu Asp
        290                 295                 300

Asn Ile Phe Thr Pro Lys Pro Thr Leu Phe Thr Lys Lys Glu Ala Pro
305                 310                 315                 320

Glu Trp Ser Lys Lys Gln Lys Met
                325
```

<210> SEQ ID NO 13
<211> LENGTH: 19
<212> TYPE: DNA
<213> ORGANISM: Artificial Sequence
<220> FEATURE:
<223> OTHER INFORMATION: Sense PCR primer for GAPDH

<400> SEQUENCE: 13
gaaggtgaag gtcggagtc                                                    19

<210> SEQ ID NO 14
<211> LENGTH: 20
<212> TYPE: DNA
<213> ORGANISM: Artificial Sequence
<220> FEATURE:
<223> OTHER INFORMATION: Antisense PCR primer for GAPDH

<400> SEQUENCE: 14
gaagatggtg atgggatttc                                                   20

<210> SEQ ID NO 15
<211> LENGTH: 25
<212> TYPE: DNA
<213> ORGANISM: Artificial Sequence
<220> FEATURE:
<223> OTHER INFORMATION: Sense PCR primer for PIBF1

<400> SEQUENCE: 15
cttacaaaga ttgaagaatt ggagg                                             25

<210> SEQ ID NO 16
<211> LENGTH: 25
<212> TYPE: DNA
<213> ORGANISM: Artificial Sequence
<220> FEATURE:
<223> OTHER INFORMATION: Antisense PCR primer for PIBF1

<400> SEQUENCE: 16
aattcttgat atttgctggc atctt                                             25

<210> SEQ ID NO 17
<211> LENGTH: 21
<212> TYPE: DNA
<213> ORGANISM: Artificial Sequence
<220> FEATURE:
<223> OTHER INFORMATION: Sense PCR primer for TNFSF13

<400> SEQUENCE: 17
ctgcacctgg ttcccattaa c                                                 21

<210> SEQ ID NO 18
<211> LENGTH: 21
<212> TYPE: DNA

```
<213> ORGANISM: Artificial Sequence
<220> FEATURE:
<223> OTHER INFORMATION: Antisense PCR primer for TNFSF13

<400> SEQUENCE: 18
aagagctggt tgccacatca c                                              21

<210> SEQ ID NO 19
<211> LENGTH: 19
<212> TYPE: DNA
<213> ORGANISM: Artificial Sequence
<220> FEATURE:
<223> OTHER INFORMATION: Sense PCR primer for TNFSF13B

<400> SEQUENCE: 19
accgcgggac tgaaaatct                                                 19

<210> SEQ ID NO 20
<211> LENGTH: 23
<212> TYPE: DNA
<213> ORGANISM: Artificial Sequence
<220> FEATURE:
<223> OTHER INFORMATION: Antisense PCR primer for TNFSF13B

<400> SEQUENCE: 20
cacgcttatt tctgctgttc tga                                            23

<210> SEQ ID NO 21
<211> LENGTH: 22
<212> TYPE: DNA
<213> ORGANISM: Artificial Sequence
<220> FEATURE:
<223> OTHER INFORMATION: Sense PCR primer for TSLP

<400> SEQUENCE: 21
cccaggctat tcggaaactc ag                                             22

<210> SEQ ID NO 22
<211> LENGTH: 22
<212> TYPE: DNA
<213> ORGANISM: Artificial Sequence
<220> FEATURE:
<223> OTHER INFORMATION: Antisense PCR primer for TSLP

<400> SEQUENCE: 22
cgccacaatc cttgtaattg tg                                             22

<210> SEQ ID NO 23
<211> LENGTH: 21
<212> TYPE: DNA
<213> ORGANISM: Artificial Sequence
<220> FEATURE:
<223> OTHER INFORMATION: Sense PCR primer for Gapdh

<400> SEQUENCE: 23
aggtcggtgt gaacggattt g                                              21

<210> SEQ ID NO 24
<211> LENGTH: 23
<212> TYPE: DNA
<213> ORGANISM: Artificial Sequence
<220> FEATURE:
<223> OTHER INFORMATION: Antisense PCR primer for Gapdh

<400> SEQUENCE: 24
tgtagaccat gtagttgagg tca                                            23
```

<210> SEQ ID NO 25
<211> LENGTH: 21
<212> TYPE: DNA
<213> ORGANISM: Artificial Sequence
<220> FEATURE:
<223> OTHER INFORMATION: Sense PCR primer for Tnf

<400> SEQUENCE: 25
ggaacacgtc gtgggataat g                                        21

<210> SEQ ID NO 26
<211> LENGTH: 21
<212> TYPE: DNA
<213> ORGANISM: Artificial Sequence
<220> FEATURE:
<223> OTHER INFORMATION: Antisense PCR primer for Tnf

<400> SEQUENCE: 26
ggcagacttt ggatgcttct t                                        21

<210> SEQ ID NO 27
<211> LENGTH: 22
<212> TYPE: DNA
<213> ORGANISM: Artificial Sequence
<220> FEATURE:
<223> OTHER INFORMATION: Sense PCR primer for Il1b

<400> SEQUENCE: 27
gcaactgttc ctgaactcaa ct                                       22

<210> SEQ ID NO 28
<211> LENGTH: 21
<212> TYPE: DNA
<213> ORGANISM: Artificial Sequence
<220> FEATURE:
<223> OTHER INFORMATION: Antisense PCR primer for Il1b

<400> SEQUENCE: 28
atcttttggg gtccgtcaac t                                        21

<210> SEQ ID NO 29
<211> LENGTH: 23
<212> TYPE: DNA
<213> ORGANISM: Artificial Sequence
<220> FEATURE:
<223> OTHER INFORMATION: Sense PCR primer for Il6

<400> SEQUENCE: 29
tagtccttcc taccccaatt tcc                                      23

<210> SEQ ID NO 30
<211> LENGTH: 21
<212> TYPE: DNA
<213> ORGANISM: Artificial Sequence
<220> FEATURE:
<223> OTHER INFORMATION: Antisense PCR primer for Il6

<400> SEQUENCE: 30
ttggtcctta gccactcctt c                                        21

<210> SEQ ID NO 31
<211> LENGTH: 19
<212> TYPE: DNA
<213> ORGANISM: Artificial Sequence
<220> FEATURE:

<223> OTHER INFORMATION: Sense PCR primer for Mmp9

<400> SEQUENCE: 31
ggacccgaag cggacattg                                            19

<210> SEQ ID NO 32
<211> LENGTH: 20
<212> TYPE: DNA
<213> ORGANISM: Artificial Sequence
<220> FEATURE:
<223> OTHER INFORMATION: Antisense PCR primer for Mmp9

<400> SEQUENCE: 32
cgtcgtcgaa atgggcatct                                           20

<210> SEQ ID NO 33
<211> LENGTH: 23
<212> TYPE: DNA
<213> ORGANISM: Artificial Sequence
<220> FEATURE:
<223> OTHER INFORMATION: Sense PCR primer for Cxcl1

<400> SEQUENCE: 33
ctgggattca cctcaagaac atc                                       23

<210> SEQ ID NO 34
<211> LENGTH: 19
<212> TYPE: DNA
<213> ORGANISM: Artificial Sequence
<220> FEATURE:
<223> OTHER INFORMATION: Antisense PCR primer for Cxcl1

<400> SEQUENCE: 34
cagggtcaag gcaagcctc                                            19

<210> SEQ ID NO 35
<211> LENGTH: 20
<212> TYPE: DNA
<213> ORGANISM: Artificial Sequence
<220> FEATURE:
<223> OTHER INFORMATION: Sense PCR primer for Cxcl5

<400> SEQUENCE: 35
gcggctatga ctgaggaagg                                           20

<210> SEQ ID NO 36
<211> LENGTH: 21
<212> TYPE: DNA
<213> ORGANISM: Artificial Sequence
<220> FEATURE:
<223> OTHER INFORMATION: Antisense PCR primer for Cxcl5

<400> SEQUENCE: 36
gttccatctc gccattcatg c                                         21

<210> SEQ ID NO 37
<211> LENGTH: 20
<212> TYPE: DNA
<213> ORGANISM: Artificial Sequence
<220> FEATURE:
<223> OTHER INFORMATION: Sense PCR primer for Pibf1

<400> SEQUENCE: 37
gctgacagaa gagcagtatg                                           20

```
<210> SEQ ID NO 38
<211> LENGTH: 21
<212> TYPE: DNA
<213> ORGANISM: Artificial Sequence
<220> FEATURE:
<223> OTHER INFORMATION: Antisense PCR primer for Pibf1

<400> SEQUENCE: 38
cgagctcata gaagcgaata g                                              21

<210> SEQ ID NO 39
<211> LENGTH: 19
<212> TYPE: DNA
<213> ORGANISM: Artificial Sequence
<220> FEATURE:
<223> OTHER INFORMATION: Sense PCR primer for Cxcl2

<400> SEQUENCE: 39
ccaaccacca ggctacagg                                                 19

<210> SEQ ID NO 40
<211> LENGTH: 19
<212> TYPE: DNA
<213> ORGANISM: Artificial Sequence
<220> FEATURE:
<223> OTHER INFORMATION: Antisense PCR primer for Cxcl2

<400> SEQUENCE: 40
gcgtcacact caagctctg                                                 19

<210> SEQ ID NO 41
<211> LENGTH: 23
<212> TYPE: DNA
<213> ORGANISM: Artificial Sequence
<220> FEATURE:
<223> OTHER INFORMATION: Sense PCR primer for Ccl3

<400> SEQUENCE: 41
ttctctgtac catgacactc tgc                                            23

<210> SEQ ID NO 42
<211> LENGTH: 21
<212> TYPE: DNA
<213> ORGANISM: Artificial Sequence
<220> FEATURE:
<223> OTHER INFORMATION: Antisense PCR primer for Ccl3

<400> SEQUENCE: 42
cgtggaatct tccggctgta g                                              21

<210> SEQ ID NO 43
<211> LENGTH: 21
<212> TYPE: DNA
<213> ORGANISM: Artificial Sequence
<220> FEATURE:
<223> OTHER INFORMATION: Sense PCR primer for Cxcl10

<400> SEQUENCE: 43
ccaagtgctg ccgtcatttt c                                              21

<210> SEQ ID NO 44
<211> LENGTH: 21
<212> TYPE: DNA
<213> ORGANISM: Artificial Sequence
<220> FEATURE:
<223> OTHER INFORMATION: Antisense PCR primer for Cxcl10
```

```
<400> SEQUENCE: 44
ggctcgcagg gatgatttca a                                              21

<210> SEQ ID NO 45
<211> LENGTH: 23
<212> TYPE: DNA
<213> ORGANISM: Artificial Sequence
<220> FEATURE:
<223> OTHER INFORMATION: Sense PCR primer for Ccl2

<400> SEQUENCE: 45
ttaaaaacct ggatcggaac caa                                            23

<210> SEQ ID NO 46
<211> LENGTH: 23
<212> TYPE: DNA
<213> ORGANISM: Artificial Sequence
<220> FEATURE:
<223> OTHER INFORMATION: Antisense PCR primer for Ccl2

<400> SEQUENCE: 46
gcattagctt cagatttacg ggt                                            23

<210> SEQ ID NO 47
<211> LENGTH: 21
<212> TYPE: DNA
<213> ORGANISM: Artificial Sequence
<220> FEATURE:
<223> OTHER INFORMATION: Sense PCR primer for Cxcl9

<400> SEQUENCE: 47
tccttttggg catcatcttc c                                              21

<210> SEQ ID NO 48
<211> LENGTH: 21
<212> TYPE: DNA
<213> ORGANISM: Artificial Sequence
<220> FEATURE:
<223> OTHER INFORMATION: Antisense PCR primer for Cxcl9

<400> SEQUENCE: 48
tttgtagtgg atcgtgcctc g                                              21

<210> SEQ ID NO 49
<211> LENGTH: 19
<212> TYPE: DNA
<213> ORGANISM: Artificial Sequence
<220> FEATURE:
<223> OTHER INFORMATION: Sense PCR primer for Ebi3

<400> SEQUENCE: 49
ctctcccctg gttacactg                                                 19

<210> SEQ ID NO 50
<211> LENGTH: 19
<212> TYPE: DNA
<213> ORGANISM: Artificial Sequence
<220> FEATURE:
<223> OTHER INFORMATION: antisense pcr primer for ebi3

<400> SEQUENCE: 50
ccacgggata ccgagaagc                                                 19

<210> SEQ ID NO 51
<211> LENGTH: 21
```

```
<212> TYPE: DNA
<213> ORGANISM: Artificial Sequence
<220> FEATURE:
<223> OTHER INFORMATION: Sense PCR primer for Il10

<400> SEQUENCE: 51
gctcttactg actggcatga g                                              21

<210> SEQ ID NO 52
<211> LENGTH: 20
<212> TYPE: DNA
<213> ORGANISM: Artificial Sequence
<220> FEATURE:
<223> OTHER INFORMATION: Antisense PCR primer for Il10

<400> SEQUENCE: 52
cgcagctcta ggagcatgtg                                                20

<210> SEQ ID NO 53
<211> LENGTH: 23
<212> TYPE: DNA
<213> ORGANISM: Artificial Sequence
<220> FEATURE:
<223> OTHER INFORMATION: Sense PCR primer for Tgfb1

<400> SEQUENCE: 53
cttcaatacg tcagacattc ggg                                            23

<210> SEQ ID NO 54
<211> LENGTH: 22
<212> TYPE: DNA
<213> ORGANISM: Artificial Sequence
<220> FEATURE:
<223> OTHER INFORMATION: Antisense PCR primer for Tgfb1

<400> SEQUENCE: 54
gtaacgccag gaattgttgc ta                                             22
```

METHOD OF PREVENTION AND INHIBITION OF PRETERM LABOR

REFERENCE TO RELATED APPLICATION

This application claims priority to U.S. Provisional Patent Application Ser. No. 62/381,964, filed Aug. 31, 2016, the entire content of which is incorporated herein by reference.

FIELD OF THE INVENTION

Aspects of the present invention relate generally to methods and compositions to prevent and/or inhibit of preterm labor in a pregnant subject. According to specific aspects of the present invention, methods of preventing and/or inhibiting preterm labor in a pregnant subject including administering a therapeutically effective amount of a protein selected from the group consisting of: PIBF1, a fragment or variant thereof; IL-33, a fragment or variant thereof; and a combination of any two or more thereof are described.

BACKGROUND OF THE INVENTION

Preterm birth (PTB), defined as birth before 37 weeks of gestation, affects 5-18% pregnancies worldwide and has remained an intractable cause of neonatal mortality and long-term morbidity. There is a continuing need for methods and compositions to prevent and/or inhibit of preterm labor in a pregnant subject.

SUMMARY OF THE INVENTION

Methods of preventing and/or inhibiting preterm labor in a pregnant subject according to aspects of the present invention include administering a therapeutically effective amount of: PIBF1, a fragment or variant thereof; IL-33, a fragment or variant thereof; or a combination of any two or more thereof, to a pregnant subject in need thereof. According to aspects of the present invention, the pregnant subject is human.

Methods of preventing and/or inhibiting preterm labor in a pregnant subject according to aspects of the present invention include administering a therapeutically effective amount of PIBF1 including or consisting of the amino acid sequence of SEQ ID NO: 1, a fragment or variant thereof, wherein the PIBF1 protein, PIBF1 fragment or PIBF1 variant thereof is effective to prevent and/or inhibit preterm labor in the pregnant subject. Optionally, the PIBF1 protein administered is a protein including, or consisting of, an amino acid sequence that is at least 95% identical to SEQ ID NO: 1.

Methods of preventing and/or inhibiting preterm labor in a pregnant subject according to aspects of the present invention include administering a therapeutically effective amount of PIBF1 including or consisting of the amino acid sequence of SEQ ID NO: 2, a fragment or variant thereof, wherein the PIBF1 protein, PIBF1 fragment or PIBF1 variant thereof is effective to prevent and/or inhibit preterm labor in the pregnant subject. Optionally, the PIBF1 protein administered is a protein including, or consisting of, an amino acid sequence that is at least 95% identical to SEQ ID NO: 2.

Methods of preventing and/or inhibiting preterm labor in a pregnant subject according to aspects of the present invention include administering a therapeutically effective amount of PIBF1 including or consisting of the amino acid sequence of SEQ ID NO: 9, a fragment or variant thereof, wherein the PIBF1 protein, PIBF1 fragment or PIBF1 variant thereof is effective to prevent and/or inhibit preterm labor in the pregnant subject. Optionally, the PIBF1 protein administered is a protein including, or consisting of, an amino acid sequence that is at least 95% identical to SEQ ID NO: 9.

Methods of preventing and/or inhibiting preterm labor in a pregnant subject according to aspects of the present invention include administering a therapeutically effective amount of IL-33 including or consisting of the amino acid sequence of SEQ ID NO: 5, a fragment or variant thereof, wherein the IL-33 protein, IL-33 fragment or IL-33 variant thereof is effective to prevent and/or inhibit preterm labor in the pregnant subject. Optionally, the IL-33 protein administered is a protein including, or consisting of, an amino acid sequence that is at least 95% identical to SEQ ID NO: 5.

Methods of preventing and/or inhibiting preterm labor in a pregnant subject according to aspects of the present invention include administering a therapeutically effective amount of IL-33 including or consisting of the amino acid sequence of SEQ ID NO: 6, a fragment or variant thereof, wherein the IL-33 protein, IL-33 fragment or IL-33 variant thereof is effective to prevent and/or inhibit preterm labor in the pregnant subject. Optionally, the IL-33 protein administered is a protein including, or consisting of, an amino acid sequence that is at least 95% identical to SEQ ID NO: 6.

Methods of preventing and/or inhibiting preterm labor in a pregnant subject according to aspects of the present invention include administering a therapeutically effective amount of PIBF1 including or consisting of the amino acid sequence of SEQ ID NO: 1, a fragment or variant thereof, wherein the PIBF1 protein, PIBF1 fragment or PIBF1 variant thereof is effective to prevent and/or inhibit preterm labor in the pregnant subject and wherein the PIBF1 protein, PIBF1 fragment or PIBF1 variant thereof is encoded by the complement of a nucleic acid that hybridizes under highly stringent conditions with the nucleotide sequence of SEQ ID NO: 3.

Methods of preventing and/or inhibiting preterm labor in a pregnant subject according to aspects of the present invention include administering a therapeutically effective amount of PIBF1 including or consisting of the amino acid sequence of SEQ ID NO: 2, a fragment or variant thereof, wherein the PIBF1 protein, PIBF1 fragment or PIBF1 variant thereof is effective to prevent and/or inhibit preterm labor in the pregnant subject and wherein the PIBF1 protein, PIBF1 fragment or PIBF1 variant thereof is encoded by the complement of a nucleic acid that hybridizes under highly stringent conditions with the nucleotide sequence of SEQ ID NO: 4.

Methods of preventing and/or inhibiting preterm labor in a pregnant subject according to aspects of the present invention include administering a therapeutically effective amount of PIBF1 including or consisting of the amino acid sequence of SEQ ID NO: 9, a fragment or variant thereof, wherein the PIBF1 protein, PIBF1 fragment or PIBF1 variant thereof is effective to prevent and/or inhibit preterm labor in the pregnant subject and wherein the PIBF1 protein, PIBF1 fragment or PIBF1 variant thereof is encoded by the complement of a nucleic acid that hybridizes under highly stringent conditions with the nucleotide sequence of SEQ ID NO: 10.

Methods of preventing and/or inhibiting preterm labor in a pregnant subject according to aspects of the present invention include administering a therapeutically effective amount of IL-33 including or consisting of the amino acid sequence of SEQ ID NO: 5, a fragment or variant thereof, wherein the IL-33 protein, IL-33 fragment or IL-33 variant thereof is effective to prevent and/or inhibit preterm labor in the pregnant subject and wherein the IL-33 protein, IL-33 fragment or IL-33 variant thereof is encoded by the complement of a nucleic acid that hybridizes under highly stringent conditions with the nucleotide sequence of SEQ ID NO: 7.

Methods of preventing and/or inhibiting preterm labor in a pregnant subject according to aspects of the present invention include administering a therapeutically effective amount of IL-33 including or consisting of the amino acid sequence of SEQ ID NO: 6, a fragment or variant thereof, wherein the IL-33 protein, IL-33 fragment or IL-33 variant thereof is effective to prevent and/or inhibit preterm labor in the pregnant subject and wherein the IL-33 protein, IL-33 fragment or IL-33 variant thereof is encoded by the complement of a nucleic acid that hybridizes under highly stringent conditions with the nucleotide sequence of SEQ ID NO: 8.

Methods of preventing and/or inhibiting preterm labor in a pregnant subject according to aspects of the present invention include administering a therapeutically effective amount of: PIBF1, a fragment or variant thereof; IL-33, a fragment or variant thereof; or a combination of any two or more thereof, to a pregnant subject in need thereof, wherein administering the therapeutically effective amount includes administering an expression vector encoding the protein selected from the group consisting of: PIBF1, a fragment or variant thereof; IL-33, a fragment or variant thereof; and a combination of any two or more thereof to one or more cells of the subject, thereby expressing the protein in the subject. According to aspects of the present invention, the pregnant subject is human.

Optionally, methods of preventing and/or inhibiting preterm labor in a pregnant subject according to aspects of the present invention further includes administering one or more therapeutic agents in addition to administering a therapeutically effective amount of: PIBF1, a fragment or variant thereof; IL-33, a fragment or variant thereof; or a combination of any two or more thereof. Administration of the one or more therapeutic agents can be at the same time, before, after, or at combinations of any two or more thereof with reference to administration of the therapeutically effective amount of: PIBF1, a fragment or variant thereof; IL-33, a fragment or variant thereof; or a combination of any two or more thereof.

Compositions for preventing and/or inhibiting preterm labor in a pregnant subject in need thereof, including 1) a protein selected from the group consisting of: PIBF1, a PIBF1 variant, IL-33, an IL-33 variant and a combination of any two or more thereof; and a pharmaceutically acceptable carrier; or 2) an expression vector encoding a protein selected from the group consisting of: PIBF1, a PIBF1 variant, IL-33, an IL-33 variant and a combination of any two or more thereof; and a pharmaceutically acceptable carrier; or 3) a combination of both 1) and 2); and optionally one or more additional therapeutic agents.

BRIEF DESCRIPTION OF THE DRAWINGS

FIGS. 1A and 1B show frequency of CD19+ B cells in choriodecidua of women with spontaneous term labor (TL) (n=21) or PTL (n=12), as determined by flow cytometry. FIG. 1C shows calculated numbers of CD19+ B cells recovered from choriodecidual tissues of women with TL (n=21) or PTL (n=12). : $p<0.01$; *: $p<0.001$, by 2-tailed t-test for FIGS. 1B and 1C.

FIGS. 2A and 2B show rates of preterm delivery and neonatal/fetal mortality of WT or μMT mice 24 hours after receiving the indicated intraperitoneal dose of LPS given on gd 16.5. FIG. 2C shows fold change of Tnf, Il1b, Il6, Mmp9, Cxcl1 and Cxcl5 transcripts in uterine tissues of WT or μMT mice 24 hours after receiving the indicated intraperitoneal dose of LPS, relative to the gene transcripts in uterine tissues of the respective strain of mice that did not receive LPS. FIG. 2D shows frequency of CD11b+Ly-6G+ neutrophils in CD45+ cells in uterine tissues of representative WT and μMT mice 24 hours after receiving 5 μg LPS. FIG. 2E shows expression of surface CD11b, CD18, CD62L and intracellular iNOS by viable neutrophils in uterine tissues of a representative WT or μMT mouse 24 hours after receiving 5 μg LPS. FIGS. 2F and 2G show rate of preterm delivery and neonatal/fetal mortality on gd 17.5 of μMT mice that intravenously received either PBS, or 10⁷ WT or IL-10−/− B cells on gd 14.5 and 5 μg LPS on gd 16.5. FIG. 2H shows fold change of Tnf, Il1b, Il6, Mmp9, Cxcl1 and Cxcl5 transcripts in uterine tissues of gd 17.5 μMT mice after receiving either PBS, or 10⁷ WT or IL-10−/− B cells on gd 14.5 and 5 μg LPS, relative to the gene transcripts in uterine tissues of the respective mice that did not receive LPS. FIG. 2I shows frequency of CD11b+Ly-6G+ neutrophils in CD45+ cells in uterine tissues of gd 17.5 μMT mice after receiving either PBS, or 10⁷ WT or IL-10−/− B cells on gd 14.5 and 5 μg LPS on gd 16.5. Data in FIGS. 2A and 2B represent the results of 6 WT mice (PBS, 0.5, and 10 μg LPS groups), 7 WT mice (2.5 and 5 μg LPS groups), 4 WT mice (20 μg LPS group), 5 μMT mice (PBS and 20 μg LPS groups), 8 μMT mice (2.5 and 10 μg LPS groups), 9 μMT mice (0.51 μg LPS group) or 10 μMT mice (5 μg LPS group) per group. Data in FIG. 2C represent the results of 5 mice per group. Data in FIGS. 2D and 2E represent the results of 7 WT mice and 9 μMT mice. Data in FIGS. 2F, 2G, 2H and 2I represent the results of 5 mice per group. *: $p<0.05$; **: $p<0.01$, by Fisher's exact test (for FIGS. 2A and 2F), 1-tailed Mann-Whitney U test (for FIGS. 2B and 2G), or 1-tailed t-test (for FIGS. 2C and 2H).

FIGS. 3A, 3B, 3C, 3D, 3E, 3F, 3G, 3H, 3I, 3J, 3K, 3L, 3M, and 3N demonstrate that B cells protect against PTL via PIBF1-dependent suppression of uterine inflammation. FIG. 3A shows a Western Blot analysis of PIBF1 in uterine tissues of WT or μMT mice on gd 16.5. FIG. 3B shows fold change of Pibf1 transcript in uterine tissues of WT or μMT mice 24 hours after receiving the indicated intraperitoneal dose of LPS given on gd 16.5, relative to the gene transcripts in uterine tissues of the respective mice that did not receive LPS. FIG. 3C shows fold change of Pibf1 transcript in uterine tissues of gd 17.5 μMT mice after receiving either PBS, or 10⁷ WT or IL-10−/− B cells on gd 14.5 and 5 μg LPS on gd 16.5, relative to the gene transcripts in uterine tissues of the respective mice that did not receive LPS. FIG. 3D shows Western Blot analysis of PIBF1 in uterine tissues of μMT mice on gd 16.5 that received 10⁷ WT or IL-10−/− B cells on gd 14.5. FIG. 3E shows flow cytometry analysis of PIBF1 and IL-10 expression by uterine CD19+ B cells in non-pregnant WT mice, pregnant WT mice on gd 10.5 or 16.5. FIG. 3F shows flow cytometry analysis of PIBF1 expression by choriodecidual CD19+ B cells in a woman with TL. FIG. 3G shows immunohistochemical analysis of TL choriodecidual stroma for CD19. Bars: 20 µm. FIG. 3H shows imaging flow cytometry analysis of PIBF1 expression by TL choriodecidual CD19+ B cells. DNA was counter-stained with Hoechst 33342. Arrow heads point to perinuclear PIBF1 staining concentrated at areas resembling centrosomes. Bar: 7 µm. FIGS. 3I and 3J show rates of preterm delivery and neonatal/fetal mortality on gd 17.5 of gpMT mice that received either intravenous PBS or 1 µg full-length recombinant PIBF1 (fPIBF1) and 5 µg intraperitoneal LPS on gd 16.5. FIG. 3K shows fold change of Tnf, 116, Mmp9, Cxcl2, Cxcl3 and Cxcl5 transcripts in uterine tissues of µMT mice 24 hours after intravenous fPIBF1 administration and 5 µg intraperitoneal LPS, relative to the gene transcripts in uterine tissues of the mice that received PIBF1 but not LPS. FIGS. 3L and 3M show frequency of CD11b+Ly-6G+ neutrophils in CD45+ cells in uterine tissues of gd 17.5 µMT mice after receiving either intravenous PBS or PIBF1 and intraperitoneal LPS on gd 16.5. FIG. 3N shows expression of surface CD11b, CD18, CD62L and intracellular iNOS by viable neutrophils in uterine tissues of a representative µMT mouse 24 hours after receiving intravenous PBS or PIBF1 and intraperitoneal LPS. Data represent the results from 5 mice (FIGS. 3A, 3B, 3C, 3D and 3E) or 9 mice (FIGS. 3I, 3J, 3K, 3L, 3M and 3N) per group. *: $p<0.05$; : $p<0.01$; *: $p<0.001$, by Fisher's exact test (FIG. 3I), 1-tailed Mann-Whitney U test (FIG. 3J), or 1-tailed t-test (FIGS. 3B, 3C, 3K and 3M).

FIGS. 4A, 4B, 4C, 4D, 4E, 4F, 4G, 4H, 4I, 4J, and 4K demonstrate that IL-33-dependent PIBF1 expression by decidual B cells is defective in human PTL. FIG. 4A shows fold change of PIBF1 transcript in purified human PB IgD+B cells after 3 days of stimulation with 1 µM progesterone or 100 ng/ml IL-33, relative to unstimulated control IgD+B cells. FIG. 4B shows a Western Blot of PIBF1 in purified human PB IgD+B cells after 2 days of treatment with medium (control), 1 µM progesterone or 100 ng/ml IL-33. Data in FIGS. 4A and 4B represent the results from 9 donors. FIGS. 4C and 4D show Western Blot and flow cytometric analyses of PIBF1 expression in uterine tissue or uterine B cells of age-matched pregnant WT and IL-33−/− mice on gd 16.5. Data represent 3 mice per group. FIG. 4E shows flow cytometry of surface ST2L on B cells in choriodecidual tissues of a woman with TL or a woman with PTL or peripheral blood of a healthy donor. FIGS. 4F and 4G show frequency of ST2L+ cells and mean fluorescence intensity of surface ST2L staining in choriodecidual B cells of women with TL (n=21) or PTL (n=12) and peripheral blood B cells of healthy donors (n=28). FIG. 4H shows Western Blot analysis of PIBF1 and IL-33 expression in choriodecidual tissue of a woman with TL and a woman with PTL. Data represent 4 TL and 4 PTL subjects. #: IL-33 runs at a molecular weight higher than its predicted molecular weight. FIG. 4I shows flow cytometric analysis of PIBF1 expression in choriodecidual CD19+ B cells of a woman with TL and a woman with PTL. FIG. 4J shows frequency of PIBF1+ choriodecidual B cells of TL (n=20) and PTL (n=12) subjects. FIG. 4K shows a proposed model of choriodecidual B cell-mediated protection against PTL via IL-33-dependent expression of PIBF1. B cells migrate to choriodecidua during pregnancy, which may be mediated by signals involving a4 and 37 integrins. In choriodecidua, B cells produce antibodies to contribute to protection against intra-amniotic infection during pregnancy. In response to IL-33, an alarmin that is activated by uterine stress and inflammation, decidual B cells also produce PIBF1 to suppress premature parturition via the inhibition of the production of labor-inducing factors, natural killer (NK) cell activity, neutrophil infiltration and activation and the production of proinflammatory mediators. Hence, IL-33, choriodecidual B cells and PIBF1 constitute a protective axis to promote term pregnancy by counteracting uterine stress and infection. In human PTL, choriodecidual B cells undergo aberrant expansion, increased activation and differentiation into plasma cells and B-1 cells, which might result from increased local expression of BAFF, APRIL and TSLP, and secrete antibodies to trigger downstream inflammatory cascades, such as complement and neutrophil activation. Furthermore, the protective axis involving IL-33, choriodecidual B cells and PIBF1 is defective in human PTL due to the aberrant downregulation of IL-33Rα on choriodecidual B cells. Therapeutic supplementation of PIBF1 is a viable strategy to prevent PTL. *: $p<0.05$; : $p<0.01$; *: $p<0.001$, by 2-tailed t-test (FIGS. 4A and 4J) or 2-tailed Mann-Whitney U test (FIGS. 4F and 4G).

Human choriodecidual B cells express PIBF1 at term delivery, see FIG. 6A which shows imaging flow cytometry analysis of PIBF1 expression by TL choriodecidual CD19+ B cells. Isotype control antibody-stained B cells were analyzed in parallel. DNA in the nuclei was counter-stained with Hoechst 33342. Arrow heads point to perinuclear PIBF1 staining concentrated at areas resembling centrosomes. Bar: 7 µm.

FIG. 7A shows the flow cytometric gating strategy for the identification of mouse uterine B cells, T cells, NK cells, NKT cells, macrophages, DCs, neutrophils and CD45-resident cells. FIG. 7B shows expression of PIBF1 and IL-10 by mouse uterine viable T cells, B cells, NK cells, NKT cells, neutrophils, DCs, macrophages and CD45-resident cells on gd 16.5. The quadrants were drawn based on the staining with isotype control antibodies. FIGS. 7C and 7D show statistical comparisons of the frequencies of PIBF1+ cells and ratios of mean fluorescence intensity (MFI) of PIBF1 to isotype control staining of the various uterine cell populations to that of B cells. *: $p<0.05$; : $p<0.01$; : $p<0.001$, by 2-tailed t-test. Data represent the results from 4 C57BL/6 mice at each time point.

FIG. 8A shows the flow cytometric gating strategy for the identification of human choriodecidual B cells, CD4+, CD8+ and CD4−CD8− T cells, CD16+ and CD56+NK cells, CD16− monocytes and CDI6+ monocytes/macrophages, CD15+CD16+ neutrophils and CD45− resident non-hematopoietic cells. FIG. 8B shows expression of PIBF1 by human choriodecidual viable B cells, CD4+, CD8+ and CD4-CD8− T cells, CD16+ and CD56+NK cells, CD16− monocytes and CD16+ monocytes/macrophages, CD15+CD16+ neutrophils and CD45− resident non-hematopoietic cells at term delivery. The gates were drawn based on the staining with an isotype control antibody. FIGS. 8C and 8D show statistical comparisons of the frequencies of PIBF1+ cells and ratios of mean fluorescence intensity (MFI) of PIBF1 to isotype control staining of the various choriodecidual cell populations to that of B cells. *: p<0.05; **: p<0.01, by 2-tailed t-test. FIG. 8E shows Western Blot analysis of PIBF1 expression by PBMCs, PBMCs depleted of CD19+ B cells and CD19+ B cells of a representative healthy donor. Data in FIGS. 8C and 8D represent the results of 5 subjects. Data in FIG. 8E represent the results of cells from 4 donors.

FIG. 9A shows fold change of Il1b, Cxcl10, Ccl3, Cxcl1, Ccl2 and Cxcl9 transcripts in uterine tissues of gd 17.5 CpMT mice after receiving 1 μg fPIBF1 and 5 μg LPS, relative to the gene transcripts in uterine tissues of the respective mice that received 1 μg fPIBF1 but not LPS. FIG. 9B shows expression of surface ICAM-1, MHC-II, CD86, CD44 and CD95 by viable neutrophils in uterine tissues of a representative μMT mouse 24 hours after receiving PBS and 5 μg LPS or 1 μg fPIBF1 and 5 μg LPS. Shaded histograms indicate the staining with isotype control antibodies. Data represent the results of 9 mice per group.

FIG. 10A shows Western Blot analysis of fPIBF1 and cPIBF1 using a C-terminus-specific and an N-terminus-specific antibody. FIGS. 10B and 10C show rates of preterm delivery and neonatal/fetal mortality on gd 17.5 of μMT mice that received either intravenous PBS or 300 ng C-terminal fragment of PIBF1 (cPIBF1) and 5 μg intraperitoneal LPS on gd 16.5. FIGS. 10D and 10E show frequency of CD11b+Ly-6G+ neutrophils in CD45+ cells in uterine tissues of gd 17.5 μMT mice after receiving either intravenous PBS or C-terminal PIBF1 and intraperitoneal LPS on gd 16.5. FIG. 10F shows expression of surface CD11b, CD18, CD62L, ICAM-1, MHC-II, CD86, CD44, CD95 and intracellular iNOS by viable neutrophils in uterine tissues of a representative piMT mouse 24 hours after receiving intravenous PBS or cPIBF1 and intraperitoneal LPS. Data represent the results from 9 mice per group. *: p<0.05; : p<0.01; *: p<0.001, by Fisher's exact test (FIG. 10A), 1-tailed Mann-Whitney U test (FIG. 10B), or 1-tailed t-test (FIG. 10D).

FIG. 11A shows fold change of PIBF1 transcript in purified human peripheral blood IgD+B cells after 2 days of treatment with medium (control), 100 ng/ml IFN-γ, TNF, IL-17A, IL-4 or IL-10, 1 ng/ml TGF-β, 100 ng/ml IL-25, TSLP, IL-33 or 1 μM progesterone. : p<0.01; *: p<0.001, by 2-tailed t-test. FIG. 11A shows flow cytometric analysis of the expression of the IL-25 receptor subunit IL-17RB and TSLP receptor (TSLPR) on peripheral blood, TL and PTL choriodecidual B cells. Data in FIG. 11A are representative of 3 independent experiments. Data in FIG. 11B represent the results of 10 blood donors, 10 women with TL and 10 women with PTL.

FIG. 12A shows a schematic representation of the disruption of the IL-33 locus in the IL-33−/− lacZ reporter mouse. The targeting vector IL-33Tm1a contains an En2/IRES/LacZ/Neo/pA cassette preceding exons 5-7 of the IL-33 gene that are flanked by LoxP sites. This targeting vector was introduced into the C57BL/6 mouse ES cell line B6-13. The IL-33tm1b allele was generated by breeding IL-33tm1a mice with CMV-Cre transgenic mice of the C57BL/6 background, resulting in the deletion of exons 5-7 and the Neo cassette. The Cre transgene was subsequently bred out. SA: splicing acceptor. FIG. 12B shows flow cytometry of PIBF1 expression in uterine cells of a pregnant IL-33−/− mice on gd 16.5. FIGS. 12C and 12D show statistical comparisons of the frequencies of PIBF1+ uterine B cells and ratios of MFI of PIBF1 to isotype control staining of uterine B cells of pregnant WT and IL-33−/− mice on gd 16.5. **: p<0.01, by 2-tailed t-test. Data represent the results of 3 mice in each group.

FIG. 13A shows flow cytometric analysis of the expression of IL1RAcP on peripheral blood, TL and PTL choriodecidual B cells. Results represent 24 healthy blood donors, 14 women with TL and 12 women with PTL. Shaded histograms indicate the staining with an isotype control antibody. FIGS. 13B, and 13C show statistical comparison of the frequencies of IL1RAcP+ B cells and the ratios of MFI of IL1RAcP to isotype control staining of B cells in peripheral blood (n=24), TL choriodecidua (n=14) and PTL choriodecidua (n=12). *: p<0.05; : p<0.01; *: p<0.001, by 2-tailed Mann-Whitney U test (for Term vs. PB and Preterm vs. PB in FIG. 13B) or 2-tailed t-test (all other comparisons).

FIG. 14A shows flow cytometric analysis of the frequency of CD11b+Ly-6G+ neutrophils in CD45+ cells in uterine tissues of representative WT and μMT mice 24 hours after receiving 0, 2.5, 10 or 20 μg LPS. FIG. 14B shows statistical comparison of the frequencies of neutrophils in uterine CD45+ leukocytes in WT and μMT mice after receiving 0, 2.5, 5, 10 or 20 μg LPS. *: p<0.05; ***: p<0.001, by 2-tailed t-test. FIG. 14C shows expression of surface ICAM-1, MHC-II, CD86, CD44 and CD95 by viable neutrophils in uterine tissues of a representative WT or μMT mouse 24 hours after receiving 5 μg LPS. Data in FIGS. 14A and 14B represent the results of 3 WT mice (PBS group), 4 WT mice (20 μg LPS group), 5 WT mice (0.5 and 10 μg LPS groups), 6 WT mice (2.5 μg LPS group), 7 WT mice (5 μg LPS group), 4 μMT mice (2.5 and 20 μg LPS groups), 5 μMT mice (10 μg LPS group), 6 μMT mice (PBS and 0.5 μg LPS groups) or 9 μMT mice (5 μg LPS group) per group. Data in FIG. 14C represent the results of 7 WT mice and 9 μMT mice.

DETAILED DESCRIPTION OF THE INVENTION

Figures 1A, 1B, 1C:
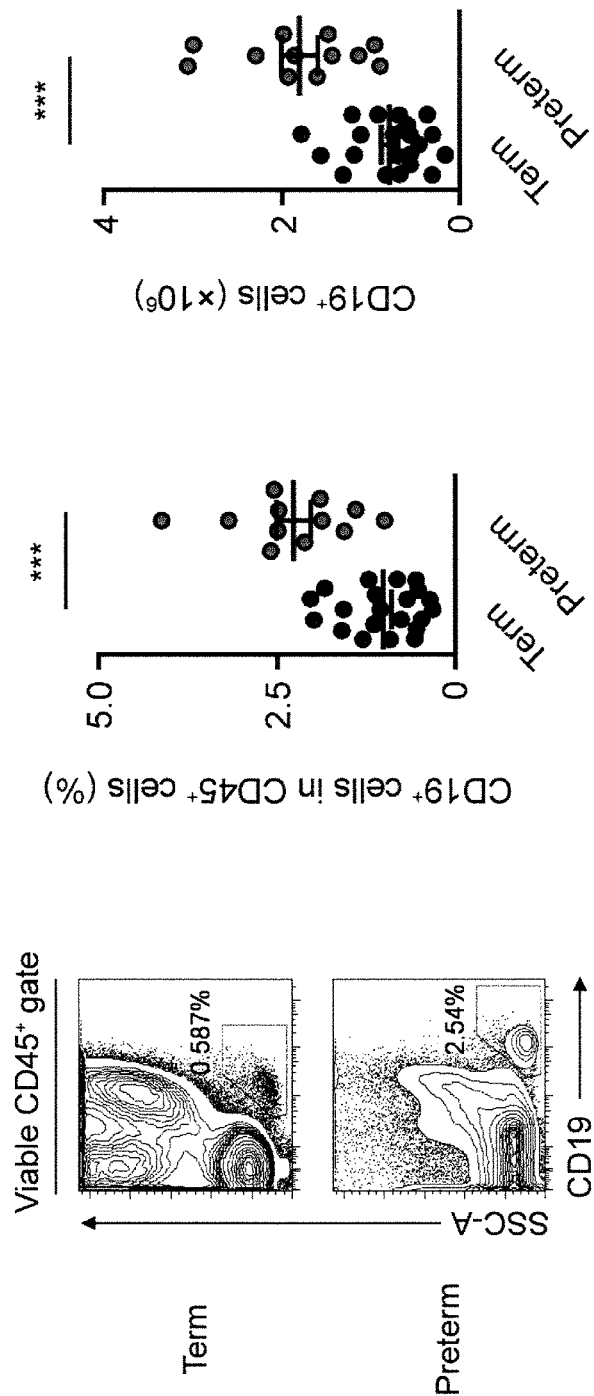
FIGS. 1A, 1B, and 1C generally show that human choriodecidua harbors B cells that are dysregulated in preterm labor (PTL).

Described are compositions and methods of the present invention generally relating to prevention and/or inhibition of preterm labor in a pregnant subject. In specific embodiments, compositions and methods described herein relate to progesterone-induced blocking factor 1 (PIBF1), interleukin-33 (IL-33), and variants of either thereof, and their use in preventing and/or inhibition of preterm labor in a pregnant subject.

Methods relating to prevention and/or inhibition of preterm labor in a pregnant subject in need thereof are provided according to aspects of the present invention which include administering a therapeutically effective amount of progesterone-induced blocking factor 1 (PIBF1), IL-33, a PIBF1 variant, an IL-33 variant or a combination of any two or more thereof are provided according to embodiments of the present invention.

The term "preterm labor" refers to spontaneous uterine contractions of sufficient frequency and intensity to effect progressive effacement and dilation of the cervix prior to term gestation, i.e. at or before 37 weeks of gestation in humans. The phrases "inhibiting preterm labor," "inhibit preterm labor" and "inhibition of preterm labor" refer to reduction of preterm labor or cessation of preterm labor in a pregnant subject having preterm labor. The phrase, "preventing preterm labor," "prevent preterm labor," and "prevention of preterm labor" refer to treatment of a pregnant subject susceptible to preterm labor to avoid preterm labor in the susceptible pregnant subject.

A pregnant subject undergoing, or susceptible to, preterm labor can be identified by a medical professional using standard medical assessment techniques.

According to aspects of the invention, compositions and methods are provided to prevent and/or inhibit preterm labor associated with inflammation and/or infection in the pregnant subject.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Remington: The Science and Practice of Pharmacy, Lippincott Williams & Wilkins, 21st Ed., 2005; L. V. Allen, Jr. et al., Ansel's Pharmaceutical Dosage Forms and Drug Delivery Systems, 8th Ed., Philadelphia, Pa.: Lippincott, Williams & Wilkins, 2004; and L. Brunton et al., Goodman & Gilman's The Pharmacological Basis of Therapeutics, McGraw-Hill Professional, 12th Ed., 2011.

The singular terms "a," "an," and "the" are not intended to be limiting and include plural referents unless explicitly stated otherwise or the context clearly indicates otherwise.

PIBF1 is a well-known protein encoded by the PIBF1 gene in humans. Orthologs are known in mice as well as other species.

The term "PIBF1" refers to a PIBF1 protein which prevents and/or inhibits preterm labor in a pregnant subject, disclosed herein as SEQ ID NO: 1 and PIBF orthologs from any species which prevent and/or inhibit preterm labor in a pregnant subject. The term "PIBF1 variant" refers to a PIBF1 peptide or protein effective to prevent and/or inhibit preterm labor in a pregnant subject and which includes an alteration, i.e. a substitution, insertion or deletion, of one or more amino acids compared to the full-length amino acid sequence of SEQ ID NO: 1.

As will be readily apparent to one of skill in the art, due to the redundancy of the genetic code, more than one nucleic acid sequence encodes PIBF1 of SEQ ID NO: 1.

The term "PIBF1 variant" refers to both naturally occurring variations of a given PIBF1 protein and recombinantly prepared mutations of a given PIBF1 protein, as well as PIBF1 functional fragments, wherein the variant is effective to prevent and/or inhibit preterm labor in a pregnant subject. PIBF1 variants of human PIBF1 have at least 80%, or at least 85%, 86%, 87%, 88%, 89%, 90%, 91%, 92%, 93%, 94%, 95%, 96%, 97%, 98%, 99%, or greater, amino acid sequence identity to full length human PIBF1 of SEQ ID NO:1, wherein the variant is effective to prevent and/or inhibit preterm labor in a pregnant subject according to aspects of the present invention.

A functional fragment of PIBF1 is a portion of a full-length PIBF1 which is effective to prevent and/or inhibit preterm labor in a pregnant subject according to aspects of the present invention. According to aspects of the present invention, a functional fragment of PIBF1 effective to prevent and/or inhibit preterm labor in a pregnant subject includes amino acids 1-659 of SEQ ID NO:1, amino acids 1-600 of SEQ ID NO:1, amino acids 1-550 of SEQ ID NO:1, amino acids 1-500 of SEQ ID NO:1, amino acids 1-450 of SEQ ID NO:1, amino acids 1-400 of SEQ ID NO:1, amino acids 1-350 of SEQ ID NO:1, amino acids 1-300 of SEQ ID NO:1, amino acids 1-250 of SEQ ID NO:1, amino acids 1-200 of SEQ ID NO:1, or amino acids 1-100 of SEQ ID NO:1.

According to aspects of the present invention, a functional fragment of PIBF1 effective to prevent and/or inhibit preterm labor in a pregnant subject includes amino acids 100-659 of SEQ ID NO: 1, amino acids 200-600 of SEQ ID NO: 1, amino acids 200-500 of SEQ ID NO:1, amino acids 200-400 of SEQ ID NO:1, amino acids 100-450 of SEQ ID NO:1, amino acids 100-400 of SEQ ID NO:1, amino acids 100-300 of SEQ ID NO:1, amino acids 100-200 of SEQ ID NO:1, amino acids 300-450 of SEQ ID NO:1, amino acids 300-400 of SEQ ID NO:1, or amino acids 400-659 of SEQ ID NO: 1.

For example, a functional fragment of PIBF1 effective to prevent and/or inhibit preterm labor in a pregnant subject is disclosed herein as SEQ ID NO:2.

In a further example, a functional fragment of PIBF1 effective to prevent and/or inhibit preterm labor in a pregnant subject is disclosed herein as SEQ ID NO:9

PIBF1 functional fragment of SEQ ID NO: 2 is encoded by SEQ ID NO:4.

PIBF1 functional fragment of SEQ ID NO: 9 is encoded by SEQ ID NO:10.

In a further example, a functional fragment of PIBF1 effective to prevent and/or inhibit preterm labor in a pregnant subject is a protein having at least 80%, or at least 85%, 86%, 87%, 88%, 89%, 90%, 91%, 92%, 93%, 94%, 95%, 96%, 97%, 98%, 99%, or greater, amino acid sequence identity to the 659 amino acid fragment of SEQ ID NO:2 or the 419 amino acid fragment of SEQ ID NO:9.

A PIBF1 variant can be encoded by a nucleic acid sequence having substantial similarity to nucleic acid sequences encoding human PIBF1 of SEQ ID NO:1, the fragment SEQ ID NO:2 or the fragment SEQ ID NO:9 disclosed herein. A nucleic acid sequence having substantial similarity to a nucleic acid sequence SEQ ID NO:3, SEQ ID NO:4 or SEQ ID NO:10 encoding a PIBF1 variant and effective to prevent and/or inhibit preterm labor in a pregnant subject has at least 70%, at least 75%, or at least 85%, 90%, 91%, 92%, 93%, 94%, 95%, 96%, 97%, 98%, 99%, or greater, nucleic acid sequence identity to SEQ ID NO:3, SEQ ID NO:4 or SEQ ID NO:10.

In embodiments of the present invention, a substantially similar nucleic acid sequence is characterized as having a complementary nucleic acid sequence capable of hybridizing to a nucleic acid sequence encoding PIBF1 or a functional fragment thereof under high stringency hybridization conditions.

Interleukin 33 (IL-33) is a well-known protein encoded by the IL33 gene in humans. Orthologs are known in mice as well as other species.

The term "IL-33" refers to an IL-33 protein which prevents and/or inhibits preterm labor in a pregnant subject, disclosed herein as SEQ ID NO: 5, and IL-33 orthologs from any species which prevent and/or inhibit preterm labor in a pregnant subject, such as SEQ ID NO: 6.

Human IL-33 is disclosed herein as SEQ ID NO: 5:
Mouse IL-33 is disclosed herein as SEQ ID NO: 6:

The term "IL-33 variant" refers to a peptide or protein effective to prevent and/or inhibit preterm labor in a pregnant subject and which includes an alteration, i.e. a substitution, insertion or deletion, of one or more amino acids compared to the full-length amino acid sequence of SEQ ID NO:5.

The term "IL-33 variant" refers to both naturally occurring variations of a given IL-33 protein and recombinantly prepared mutations of a given IL-33 protein, as well as IL-33 functional fragments, wherein the variant is effective to prevent and/or inhibit preterm labor in a pregnant subject. A functional fragment of IL-33 is a portion of a full-length IL-33 which is effective to prevent and/or inhibit preterm labor in a pregnant subject according to aspects of the present invention.

The term "IL-33 variant" refers to a protein characterized by an amino acid sequence substantially similar to the full length amino acid sequence of human IL-33 (SEQ ID NO: 5) effective to prevent and/or inhibit preterm labor in a pregnant subject compared to human IL-33 as well as a protein characterized by an amino acid sequence substantially similar to the full length amino acid sequence of mouse IL-33 (SEQ ID NO: 6) effective to prevent and/or inhibit preterm labor in a pregnant subject compared to mouse IL-33. IL-33 variants of human IL-33 have at least 80%, or at least 85%, 90%, 91%, 92%, 93%, 94%, 95%, 96%, 97%, 98%, 99%, or greater, amino acid sequence identity to full length human IL-33 of SEQ ID NO:5. IL-33 variants of mouse IL-33 have at least 80%, or at least 85%, 86%, 87%, 88%, 89%, 90%, 91%, 92%, 93%, 94%, 95%, 96%, 97%, 98%, 99%, or greater, amino acid sequence identity to full length mouse IL-33 of SEQ ID NO:6.

IL-33 variants have at least 80%, or at least 85%, 86%, 87%, 88%, 89%, 90%, 91%, 92%, 93%, 94%, 95%, 96%, 97%, 98%, 99%, or greater, amino acid sequence identity to full length human PIBF1 of SEQ ID NO:5 or full-length mouse IL-33 of SEQ ID NO:6 according to aspects of the present invention.

IL-33 of SEQ ID NO: 5 is encoded by SEQ ID NO:7.
IL-33 of SEQ ID NO: 6 is encoded by SEQ ID NO:8.

As will be readily apparent to one of skill in the art, due to the redundancy of the genetic code, more than one nucleic acid sequence encodes IL-33 of SEQ ID NO:5 or SEQ ID NO:6.

An IL-33 variant can be encoded by a nucleic acid sequence having substantial similarity to nucleic acid sequences encoding human IL-33 of SEQ ID NO:5 or mouse IL-33 of SEQ ID NO:6. A nucleic acid sequence having substantial similarity to a nucleic acid sequence SEQ ID NO:7 or SEQ ID NO:8 has at least 70%, at least 75%, or at least 85%, 90%, 91%, 92%, 93%, 94%, 95%, 96%, 97%, 98%, 99%, or greater, nucleic acid sequence identity to SEQ ID NO:7 or SEQ ID NO:8.

In embodiments of the present invention, a substantially similar nucleic acid sequence is characterized as having a complementary nucleic acid sequence capable of hybridizing to a nucleic acid sequence encoding IL-33 or a functional fragment thereof under high stringency hybridization conditions.

The term "nucleic acid" as used herein refers to RNA or DNA molecules having more than one nucleotide in any form including single-stranded, double-stranded, oligonucleotide or polynucleotide. The term "nucleotide sequence" is used to refer to the ordering of nucleotides in an oligonucleotide or polynucleotide in a single-stranded form of nucleic acid.

The term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" to a specified second nucleotide sequence. For example, a nucleotide sequence may have 80%, 90%, or 100%/complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100/complementary to the nucleotide sequence 5'-AGCT-3'. Further, the nucleotide sequence 3'-TCGA- is 100% complementary to a region of the nucleotide sequence 5'-TTAGCTGG-3'.

The terms "hybridization" and "hybridizes" refer to pairing and binding of complementary nucleic acids. Hybridization occurs to varying extents between two nucleic acids depending on factors such as the degree of complementarity of the nucleic acids, the melting temperature, Tm, of the nucleic acids and the stringency of hybridization conditions, as is well known in the art. The term "stringency of hybridization conditions" refers to conditions of temperature, ionic strength, and composition of a hybridization medium with respect to particular common additives such as formamide and Denhardt's solution. Determination of particular hybridization conditions relating to a specified nucleic acid is routine and is well known in the art, for instance, as described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002. High stringency hybridization conditions are those which only allow hybridization of substantially complementary nucleic acids. Typically, nucleic acids having about 85-1000/complementarity are considered highly complementary and hybridize under high stringency conditions. Intermediate stringency conditions are exemplified by conditions under which nucleic acids having intermediate complementarity, about 50-84% complementarity, as well as those having a high degree of complementarity, hybridize. In contrast, low stringency hybridization conditions are those in which nucleic acids having a low degree of complementarity hybridize.

The terms "specific hybridization" and "specifically hybridizes" refer to hybridization of a particular nucleic acid to a target nucleic acid without substantial hybridization to nucleic acids other than the target nucleic acid in a sample.

Stringency of hybridization and washing conditions depends on several factors, including the Tm of the probe and target and ionic strength of the hybridization and wash conditions, as is well-known to the skilled artisan. Hybridization and conditions to achieve a desired hybridization stringency are described, for example, in Sambrook et al., Molecular Cloning: A Laboratory Manual, Cold Spring Harbor Laboratory Press, 2001; and Ausubel, F. et al., (Eds.), Short Protocols in Molecular Biology, Wiley, 2002.

An example of high stringency hybridization conditions is hybridization of nucleic acids over about 100 nucleotides in length in a solution containing 6×SSC, 5×Denhardt's solution, 30% formamide, and 100 micrograms/ml denatured salmon sperm at 37° C. overnight followed by washing in a solution of 0.1×SSC and 0.1% SDS at 60° C. for 15 minutes. SSC is 0.15M NaCl/0.015M Na citrate. Denhardt's solution is 0.02% bovine serum albumin/0.02% FICOLL/0.02% polyvinylpyrrolidone. Under highly stringent conditions SEQ ID NOs. 3, 7, 8 and 10 will each hybridize to the complement of substantially identical targets and not to unrelated sequences.

Mutations can be introduced using standard molecular biology techniques, such as site-directed mutagenesis and PCR-mediated mutagenesis. One of skill in the art will recognize that one or more amino acid mutations can be introduced without altering the functional properties of PIBF1 and/or IL-33. For example, one or more amino acid substitutions, additions, or deletions can be made without altering the functional properties of PIBF1 and/or IL-33.

Conservative amino acid substitutions can be made in PIBF1 and/or IL-33 proteins to produce PIBF1 and/or IL-33 variants. Conservative amino acid substitutions are art recognized substitutions of one amino acid for another amino acid having similar characteristics. For example, each amino acid may be described as having one or more of the following characteristics: electropositive, electronegative, aliphatic, aromatic, polar, hydrophobic and hydrophilic. A conservative substitution is a substitution of one amino acid having a specified structural or functional characteristic for another amino acid having the same characteristic. Acidic amino acids include aspartate, glutamate; basic amino acids include histidine, lysine, arginine; aliphatic amino acids include isoleucine, leucine and valine; aromatic amino acids include phenylalanine, histidine, tyrosine and tryptophan; polar amino acids include aspartate, glutamate, histidine, lysine, asparagine, glutamine, arginine, serine, threonine and tyrosine; and hydrophobic amino acids include alanine, cysteine, phenylalanine, glycine, isoleucine, leucine, methionine, proline, valine and tryptophan; and conservative substitutions include substitution among amino acids within each group. Amino acids may also be described in terms of relative size, alanine, cysteine, aspartate, glycine, asparagine, proline, threonine, serine, valine, all typically considered to be small.

Variants according to aspects of the present invention can include synthetic amino acid analogs, amino acid derivatives and/or non-standard amino acids, illustratively including, without limitation, alpha-aminobutyric acid, citrulline, canavanine, cyanoalanine, diaminobutyric acid, diaminopimelic acid, dihydroxy-phenylalanine, djenkolic acid, homoarginine, hydroxyproline, norleucine, norvaline, 3-phosphoserine, homoserine, 5-hydroxytryptophan, 1-methylhistidine, 3-methylhistidine, and ornithine.

Embodiments of methods and compositions of the present invention include PIBF1 proteins having at least 85%, 86%, 87%, 88%, 89%, 90%, 91%, 92%, 93%, 94%, 95%, 96%, 97%, 98% or 99% amino acid sequence identity to SEQ ID NO: 1, SEQ ID NO:2 or SEQ ID NO:9.

Embodiments of methods and compositions of the present invention include IL-33 proteins having at least 85%, 86%, 87%, 88%, 89%, 90%, 91%, 92%, 93%, 94%, 95%, 96%, 97%, 98% or 99% amino acid sequence identity to SEQ ID NO:5 or SEQ ID NO:6.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions X100%). In one embodiment, the two sequences are the same length. Alternatively, the two sequences may be different lengths, such as 1, 2, 3, 4, 5, 6, 7, 8, 9 or 10 amino acids different in length. The additions or deletions may be at the N-terminus, C-terminus, internally or a mixture of any thereof.

The determination of percent identity between two sequences can also be accomplished using a mathematical algorithm. A preferred, non-limiting example of a mathematical algorithm utilized for the comparison of two sequences is the algorithm of Karlin and Altschul, 1990, PNAS 87:2264 2268, modified as in Karlin and Altschul, 1993, PNAS. 90:5873 5877. Such an algorithm is incorporated into the NBLAST and XBLAST programs of Altschul et al., 1990, J. Mol. Biol. 215:403. BLAST nucleotide searches are performed with the NBLAST nucleotide program parameters set, e.g., for score=100, wordlength=12 to obtain nucleotide sequences homologous to a nucleic acid molecules of the present invention. BLAST protein searches are performed with the XBLAST program parameters set, e.g., to score 50, wordlength=3 to obtain amino acid sequences homologous to a protein molecule of the present invention. To obtain gapped alignments for comparison purposes, Gapped BLAST are utilized as described in Altschul et al., 1997, Nucleic Acids Res. 25:3389 3402. Alternatively, PSI BLAST is used to perform an iterated search which detects distant relationships between molecules. When utilizing BLAST, Gapped BLAST, and PSI Blast programs, the default parameters of the respective programs (e.g., of XBLAST and NBLAST) are used. Another preferred, non-limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 is used.

The percent identity between two sequences is determined using techniques similar to those described above, with or without allowing gaps. In calculating percent identity, typically only exact matches are counted.

PIBF1, PIBF1 variants, IL-33 and IL-33 variants can be produced in recombinant host cells using well-known conventional techniques. Broadly described, a nucleic acid molecule encoding PIBF1, a PIBF1 variant, IL-33 or an IL-33 variant is operably linked to regulatory sequences that control transcriptional expression in an expression vector. The expression vector is introduced into a host cell where it is expressed and the PIBF1, PIBF1 variant, IL-33 or IL-33 variant can then be isolated.

An expression vector including a nucleic acid encoding PIBF1, a PIBF1 variant, IL-33 or an IL-33 variant is administered to a subject to prevent and/or inhibit preterm labor according to embodiments of the present invention.

Non-limiting examples of regulatory sequences that control transcriptional expression in an expression vector illustratively include a promoter, an enhancer, a splicing signal, a transcription start site, a transcription termination signal, a polyadenylation signal, an internal ribosome entry site (IRES) and combinations of these or other regulatory sequences. A secretory sequence encoding a secretion signal that directs an encoded heterologous protein into the secretory pathway of a host cell is optionally included. Additional sequences optionally included in an expression vector include one or more sequences encoding a marker suitable for selection of cells carrying the expression vector.

Viral expression vectors can be used to express a desired protein. Non-limiting examples of virus expression systems include adenovirus, adeno-associated virus, herpes virus, vaccinia virus and lentivirus.

A host cell for expression of PIBF1, a PIBF1 variant, IL-33 or an IL-33 variant can be prokaryotic or eukaryotic, such as bacterial, plant, insect, fungus, yeast, and mammalian cells.

According to aspects of the present invention, the host cell is in vivo, such as in a human so that the PIBF1, a PIBF1 variant, IL-33 or an IL-33 variant is expressed in the host and prevents and/or inhibits preterm labor in a pregnant host.

An expression vector is introduced into a host cell using well-known techniques such as infection or transfection, including calcium phosphate transfection, liposome-mediated transfection, electroporation and sonoporation. Expression constructs and methods for their generation and use to express a desired protein are known in the art, as described, for example, in Sambrook et al., Molecular Cloning: A Laboratory Manual, Cold Spring Harbor Laboratory Press, 2001; Ausubel, F. et al., (Eds.), Short Protocols in Molecular Biology, Wiley, 2002; and S. J. Higgins and B. D. Hames (Eds.), Protein Expression: A Practical Approach, Oxford University Press, USA, 1999.

In addition to recombinant methodology, chemical synthetic techniques can be used to produce PIBF1, a PIBF1 variant, IL-33 or an IL-33 variant. For example, PIBF1, a PIBF1 variant, IL-33 or an IL-33 variant can be produced using solid phase synthesis, solution phase synthesis, partial solid phase synthesis or fragment condensation.

The term "isolated" as used herein refers to a substance that has been separated from contaminating cellular components associated with the substance in nature not intended to be associated with the substance and that would interfere with use of the substance in therapeutic, prophylactic, diagnostic or other uses. Generally, an isolated substance described herein is at least about 80% pure, at least about 90% pure, at least about 95% pure, or greater than about 99% pure. Purification is achieved using well-known standard methodology such as fractionation and/or chromatography, such as ammonium sulfate precipitation and elution chromatography such as size exclusion chromatography, displacement chromatography, ion exchange chromatography and bioaffinity chromatography. Exemplary purification methodology is described in S. Doonan, Protein Purification Protocols Humana Press, 1996.

In embodiments of the present invention, isolated PIBF1, a PIBF1 variant, IL-33 or an IL-33 variant is administered to a subject and/or included in a composition of the present invention.

A substance effective to increase PIBF1 and/or produce a therapeutic effect of PIBF1 in a subject is administered to a pregnant subject in need of prevention and/or inhibition of preterm labor according to embodiments of the present invention.

The terms "treating" and "treatment" used to refer to inhibition of preterm labor in a pregnant subject includes: inhibiting or stopping preterm labor in a pregnant subject, such as stopping or reducing uterine contractions. The terms "treating" and "treatment" used to refer to prevention of preterm labor in a pregnant subject includes: avoiding preterm labor in a pregnant subject susceptible to preterm labor, such as avoiding uterine contractions in the susceptible pregnant subject.

A subject treated to prevent and/or inhibit preterm labor according to methods and using compositions of the present invention can be a mammalian subject at risk of preterm labor. Humans are preferred subjects treated according to methods and using compositions of the present invention. A mammalian subject treated according to aspects of the present invention can be any mammal including, but not limited to, a non-human primate; a rodent such as a mouse, rat, or guinea pig; a domesticated pet such as a cat or dog; a horse, cow, pig, sheep, goat, or rabbit.

In a particular embodiment of the present invention a method of prevention and/or inhibition of preterm labor in a pregnant subject is provided which includes administering a therapeutically effective amount of PIBF1, a PIBF1 variant, IL-33 or an IL-33 variant to the subject.

A therapeutically effective amount is an amount which produces a desired physiologic or pharmacologic effect in a subject, specifically prevention and/or inhibition of preterm labor in a pregnant subject. For example, a therapeutically effective amount is an amount which prevents, reduces or eliminates preterm uterine contractions in a pregnant subject.

Suitable dosages ranges of PIBF1, a PIBF1 variant, IL-33 or an IL-33 variant depend on various factors such as the age of the subject, the extent of predisposition to preterm labor in the subject, the general condition of the subject, the route and form of administration of the composition being administered and the particular composition administered. One of ordinary skill in the art will be able to ascertain a therapeutically effective amount without undue experimentation in view of the present disclosure and what is known in the art.

Administration of PIBF1, a PIBF1 variant, IL-33 or an IL-33 variant according to embodiments of a method of the present invention includes administration according to a dosage regimen to produce a desired response. For example, one or more dosage units of PIBF1, a PIBF1 variant, IL-33 or an IL-33 variant is administered to a subject at one time in particular embodiments. A suitable schedule for administration of doses depends on several factors including age, weight, medical history and health status of the subject, type of composition used and route of administration, for example. One of skill in the art is able to readily determine a dose and schedule of administration for a particular subject.

According to particular aspects of the present invention, an administered amount of PIBF1, a PIBF1 variant, IL-33 or an IL-33 variant in the range of about 0.001 mg/kg body weight of the subject to about 100 mg/kg body weight of the subject, such as 0.001 mg/kg, 0.005 mg/kg, 0.01 mg/kg, 0.05 mg/kg, 0.1 mg/kg, 0.5 mg/kg, 1 mg/kg, 5 mg/kg, 10 mg/kg, 50 mg/kg, or 100 mg/kg is administered and will have therapeutic efficacy. The amount may be administered, for example, daily, twice daily, 3 times each day, 4 times each day, 6 times each day or more. The amount may be administered, for example, daily, every other day, every three days, weekly, biweekly or monthly. Duration of treatment is typically limited by the duration of the pregnancy.

PIBF1, a PIBF1 variant, IL-33 or an IL-33 variant may be administered by any of various routes of administration, for example, oral, rectal, nasal, pulmonary, epidural, ocular, otic, intraarterial, intracardiac, intracerebroventricular, intracranial, intradermal, intravenous, intramuscular, intraperitoneal, intraosseous, intrathecal, intravesical, subcutaneous, topical, transdermal, and transmucosal, such as by sublingual, buccal, vaginal, and inhalational routes of administration. According to particular aspects of the present invention, PIBF1, a PIBF1 variant, IL-33 or an IL-33 variant is administered intravenously.

Embodiments of the present invention optionally include administration of a therapeutic agent in addition to PIBF1, a PIBF1 variant, IL-33 or an IL-33 variant. Non-limiting examples of pharmacologically active agents administered in addition to PIBF1, a PIBF1 variant, IL-33 or an IL-33 variant in combination or separately, according to embodiments of methods of the present invention include, antibiotics, antivirals, antineoplastic agents, analgesics, antipyretics, antidepressants, antipsychotics, anticancer agents, antihistamines, anti-osteoporosis agents, anti-osteonecrosis agents, antiinflammatory agents, anxiolytics, chemotherapeutic agents, diuretics, growth factors, hormones, non-steroidal anti-inflammatory agents and vasoactive agents or a combination of any two or more thereof.

Embodiments of the present invention optionally include administration of a tocolytic agent in addition to PIBF1, a PIBF1 variant, IL-33 or an IL-33 variant. Examples of tocolytic agents that can be used in addition to PIBF1, a PIBF1 variant, IL-33 or an IL-33 variant include, but are not limited to, progesterone, magnesium sulfate, indomethacin and nifedipine.

A pharmaceutically acceptable carrier can be included in a composition including PIBF1, a PIBF1 variant, IL-33 or an IL-33 variant. A pharmaceutically acceptable carrier is substantially non-toxic to the subject in amounts administered and has substantially no deleterious effects on any active component of a composition in which it is included.

The PIBF1, PIBF1 variant, IL-33 or IL-33 variant to be administered is formulated for topical, local and/or systemic administration to the subject.

Methods according to embodiments of the present invention include administration of PIBF1, a PIBF1 variant, IL-33 or an IL-33 variant as pharmaceutical formulations, including those suitable for oral, rectal, nasal, pulmonary, epidural, ocular, otic, intraarterial, intracardiac, intracerebroventricular, intracranial, intradermal, intravenous, intramuscular, intraperitoneal, intraosseous, intrathecal, intravesical, subcutaneous, topical, transdermal, and transmucosal, such as by sublingual, buccal, vaginal, and inhalational routes of administration.

A pharmaceutical formulation of PIBF1, a PIBF1 variant, IL-33 or an IL-33 variant according to embodiments of the present invention is in any dosage form suitable for administration to a subject, illustratively including solid, semi-solid and liquid dosage forms such as tablets, capsules, powders, granules, suppositories, pills, solutions, suspensions, ointments, lotions, creams, gels, pastes, sprays and aerosols.

Liposomes and emulsions are well-known types of pharmaceutical formulations that can be used to deliver a pharmaceutical agent, particularly a hydrophobic pharmaceutical agent. In embodiments of the present invention, liposomes are particles typically produced as a unilammellar bilayer or a multilammellar bilayer of amphipathic molecules enclosing an aqueous interior. Liposomes can include any type of amphipathic materials compatible with a composition to be delivered, illustratively including naturally-occurring lipids, synthetic lipids and combinations thereof.

A pharmaceutical formulation of a composition of the present invention can include a pharmaceutically acceptable carrier. The term "pharmaceutically acceptable carrier" refers to a carrier which is suitable for use in a subject without undue toxicity or irritation to the subject and which is compatible with other ingredients included in a pharmaceutical composition. Pharmaceutically acceptable carriers, methods for making pharmaceutical compositions and various dosage forms, as well as modes of administration are well-known in the art, for example as detailed in Pharmaceutical Dosage Forms: Tablets, eds. H. A. Lieberman et al., New York: Marcel Dekker, Inc., 1989; and in L. V. Allen, Jr. et al., Ansel's Pharmaceutical Dosage Forms and Drug Delivery Systems, 8th Ed., Philadelphia, Pa.: Lippincott, Williams & Wilkins, 2004; A. R. Gennaro, Remington: The Science and Practice of Pharmacy, Lippincott Williams & Wilkins, 21st ed., 2005, particularly chapter 89; and J. G. Hardman et al., Goodman & Gilman's The Pharmacological Basis of Therapeutics, McGraw-Hill Professional, 10th ed., 2001.

A solid dosage form for administration or for suspension in a liquid prior to administration illustratively includes capsules, tablets, powders, and granules. In such solid dosage forms, one or more active agents, is admixed with at least one carrier illustratively including a buffer such as, for example, sodium citrate or an alkali metal phosphate illustratively including sodium phosphates, potassium phosphates and calcium phosphates; a filler such as, for example, starch, lactose, sucrose, glucose, mannitol, and silicic acid; a binder such as, for example, carboxymethylcellulose, alignates, gelatin, polyvinylpyrrolidone, sucrose, and acacia; a humectant such as, for example, glycerol; a disintegrating agent such as, for example, agar-agar, calcium carbonate, plant starches such as potato or tapioca starch, alginic acid, certain complex silicates, and sodium carbonate; a solution retarder such as, for example, paraffin; an absorption accelerator such as, for example, a quaternary ammonium compound; a wetting agent such as, for example, cetyl alcohol, glycerol monostearate, and a glycol; an adsorbent such as, for example, kaolin and bentonite; a lubricant such as, for example, talc, calcium stearate, magnesium stearate, a solid polyethylene glycol or sodium lauryl sulfate; a preservative such as an antibacterial agent and an antifungal agent, including for example, sorbic acid, gentamycin and phenol; and a stabilizer such as, for example, sucrose, EDTA, EGTA, and an antioxidant.

Solid dosage forms optionally include a coating such as an enteric coating. The enteric coating is typically a polymeric material. Preferred enteric coating materials have the characteristics of being bioerodible, gradually hydrolyzable and/or gradually water-soluble polymers. The amount of coating material applied to a solid dosage generally dictates the time interval between ingestion and drug release. A coating is applied having a thickness such that the entire coating does not dissolve in the gastrointestinal fluids at pH below 3 associated with stomach acids, yet dissolves above pH 3 in the small intestine environment. It is expected that any anionic polymer exhibiting a pH-dependent solubility profile is readily used as an enteric coating in the practice of the present invention to achieve delivery of the active agent to the lower gastrointestinal tract. The selection of the specific enteric coating material depends on properties such as resistance to disintegration in the stomach; impermeability to gastric fluids and active agent diffusion while in the stomach; ability to dissipate at the target intestine site; physical and chemical stability during storage; non-toxicity; and ease of application.

Suitable enteric coating materials illustratively include cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, preferably formed from acrylic acid, methacrylic acid, methyl acrylate, ammonium methylacrylate, ethyl acrylate, methyl methacrylate and/or ethyl; vinyl polymers and copolymers such as polyvinyl pyrrolidone, polyvinyl acetate, polyvinylacetate phthalate, vinylacetate crotonic acid copolymer, and ethylene-vinyl acetate copolymers; shellac; and combinations thereof. A particular enteric coating material includes acrylic acid polymers and copolymers described for example U.S. Pat. No. 6,136,345.

The enteric coating optionally contains a plasticizer to prevent the formation of pores and cracks that allow the penetration of the gastric fluids into the solid dosage form. Suitable plasticizers illustratively include: triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, a coating composed of an anionic carboxylic acrylic polymer typically contains approximately 10% to 25% by weight of a plasticizer, particularly dibutyl phthalate, polyethylene glycol, triethyl citrate and triacetin. The coating can also contain other coating excipients such as detackifiers, antifoaming agents, lubricants (e.g., magnesium stearate), and stabilizers (e.g. hydroxypropylcellulose, acids or bases) to solubilize or disperse the coating material, and to improve coating performance and the coated product.

Liquid dosage forms for oral administration include one or more active agents and a pharmaceutically acceptable carrier formulated as an emulsion, solution, suspension, syrup, or elixir. A liquid dosage form of a composition of the present invention may include a colorant, a stabilizer, a wetting agent, an emulsifying agent, a suspending agent, a sweetener, a flavoring, or a perfuming agent.

For example, a composition for parenteral administration may be formulated as an injectable liquid. Examples of suitable aqueous and nonaqueous carriers include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of a desirable particle size in the case of dispersions, and/or by the use of a surfactant, such as sodium lauryl sulfate. A stabilizer is optionally included such as, for example, sucrose, EDTA, EGTA, and an antioxidant.

For topical administration, a composition can be formulated for administration to the skin such as for local effect, and/or as a "patch" formulation for transdermal delivery. Pharmaceutical formulations suitable for topical administration include, for example, ointments, lotions, creams, gels, pastes, sprays and powders. Ointments, lotions, creams, gels and pastes can include, in addition to one or more active agents, a base such as an absorption base, water-removable base, water-soluble base or oleaginous base and excipients such as a thickening agent, a gelling agent, a colorant, a stabilizer, an emulsifying agent, a suspending agent, a sweetener, a flavoring, or a perfuming agent.

Transdermal formulations can include percutaneous absorption enhancers such as acetone, dimethyl acetamide, dimethyl formamide, dimethyl sulfoxide, ethanol, oleic acid, polyethylene glycol, propylene glycol and sodium lauryl sulfate. Ionotophoresis and/or sonophoresis can be used to enhance transdermal delivery.

Powders and sprays for topical administration of one or more active agents can include excipients such as talc, lactose and one or more silicic acids. Sprays can include a pharmaceutical propellant such as a fluorinated hydrocarbon propellant, carbon dioxide, or a suitable gas. Alternatively, a spray can be delivered from a pump-style spray device which does not require a propellant. A spray device delivers a metered dose of a composition contained therein, for example, using a valve for regulation of a delivered amount.

Ophthalmic formulations of one or more active agents can include ingredients such as a preservative, a buffer and a thickening agent.

Embodiments of inventive compositions and methods are illustrated in the following examples. These examples are provided for illustrative purposes and are not considered limitations on the scope of inventive compositions and methods.

Examples

Tnf: tumor necrosis factor; Mmp9: matrix metalloprotease 9; Cxcl2: C-X-C chemokine ligand 2; Cxcl3: C-X-C chemokine ligand 3; Cxcl5: C-X-C chemokine ligand 5; Il1b: interleukin-1 beta; Cxcl1: C-X-C chemokine ligand 1; Gapdh: glyceraldehyde-3-phosphate dehydrogenase. ILx is an abbreviation for interleukin-x such as for example, Il6: interleukin-6;

Study Subjects

Women who underwent spontaneous TL (37 to 41 weeks of gestation) or spontaneous PTL (between 32 to 37 weeks of gestation) (Table 1) were enrolled into this study. Subjects with non-singleton gestation, current diagnosis of preeclampsia, a prior history or current diagnosis of diabetes, chronic hypertension, asthma, thyroid disease, pyelonephritis, active *Chlamydia*, Gonorrhea or Syphilis infections, active human papillomavirus (HPV) or herpes simplex virus (HSV) lesions, human immunodeficiency virus (HIV) infection and recreational drug use were excluded.

Human Blood and Tissue Samples

Placentas and the attached chorioamniotic membranes were obtained after delivery. In each case, several random strips of the chorioamniotic membranes located at different regions of the choriodecidua were embedded in rolls in optimal cutting temperature (OCT) compound (Sakura Finetek 4583), frozen in liquid nitrogen and stored at −80° C. for immunofluorescence analysis. Choriodecidual tissues were scraped from the chorionic membranes that had blood clots removed, and digested with 0.2% (w/v) *Clostridium histolyticum* Collagenase V (Sigma-Aldrich C9263) in RPMI-1640 with 10% fetal bovine serum (Thermo Fisher Scientific 26140-079) at 37° C. with gentle agitation for 45 minutes. Cells released from the tissues were cleaned by being passed through a 100 μm cell strainer and centrifuged on a Ficoll gradient. Peripheral blood leukocytes of anonymous healthy donors after leukophoresis were obtained from the Southeast Michigan branch of American Red Cross. Peripheral blood mononuclear cells (PBMCs) were isolated using Histopaque-1077 (Sigma-Aldrich 10771) following the manufacturer's instruction. Red blood cells were lysed using an ammonium-chloride-potassium (ACK) lysing buffer (Thermo Fisher Scientific A1049201). IgD+B cells were purified from PBMCs by magnetic-activated cell sorting (MACS) with a biotinylated goat F(ab')2 anti-human IgD antibody and anti-biotin magnetic microbeads (Miltenyi Biotec) as described in Chen, K., et al., Nat Immunol 10, 889-898 (2009). The purity of the IgD+B cells ranged from 92% to 99% as determined by flow cytometry with CD19 staining. CD19+ B cells were similarly separated from PBMCs using a biotinylated mouse anti-human CD19 (clone HIB19) antibody, with purity ranging from 93% to 97% as determined by flow cytometry using a different clone (SJ25C1) of CD19 antibody.

Mice

Figure 12A:
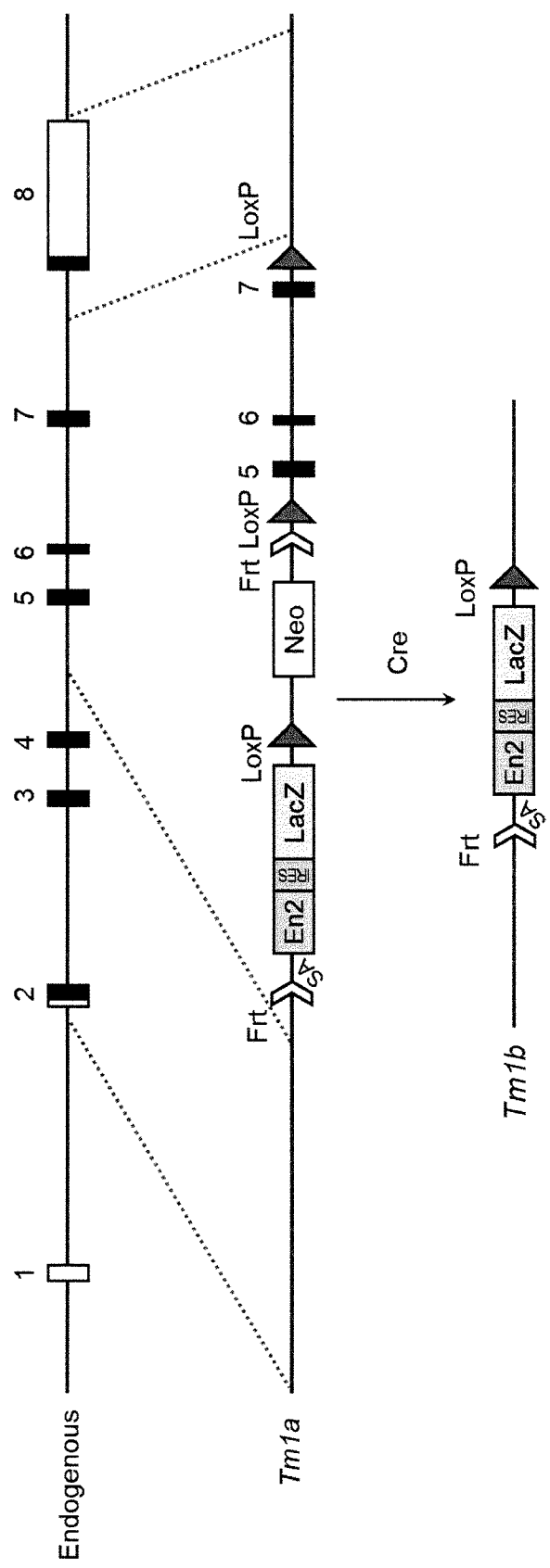
FIGS. 12A, 12B, 12C, and 12D show that PIBF1 expression is reduced in uterine tissues and uterine B cells in IL-33−/− mice.
Figure 12B:
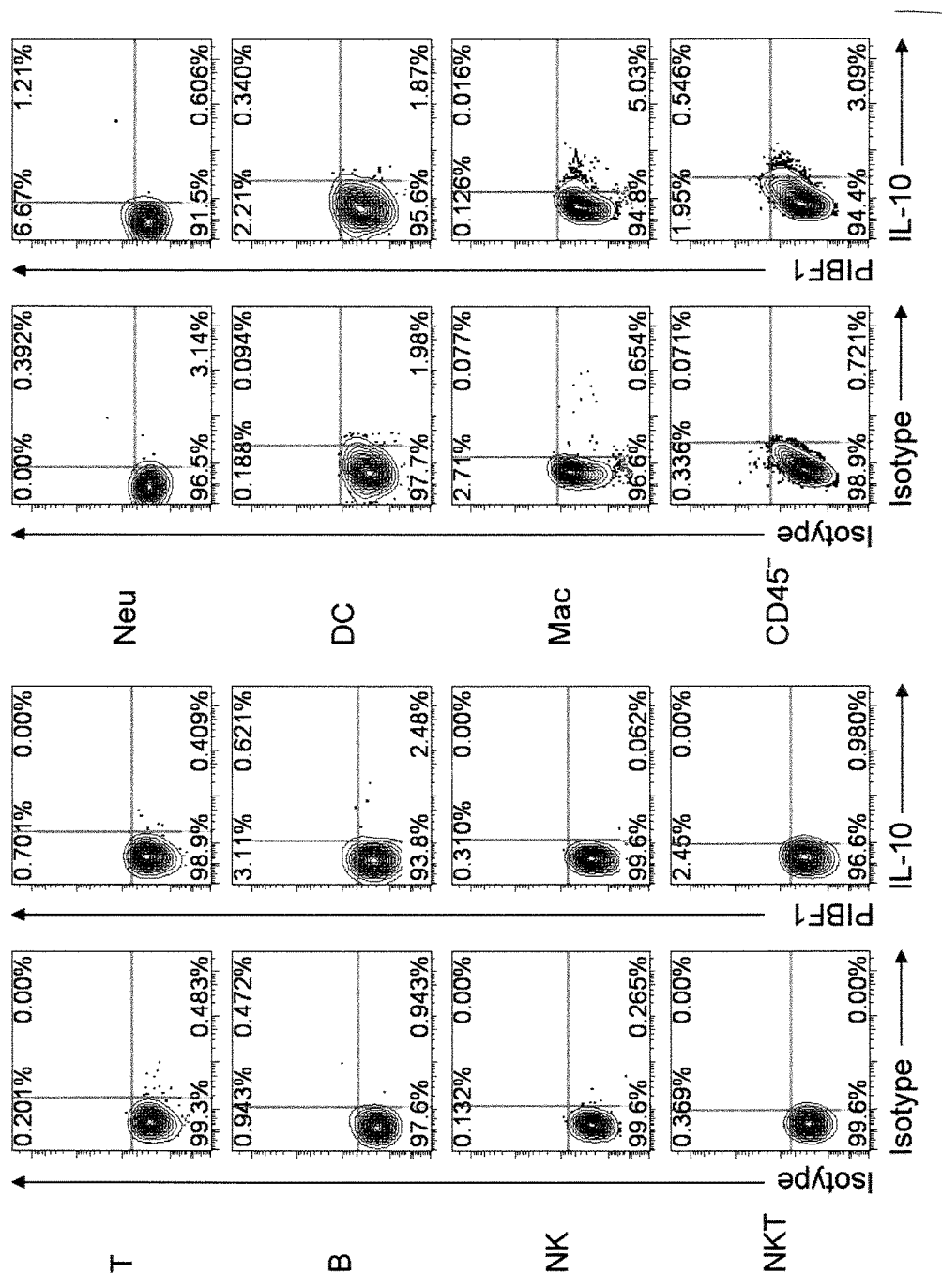
Figure 12C:
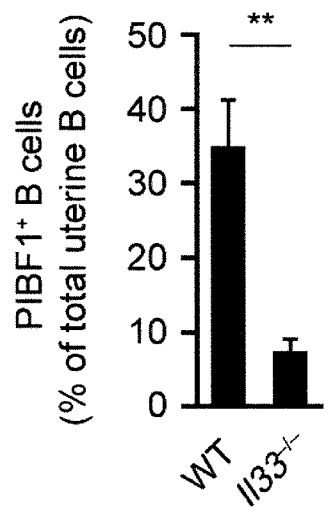
Figure 12D:
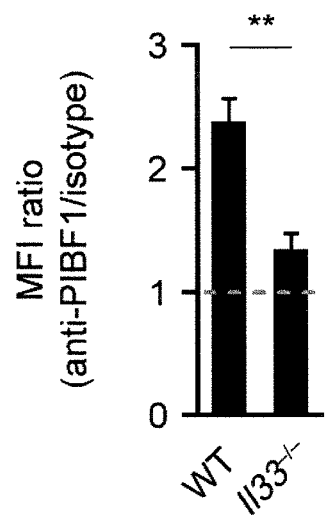

C57BL/6 mice (Jackson stock number 000664), Balb/c mice (Jackson stock number 000651), μMT (B6.129S2-ghm$^{tm1Cgn}$, Jackson stock number 002288) and IL-10-/- (B6.129P2-IL10$^{tm1Cgn}$, Jackson stock number 002251) mice in C57BL/6 background were purchased from the Jackson Laboratory. IL-33-/- lacZ reporter mice in C57/BL6 background (FIG. 12A) were generated by the mouse core of the NIH/NIAID Mucosal Immunology Studies Team (MIST) at Washington University School of Medicine. All mice were maintained in the same specific pathogen-free (SPF) facility.

Mouse Models of Preterm Labor

Six to ten-week old virgin female C57BL/6 (WT) or μMT mice were mated with male Balb/c mice. Female mice were examined daily in the early morning for the presence of a vaginal plug, which denoted gestational day (gd) 0.5. In the late morning of gd 16.5, pregnant female mice were intraperitoneally administered with 200 μl sterile PBS or 200 μl sterile PBS containing 0.5, 2.5, 5, 10 or 20 μg lipopolysaccharides (LPS) from *Salmonella enterica* serotype *typhimurium* (Sigma-Aldrich L6143). The various doses of LPS were given to the mice randomly. In some experiments, splenic B cells of 5 to 8-week old virgin female WT or IL-10-/- mice were purified using a mouse resting B cell negative isolation kit (Miltenyi Biotec 130-090-862) to 94% to 99% purity as determined by CD19 staining. 107 purified B cells were adoptively transferred in 200 μl sterile PBS into pregnant female μMT mice on gd 14.5 prior to LPS administration on gd 16.5. In some other experiments, 200 μl sterile PBS or 200 μl sterile PBS containing 800 ng recombinant full-length PIBF1 (fPIBF1) (aa 1-757 (SEQ ID NO:11, with an N-terminal glutathione-S-transferase (GST) tag of 232 amino acids, Abnova H00010464-P01) or 300 ng of a recombinant C-terminal fragment of PIBF1 (cPIBF1) (aa 660-755 (SEQ ID NO:12), with an N-terminal glutathione-S-transferase (GST) tag of 232 amino acids, Abnova H00010464-Q01) was intravenously administered to pregnant female μMT mice on gd 16.5 three hours prior to intraperitoneal LPS administration. 24 hours after LPS administration, female mice were examined for delivery and death of delivered pups if delivery occurred. They were then sacrificed for the examination of neonatal/fetal mortality, which was calculated as the total number of dead delivered pups and dead fetuses divided by the total number of implantation sites. Uteri were collected, briefly washed in PBS and processed for RNA and protein extraction or flow cytometry. The people performing the analysis were not blinded to the genotype or treatment of the mice.

Cell Culture

Human PMBCs, IgD+B cells, CD19+ B cells or PBMCs depleted of CD19+ B cells were cultured in RPMI-1640 medium (Sigma-Aldrich R8578) supplemented with 2 mM L-glutamine, 2 mg/ml NaHCO$_3$, 100 U/ml penicillin, 100 g/ml streptomycin, 0.25 g/ml amphotericin B and 10% FBS. Cells were stimulated with 100 ng/ml IL-33 (R&D 3625-IL-010 or Peprotech 200-33), 1 μM progesterone (Sigma-Aldrich P0130), IL-4 (Peprotech 200-04), IL-10 (Peprotech 200-10), IL-17A (Peprotech 200-17), IL-25 (R&D 1258-IL-025), IFN-γ (Peprotech 300-02), TGF-β (R&D 240-B-010/CF), TNF (210-TA-020) or TSLP (Peprotech 300-62). RNA or protein expression was analyzed after 2 days.

RNA Extraction and Quantitative Real-Time Polymerase Chain Reaction

RNA was extracted from cells or tissues using TRIzol (Thermo Fisher Scientific 15596026). cDNA synthesis was performed using the Superscript III first strand synthesis system (Thermo Fisher Scientific 188080051) in a thermocycler (Bio-Rad T100). qRT-PCR was performed with Power SYBR Green PCR Master Mix (Thermo Fisher Scientific 4367660) in a StepOnePlus instrument (Applied Biosystems) using pairs of sense and anti-sense primers targeted at the genes of interest (Tables 2, 3).

Flow Cytometry and Cell Sorting

Cells were incubated with an Fc blocking reagent and stained at 4° C. with antibodies to various cell surface antigens (Tables 4, 5). For staining of intracellular molecules, cells were subsequently fixed and permeabilized using a CytoFix/CytoPerm kit (BD 554722). Isotype-matched control antibodies were used to define the baseline staining for the molecules of interest. Cells or beads stained with each fluorochrome were used to establish fluorescent compensation. 7-aminoactinomycin D (7-AAD, Tonbo Biosciences 13-6993-T500 or BD Biosciences 559925) or Ghost Dye Violet 510 (Tonbo Biosciences 13-0870-T500) was used to identify dead cells in order to exclude them from the analysis. Events were acquired on an LSR II cytometer (BD Biosciences) and analyzed by FlowJo (Tree Star). In some experiments, stained cells were sorted using a SONY SH800 or SH3200 cell sorter (SONY Biotechnology).

Imaging Flow Cytometry

Choriodecidual cell suspensions were incubated with an Fc blocking reagent and stained at 4° C. with antibodies to various surface antigens, fixed and permeabilized, and stained for PIBF1 or with an isotype control antibody, followed by a fluorochrome-conjugated secondary antibody (Tables 4, 6). Nuclei were counter stained with Hoechst 33342 (Thermo Fisher Scientific 62249). Cells or beads stained with each fluorochrome were used to establish fluorescent compensation. Cells were imaged on an ImageStream X Mark II imaging flow cytometer (Amnis) and data were analyzed using IDEAS 6.1 (Amnis).

Immunohistochemistry

Frozen human tissues were stored at -80° C. shortly before sectioning. 6-7 μm tissue sections were made using a cryostat (Leica CM1950). Sections were fixed with 4% paraformaldehyde, permeabilized in PBS containing 0.2% Triton X-100, blocked with PBS containing 10 mg/ml bovine serum albumin (BSA) and 100 μg/ml human IgG. Endogenous biotin was subsequently blocked with an avidin/biotin blocking kit (Thermo Fisher Scientific 004303). The tissues were stained with a biotinylated antibody against human CD19 (Table 4) or a biotinylated mouse IgGl isotype control antibody (Table 6) followed by horseradish peroxidase-conjugated streptavidin (Table 6). The color reaction was developed using 3,3'-diaminobenzidine as the substrate (Vector Laboratories SK-4105). Nuclei were visualized with hematoxylin. Slides were imaged using an Olympus BX40 or Nikon TE-2000 microscope with CellSens Dimension software.

Immunofluorescence

Frozen human tissues were stored at -80° C. shortly before sectioning. 6-7 μm tissue sections were made using a cryostat (Leica CM1950). Sections were fixed with 4% paraformaldehyde, permeabilized in PBS containing 0.2% Triton X-100, blocked with PBS containing 10 mg/ml bovine serum albumin (BSA), 100 μg/ml human IgG and 10%/o serum from the source of the fluorochrome-conjugated antibodies, and stained with various combinations of primary antibodies against the molecules of interest (Table 4), followed by appropriate fluorochrome-conjugated secondary antibodies (Table 6). Nuclei were visualized with 4',6-diamidine-2'-phenylindole dihydrochloride (DAPI, Sigma-Aldrich D9542). Following washing, slides were mounted using a FluoroSave reagent (EMD Millipore 345789) and imaged using a confocal microscope. Pseudocolor images were processed using Photoshop (Adobe).

Protein Extraction and Western Blot

Cells were pelleted and washed twice with cold PBS and lysed in a pH 8.0 protein extraction buffer containing 20 mM Tris-HCl, 150 mM NaCl, 1% IGEPAL CA-630 (Sigma-Aldrich 18896), 0.1% sodium dodecyl sulfate (SDS), 1 mM EDTA and protease and phosphatase inhibitor cocktail on ice for 30 minutes. For protein extraction from mouse uterus and human chorioamniotic membranes, the tissue was washed twice with PBS to remove blood and homogenized in the above protein extraction buffer with a tissue tearor (Biospec Products 985370), followed by 3 rounds of sonication at 30% maximum power for 5 seconds per round using a sonifier (Thermo Fisher Scientific Q500). Supernatants were collected after centrifugation, heated at 98° C. in an SDS buffer with 4% β-mecaptoethanol for 5 minutes to denature proteins. Proteins were resolved in 4-20% Bis-Tris gels (GenScript M42012) and transferred to 0.45 μm nitrocellulose membranes (Bio-Rad 1620115). The membranes were blocked with 5% (w/v) non-fat milk in Tris-buffered saline with Tween-20 for 30 min, incubated with primary antibodies overnight at 4° C. and subsequently with secondary antibodies conjugated to horseradish peroxidase (HRP) (Tables 4-6). Signals were visualized with clarity westernblot ECL substrate (Bio-Rad 170-5061) and exposed on autoradiograph films.

Statistical Analysis

The sample size was calculated based on the effect size derived from preliminary data at 5% significance level and 80% power using the software G*Power 3.1. Sample availability exceeded the estimated sample size. Results are expressed as mean±S.E.M. Percentage data were subjected to square root transformation prior to statistical analysis to verify test assumptions of equal variance. Statistical difference in the rate of PTL between different strains of mice or different treatment groups was assessed by Fisher's exact test. Statistical difference in neonatal/fetal mortality was assessed by Mann-Whitney U test. For flow cytometry and qRT-PCR data, Shapiro-Wilk test was used to determine the normality of the data. Statistical significance was assessed by Student's t-test for normally distributed data and Mann-Whitney U test for non-normally distributed data. p values <0.05 were considered statistically significant.

Results

Figure 5:
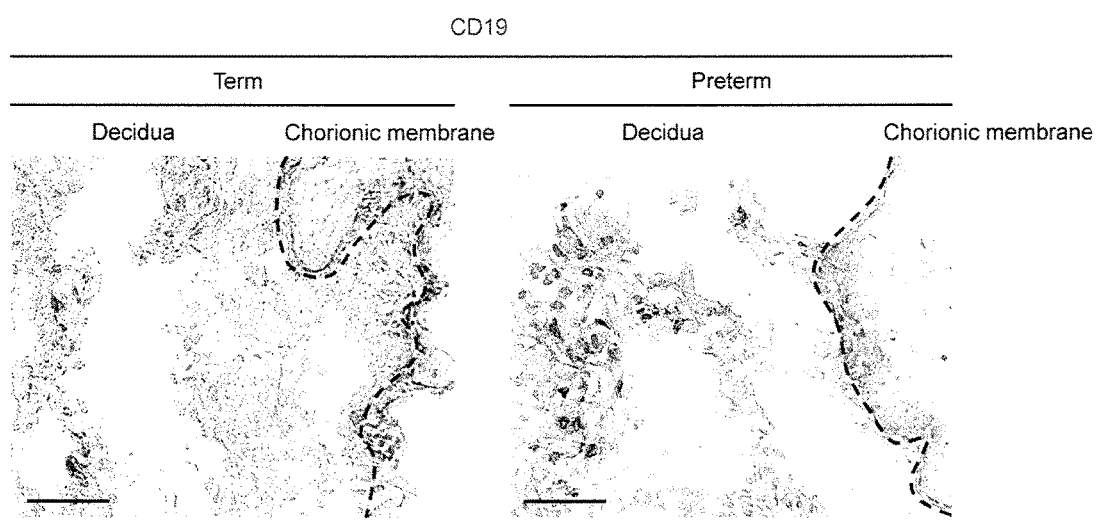
FIG. 5 shows that B cells are found in choriodeciduas of women undergoing TL or PTL at delivery. Immunohistochemical analysis of CD19 in the choriodecidual tissue of a woman undergoing TL (left) and a woman undergoing PTL (right). Nuclei were countered with hematoxylin. The dotted lines outline chorioamniotic membranes. Bar: 50 µm.

By analyzing specimens of women with spontaneous term labor (TL) or PTL (Table 1), it was found that B cells are present in human choriodeciduas (FIG. 5) and constitute approximately 1% and 2.5% of CD45+ cells in TL and PTL cases respectively (FIGS. 1A, IB, and IC). Choriodecidual B cells exhibited a distinct profile from that of peripheral blood B cells by expressing higher levels of activated, memory B cell- or plasma cell-associated molecules CD27, CD38, CD70, CD80, CD86, CD95, CD138 and B cell maturation antigen (BCMA) and lower levels of CD20, CD22, CD23, IgM, IgD and CCR7, suggesting increased activation, class switching, memory and plasmacytoid differentiation. Choriodecidual B cells also expressed integrins α4 and β7 and the C-C chemokine receptor (CCR) CCR6, but not CCR9 or CCR10 that promotes lymphocyte homing to intestine or skin-associated mucosal tissues respectively, indicating that B cell migration to choriodecidua involves non-overlapping homing receptors from migration to other mucosal sites. Compared to TL choriodecidua, PTL choriodecidua harbored increased B cells (FIGS. 1A, 1B, and IC) and CD20+CD70−CD43+CD27+ cells, a population postulated to be B-1 cells which spontaneously secrete autoreactive/polyreactive IgM and are implicated in other adverse pregnancy outcomes, and increased CD24−CD38hi plasma cells. The expression of several direct or indirect B cell-stimulating molecules, including B cell-activating factor of the tumor necrosis factor family (BAFF), a proliferation-inducing ligand (APRIL) and thymic stromal lymphopoietin (TSLP), was increased in PTL choriodecidual epithelial and/or stromal cells, which might underlie the expansion and increased activation of B cells in PTL choriodecidua. Collectively, human PTL choriodecidua harbors B cells with altered function characterized by aberrant expansion, increased activation and antibody production.

Figure 2A:
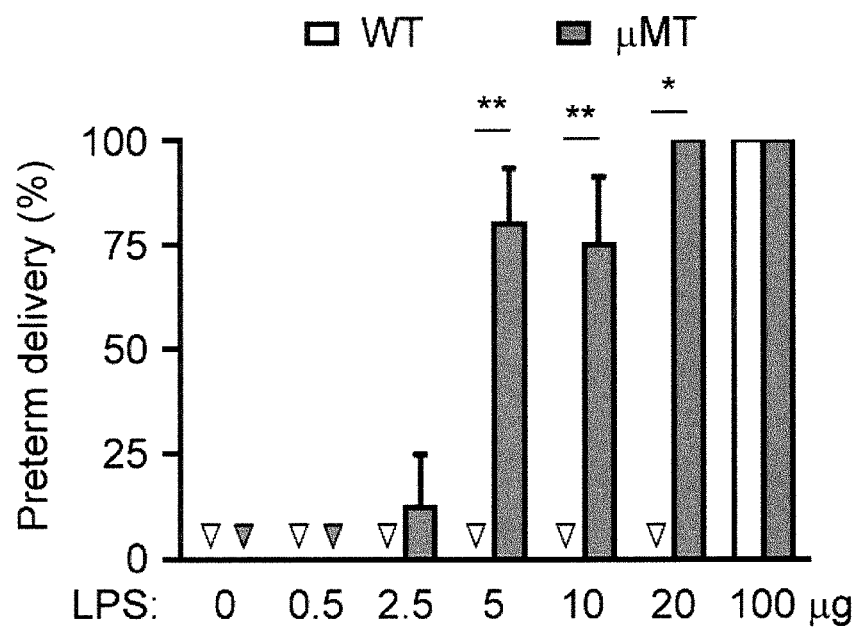
FIGS. 2A, 2B, 2C, 2D, 2E, 2F, 2G, 2H, and 2I demonstrate that B cells confer resistance to inflammation-associated PTL independently of IL-10.
Figure 2B:
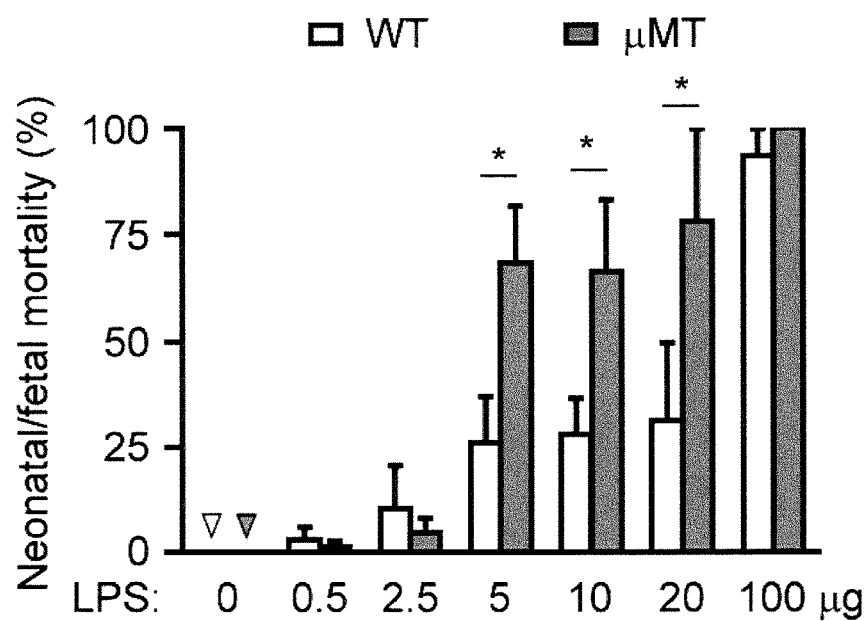
Figure 2C:
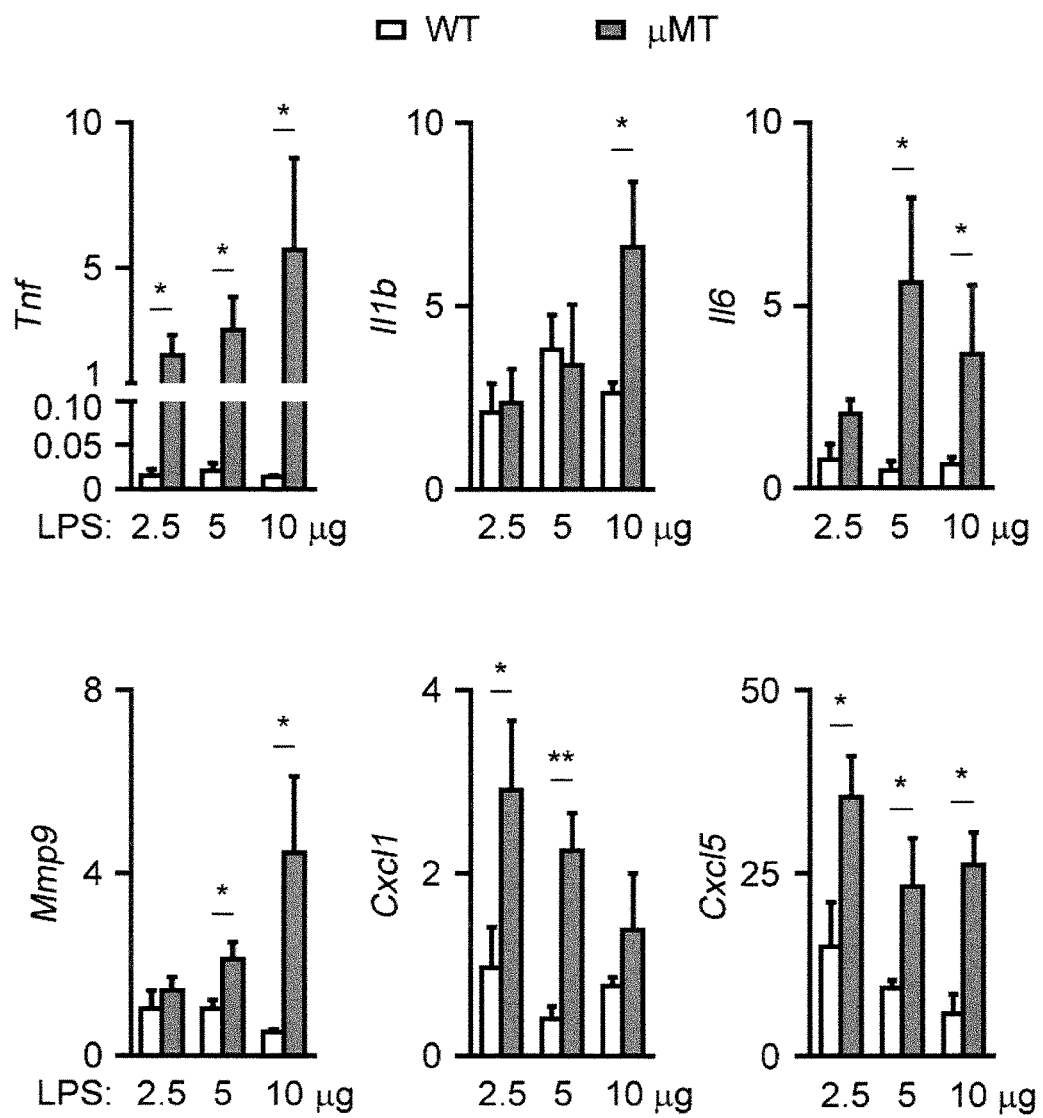
Figure 2D:
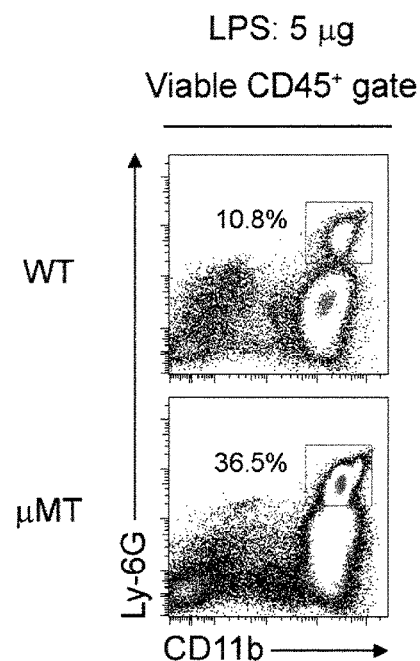
Figure 2E:
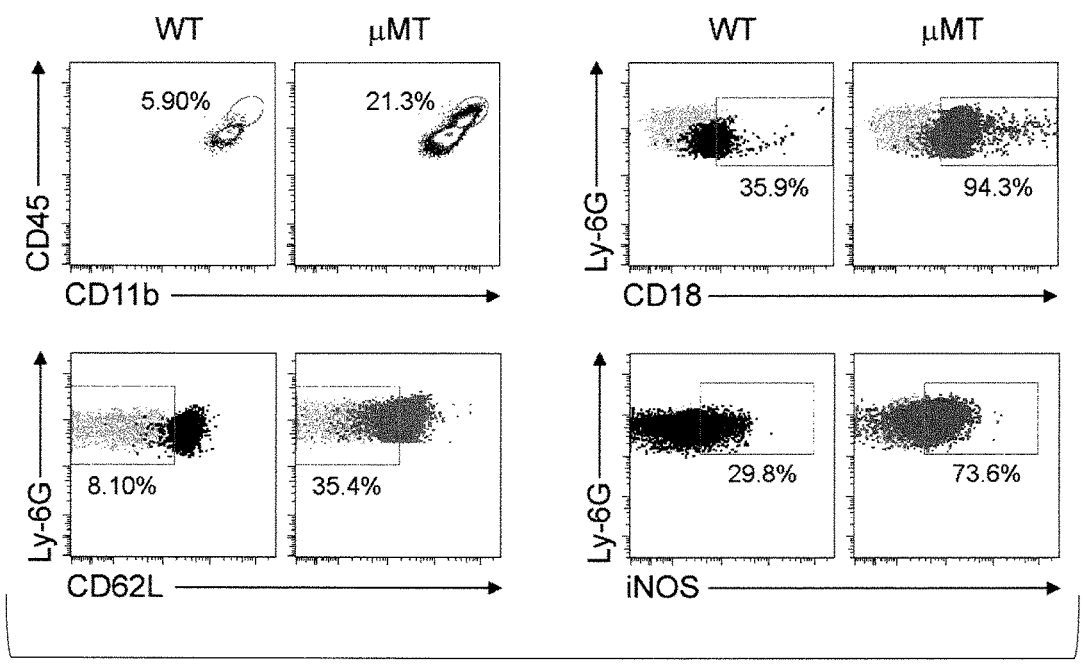
Figure 14A:
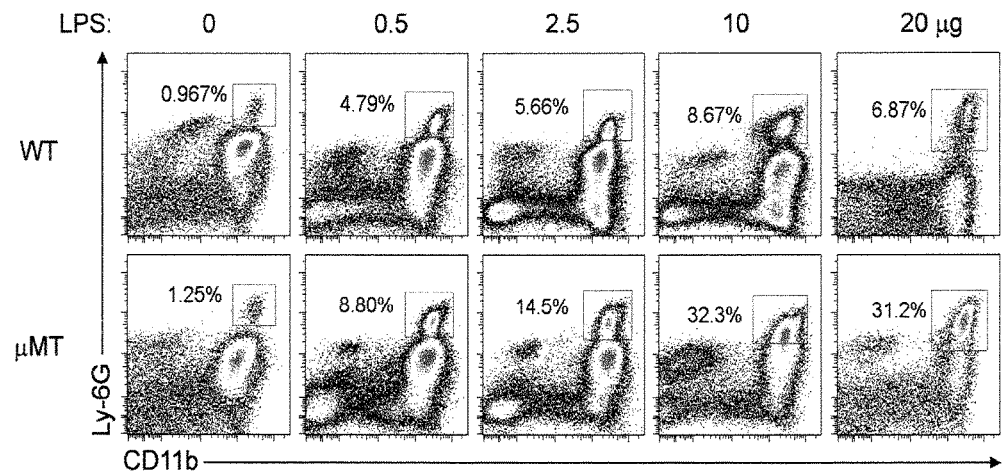
FIGS. 14A, 14B, and 14C show that μMT mice exhibit heightened uterine inflammation and increased uterine neutrophil infiltration and activation following LPS administration in late gestation.
Figure 14B:
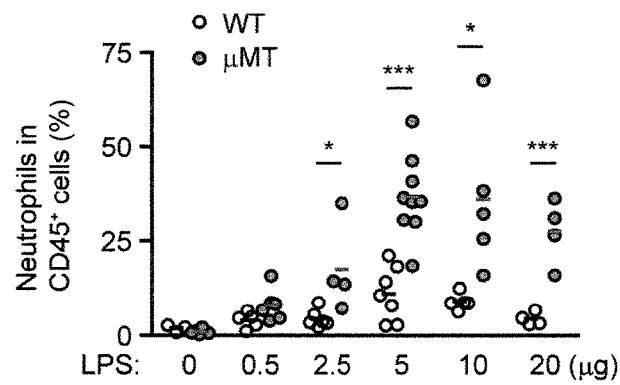
Figure 14C:
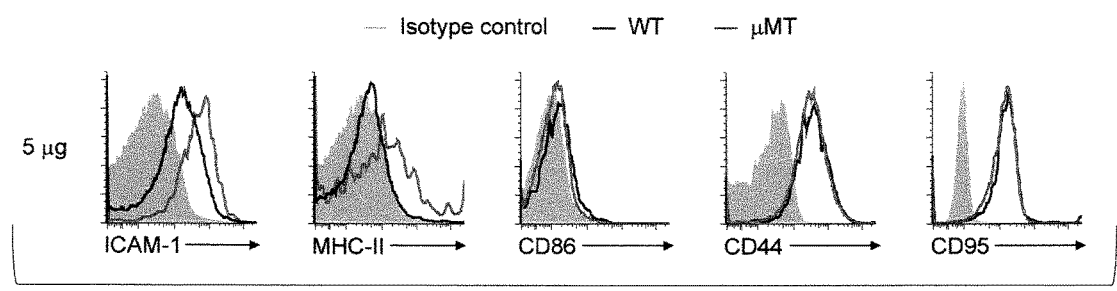

B cells produce interleukin-10 (IL-10) to suppress systemic and local inflammation, and IL-10 was critical in the protection against PTL induced by inflammation in mice. Human choriodecidual B cells had reduced IL-10 expression in PTL, although the total numbers of IL-10+B cells were similar in TL and PTL choriodeciduas. To determine if B cells protect against PTL triggered by inflammation, the susceptibility of wild-type (WT) C57BL/6 mice and B-cell-deficient μMT mice to PTL induced by administration of lipopolysaccharides (LPS) on gestational day (gd) 16.5 was compared. While WT mice were resistant to PTL and had a modest level of neonatal/fetal mortality after LPS administration, itMT mice suffered markedly higher rates of PTL and neonatal/fetal mortality (FIGS. 2A and 2B), which was accompanied by hyperinduction of uterine proinflammatory mediators (FIG. 2C) and increased neutrophil infiltration into the uterus (FIG. 2D, FIGS. 14A, and 14B. Neutrophils in the uterus of μMT mice exhibited heightened activation, including higher expression of CD11b, CD18, intercellular adhesion molecule-1 (ICAM-1), major histocompatibility complex class II (MHC-II) and inducible nitric oxide synthase (iNOS) and lower expression of CD62L (FIG. 2E and FIG. 14C). The proportions of uterine CD11b+Ly-6C+ inflammatory monocytes were similar in WT and μMT mice, which echoed comparable induction of Ccl2 in WT and μMT uteri. Hence, B cells protect against PTL induced by inflammation in the third trimester in mice.

Figure 2F:
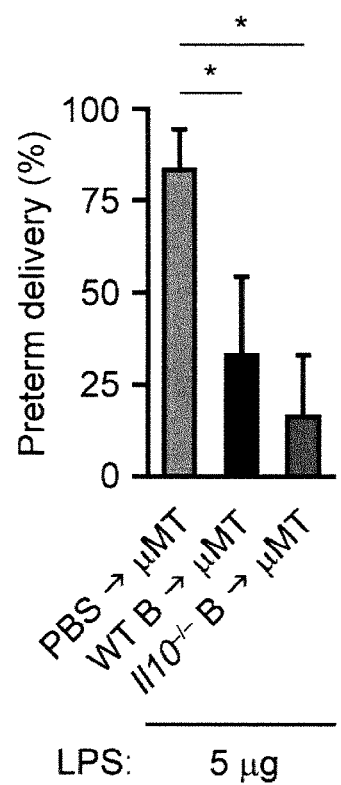
Figure 2G:
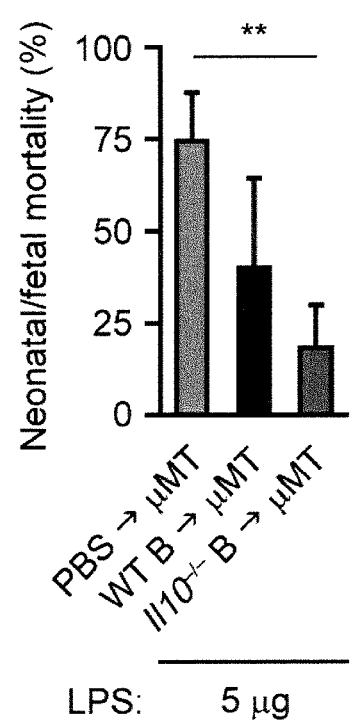
Figure 2H:
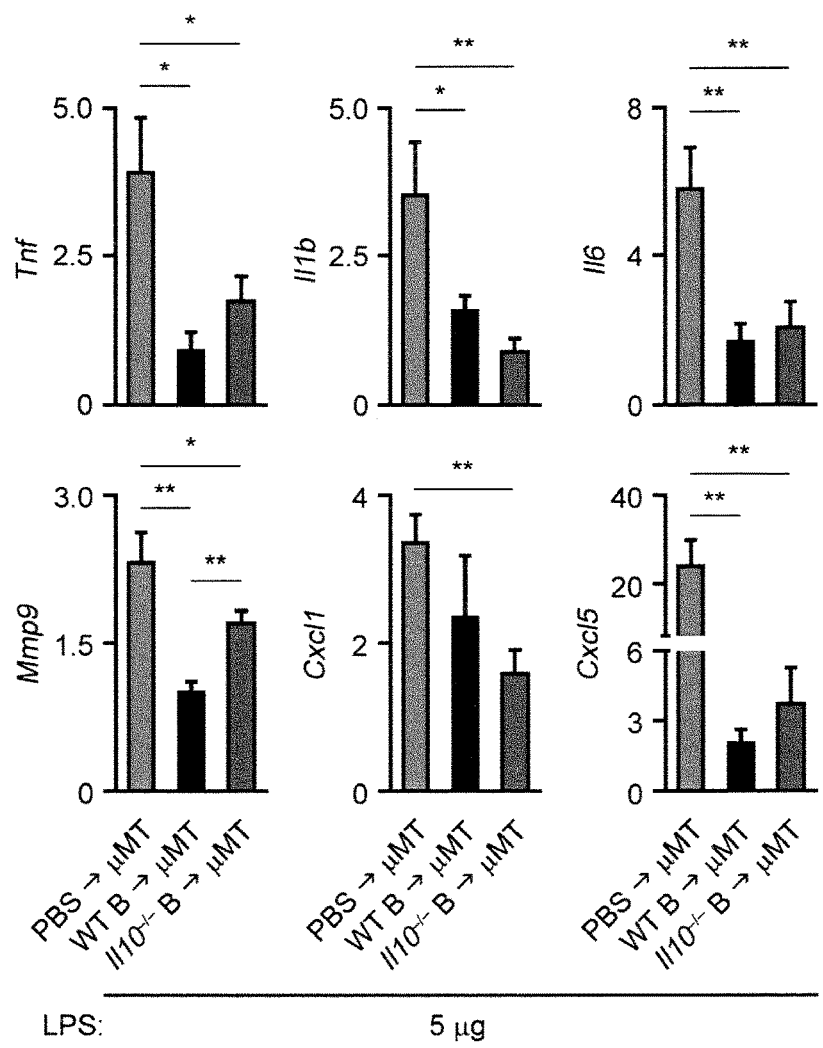
Figure 2I:
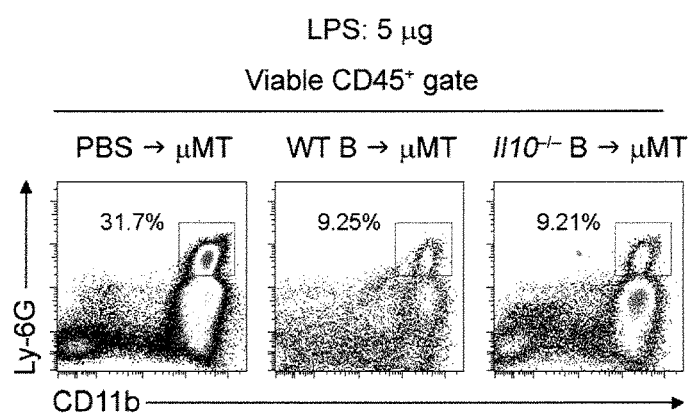

To test if B cells conferred protection against PTL by producing IL-10, LPS was administered on gd 16.5 to μMT mice that received either syngeneic WT or syngeneic IL-10−/− B cells. Adoptive transfer of either WT or IL-10−/− B cells restored the resistance of μMT mice to PTL (FIG. 2F), attenuated neonatal/fetal mortality (FIG. 2G) and suppressed uterine induction of proinflammatory mediators (FIG. 2H) and neutrophil infiltration (FIG. 2I). Consistent with IL-10-independent protection, the uterus of μMT mice showed higher IL-10 induction after LPS administration. The induction of two other B cell-derived regulatory cytokines, namely transforming growth factor-β (TGF-β) and IL-35, which consists of Epstein-Barr virus-induced gene 3 (EBI3) as a subunit, was similar in WT and μMT mice. μMT mice that received WT or IL-10−/− B cells also had similar induction of uterine Ebi3 after LPS administration as compared to μMT mice that did not receive B cells. Collectively, these data argue against a significant role of IL-10, TGF-β or IL-35 in B cell-mediated protection against PTL.

Figures 3A, 3B:
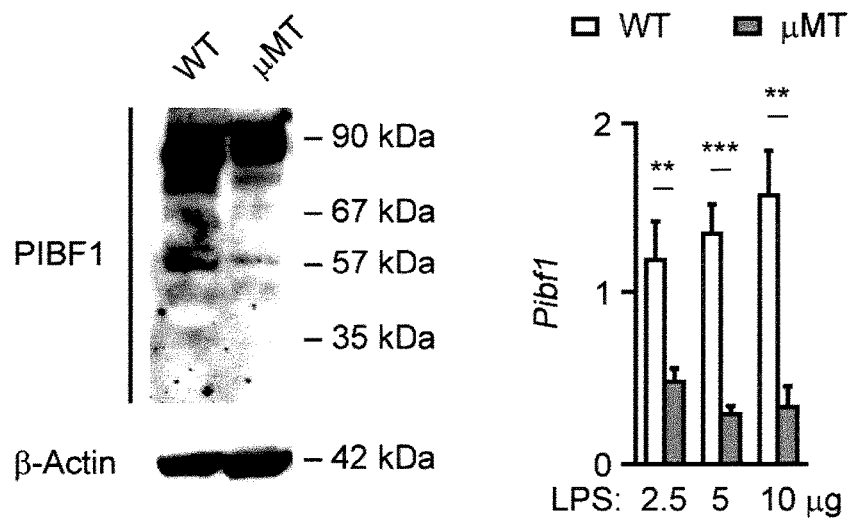
Figures 3C, 3D:
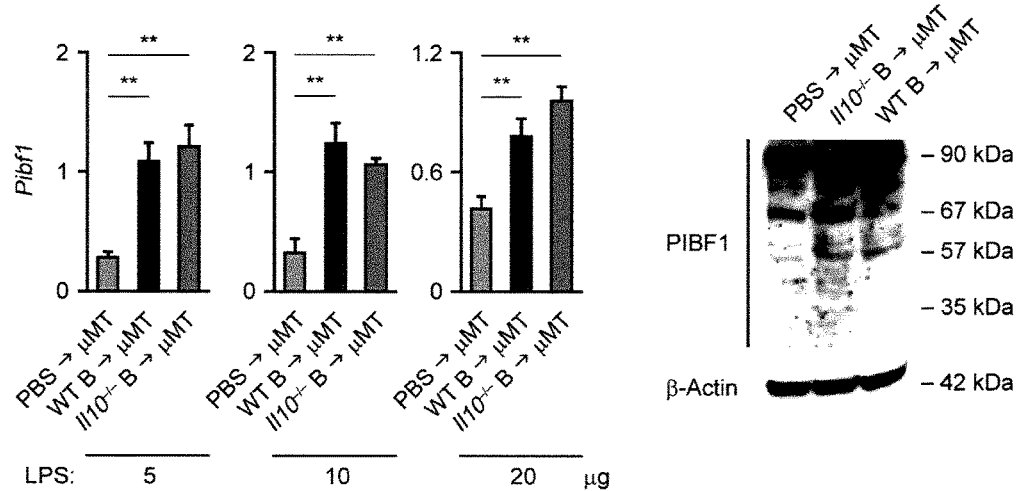
Figure 3E:
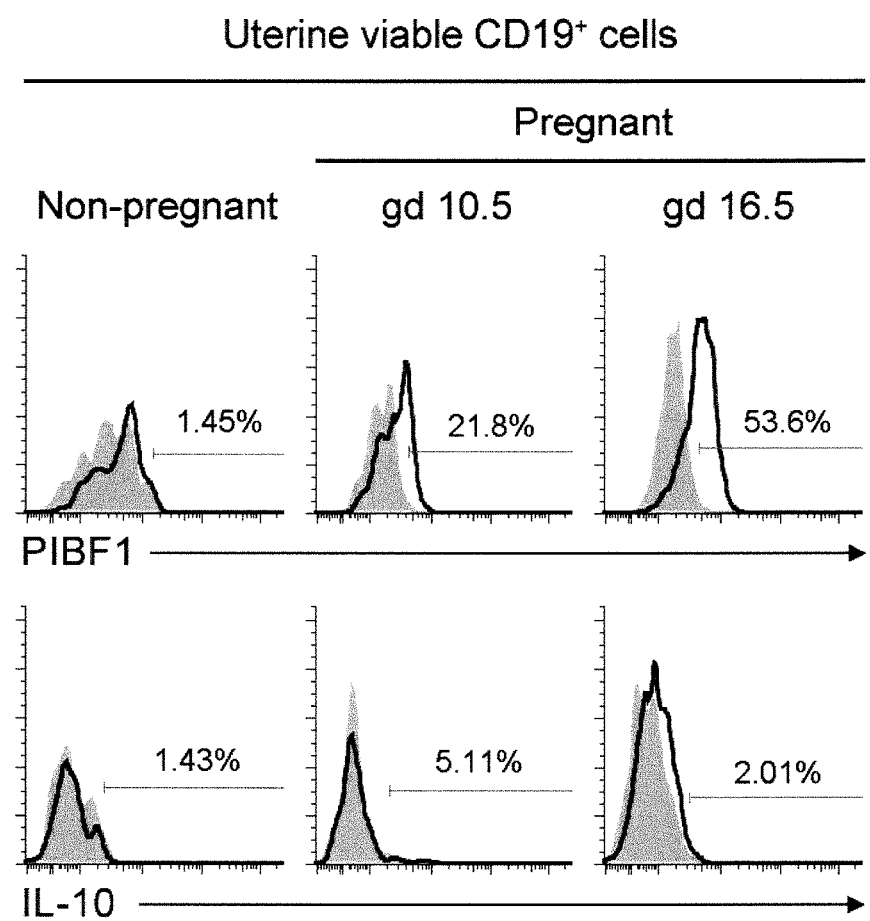
Figure 6A:
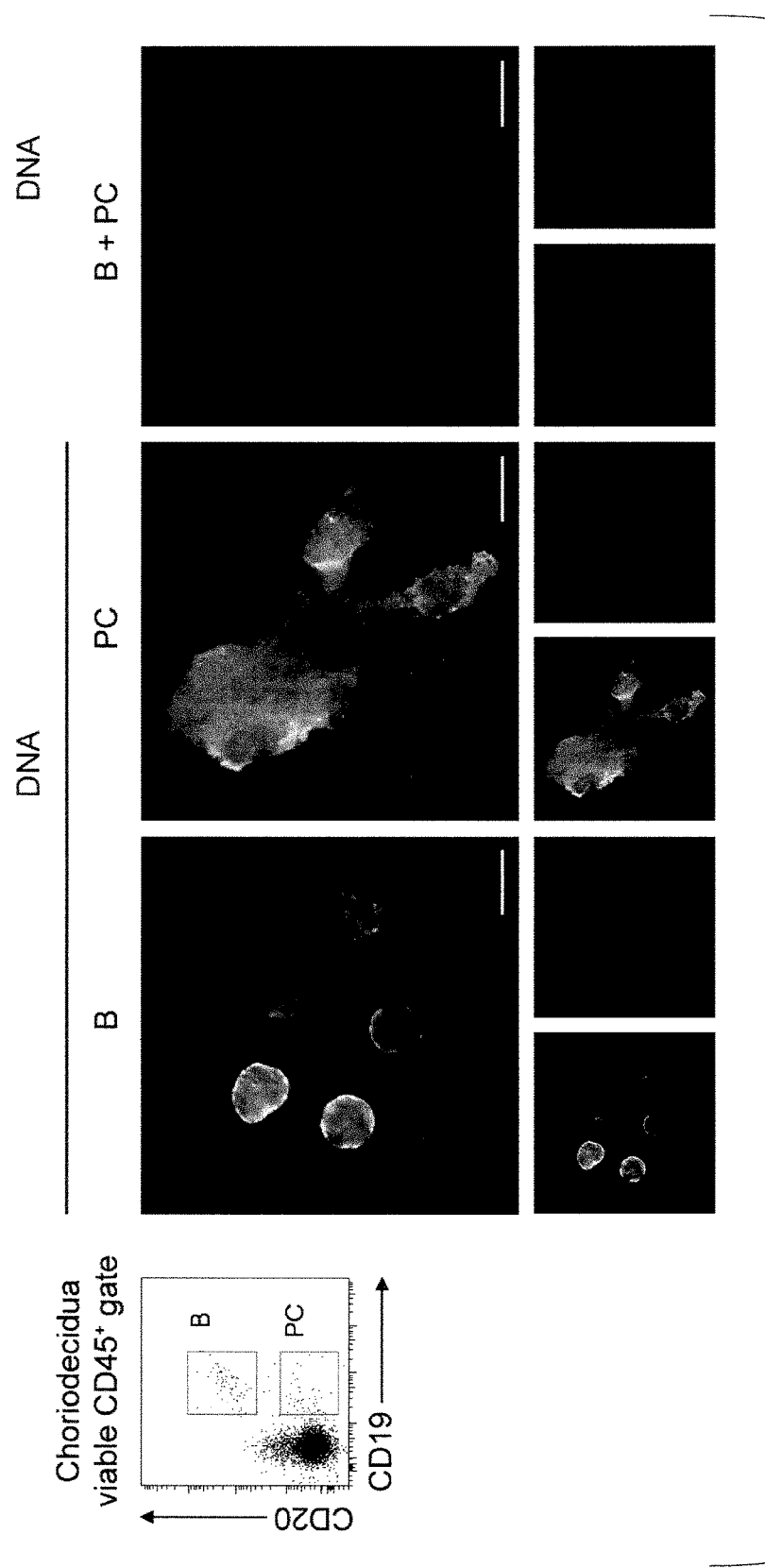
FIG. 6B shows results of cytospin followed by immunofluorescence analysis of PIBF1 expression by sorted CD19+CD20+B cells and CD19+CD20− plasma cells (PCs) in choriodecidual tissue of a TL subject. Bar: 10 pun.
Figure 6B:
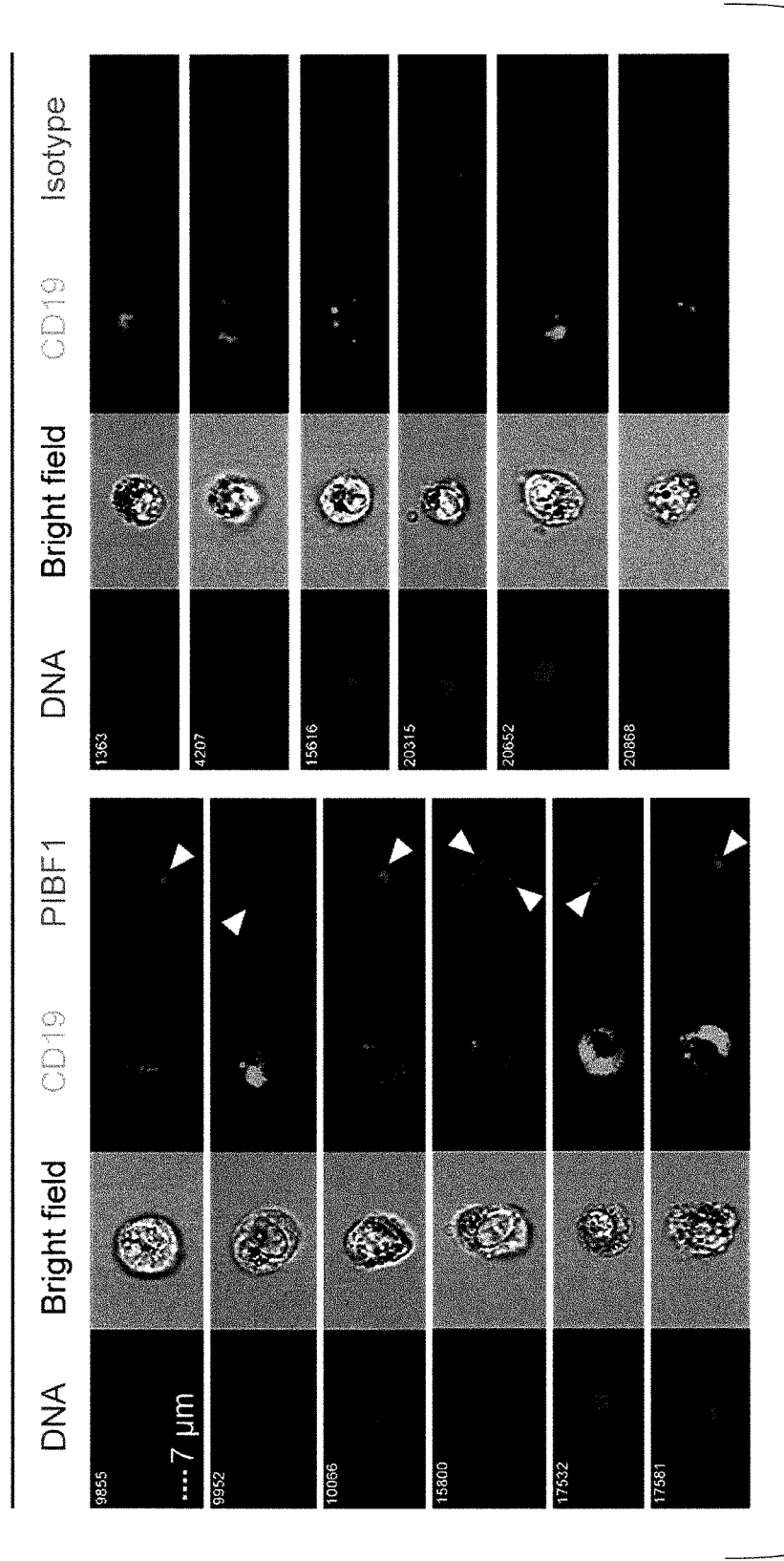
Figure 7A:
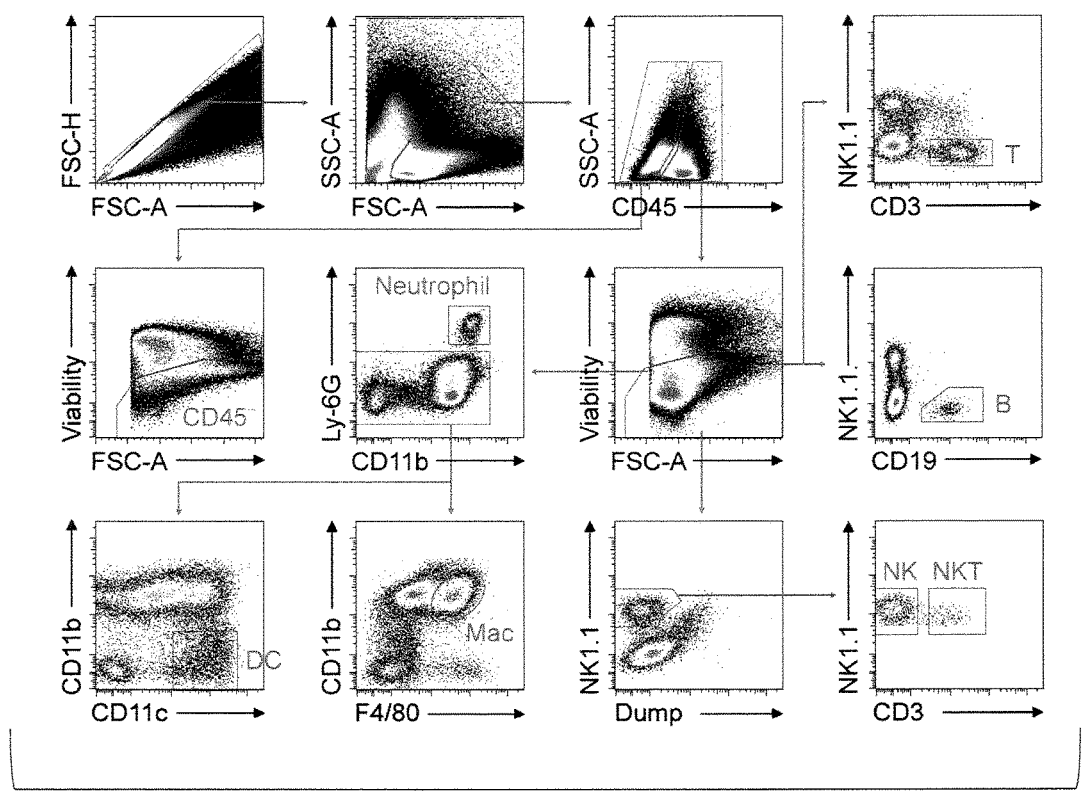
FIGS. 7A, 7B, 7C, and 7D demonstrate that B cells are the major producer of PIBF1 in mouse uterus during late pregnancy.
Figure 7B:
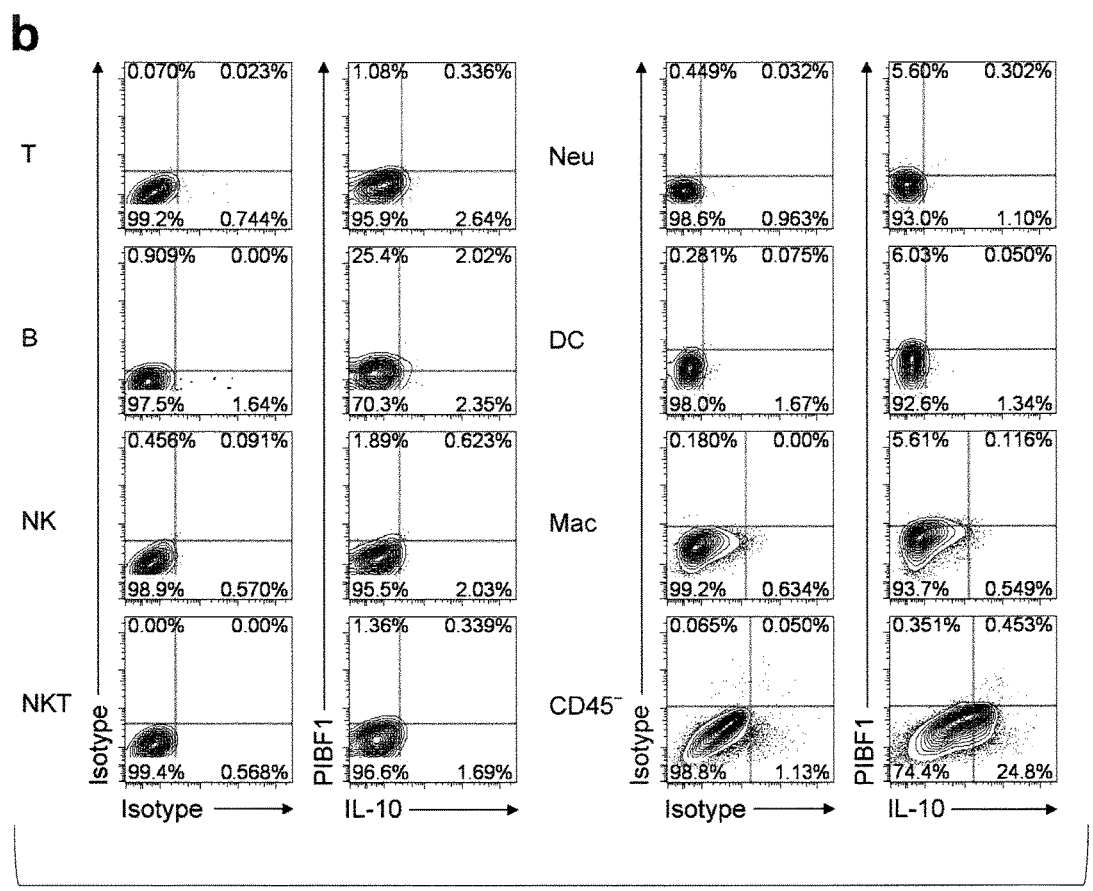
Figure 7C:
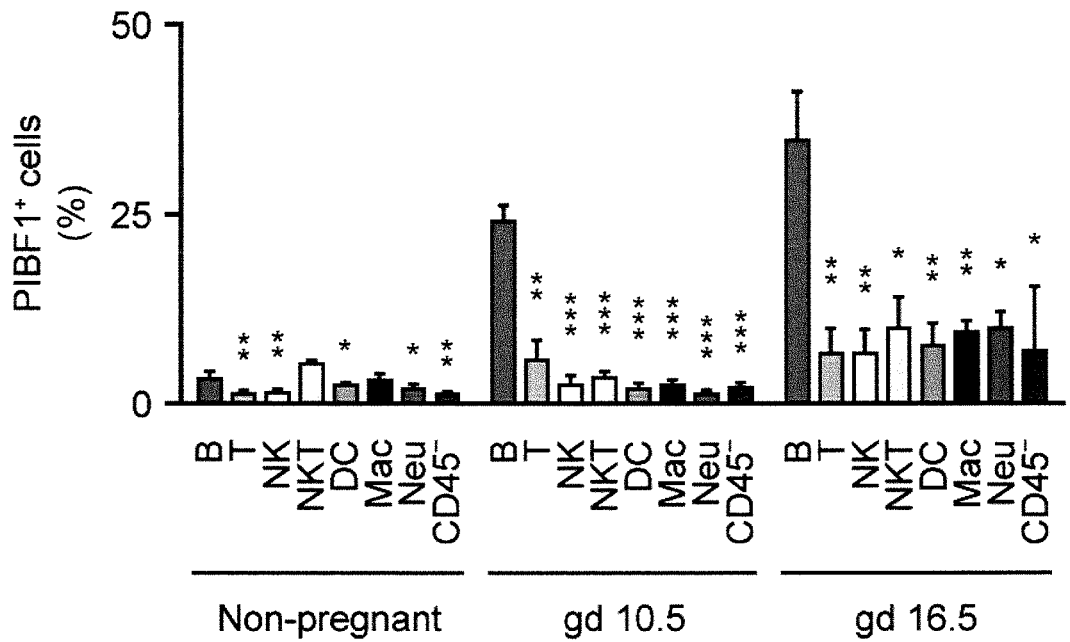
Figure 7D:
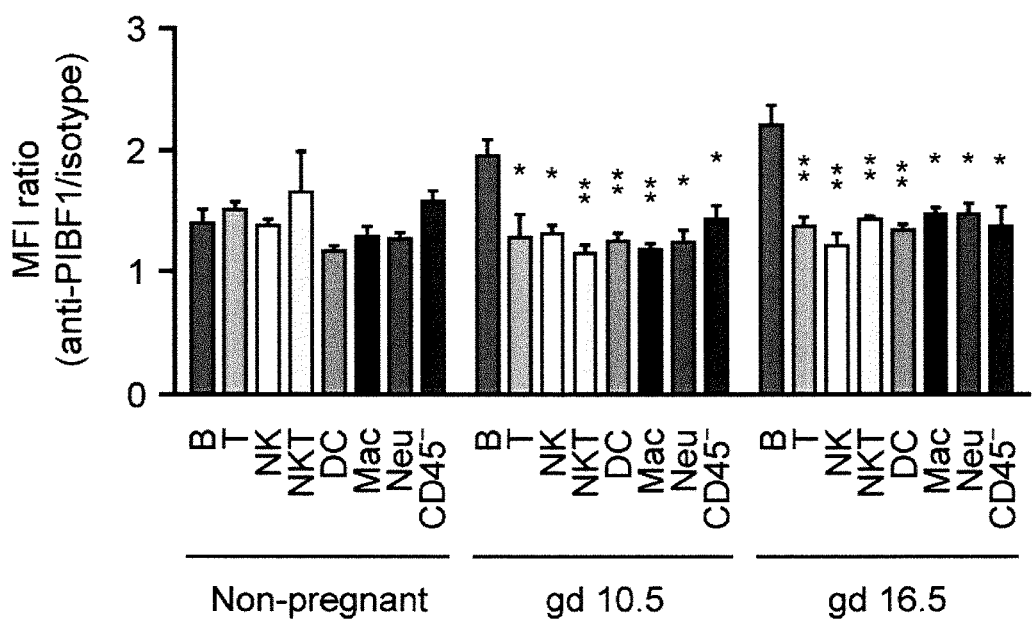
Figure 8A:
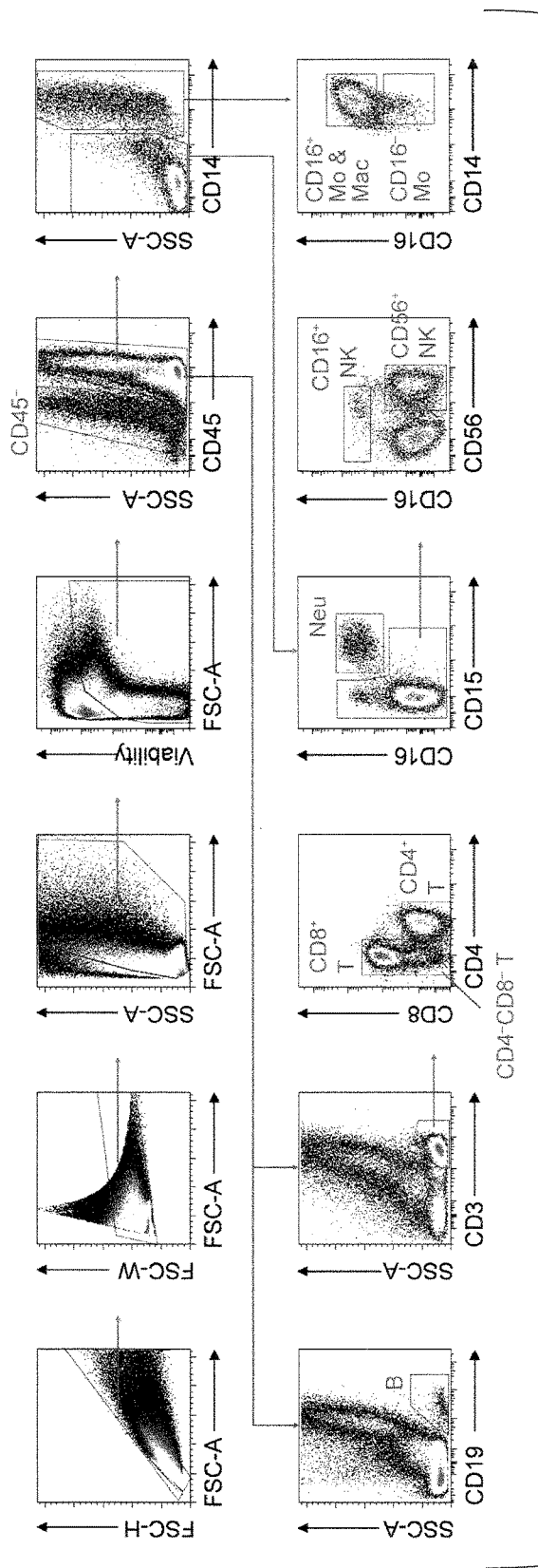
FIGS. 8A, 8B, 8C, 8D, and 8E demonstrate that B cells are the major producer of PIBF1 in human choriodecidua at term delivery.
Figure 8B:
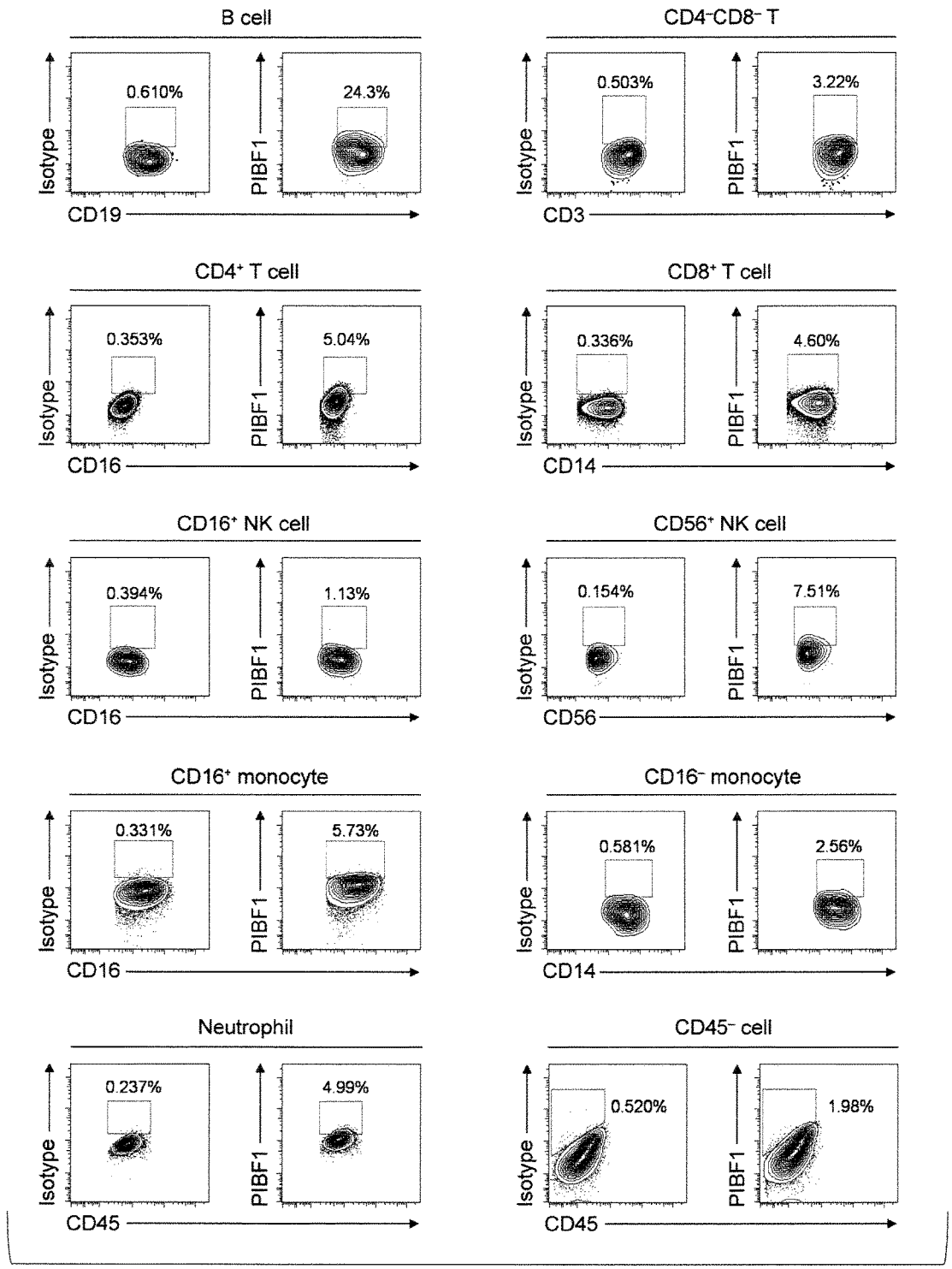
Figure 8C:
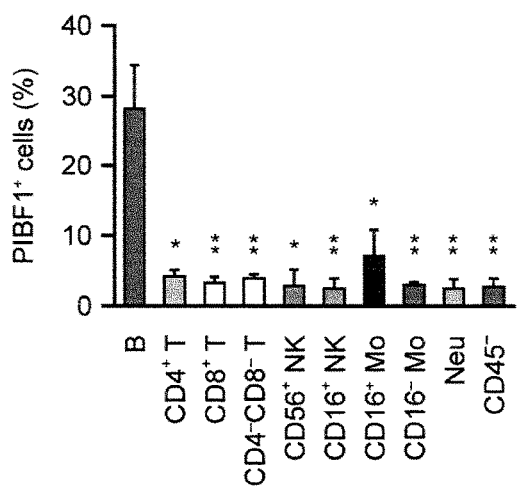
Figure 8D:
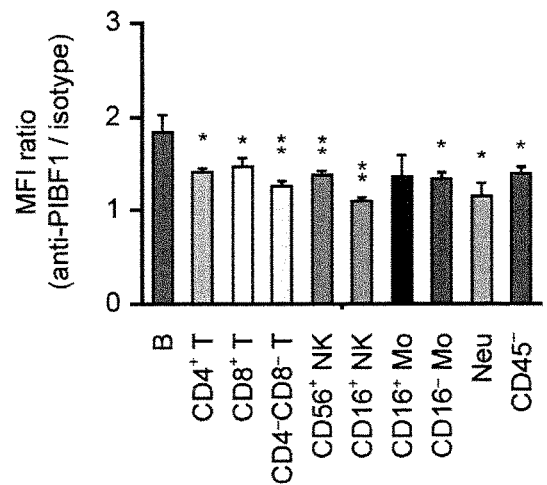
Figure 8E:
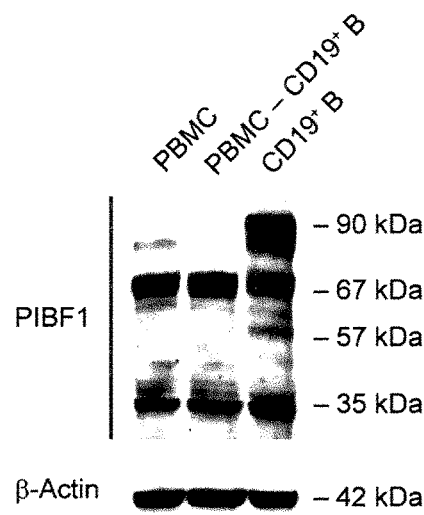

Compared to WT mice, μMT mice had diminished active PIBF1 expression in late gestation uterus (FIG. 3A) and defective induction of uterine Pibf1 transcript after LPS administration (FIG. 3B). Adoptive transfer of WT or IL-10−/− B cells to μMT mice increased the expression of active PIBF1 after LPS administration (FIGS. 3C and 3D). These results suggest that B cells are an important contributor of active PIBF1 in mouse uterus during late pregnancy. Flow cytometric and immunofluorescent analyses were performed and it was found that mouse uterine B cells expressed PIBF1 during mid- and late gestation (FIG. 3E), and human choriodecidual B cells also expressed PIBF1 (FIGS. 3F, 3G and FIG. 6A). PIBF1 in choriodecidual B cells was concentrated perinuclearly and distributed in the cytoplasm (FIG. 3H and FIG. 6B), consistent with the localization for centrosome-associated and secretory PIBF1 respectively. Remarkably, B cells were the population with the highest PIBF1 expression in mouse uterus (FIGS. 7A, 7B, 7C, and 7D) and human choriodecidua (FIGS. 8A, 8B, 8C, and 8D). Furthermore, human peripheral blood CD19+ B cells contained more full-length and active PIBF1 protein than other mononuclear cells (PBMCs), and PBMCs depleted of B cells were almost devoid of full-length and active PIBF1 (FIG. 8E). Therefore, B cells are a significant producer of active PIBF1 in human choriodecidua and mouse uterus during late pregnancy.

Figure 3I:
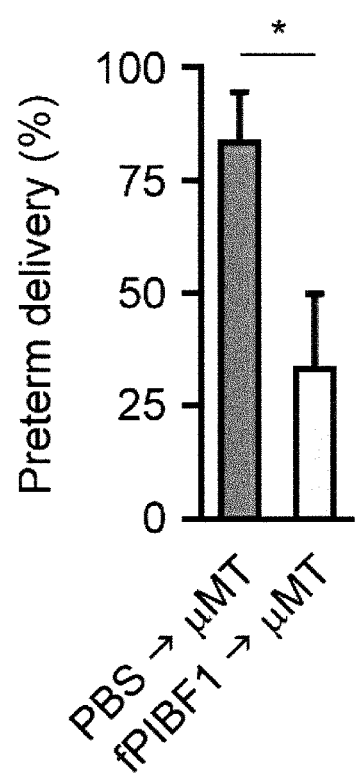
Figure 3J:
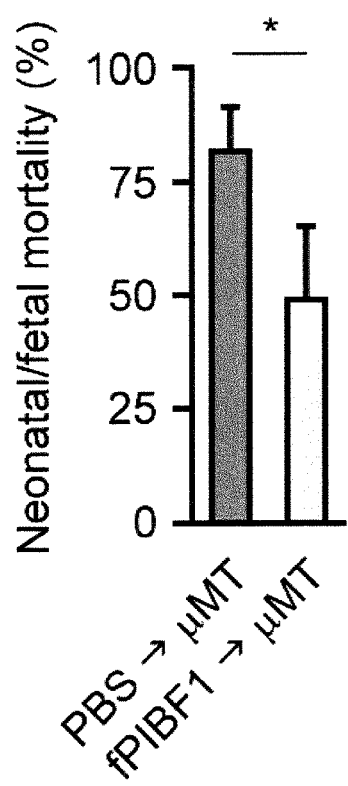
Figure 3K:
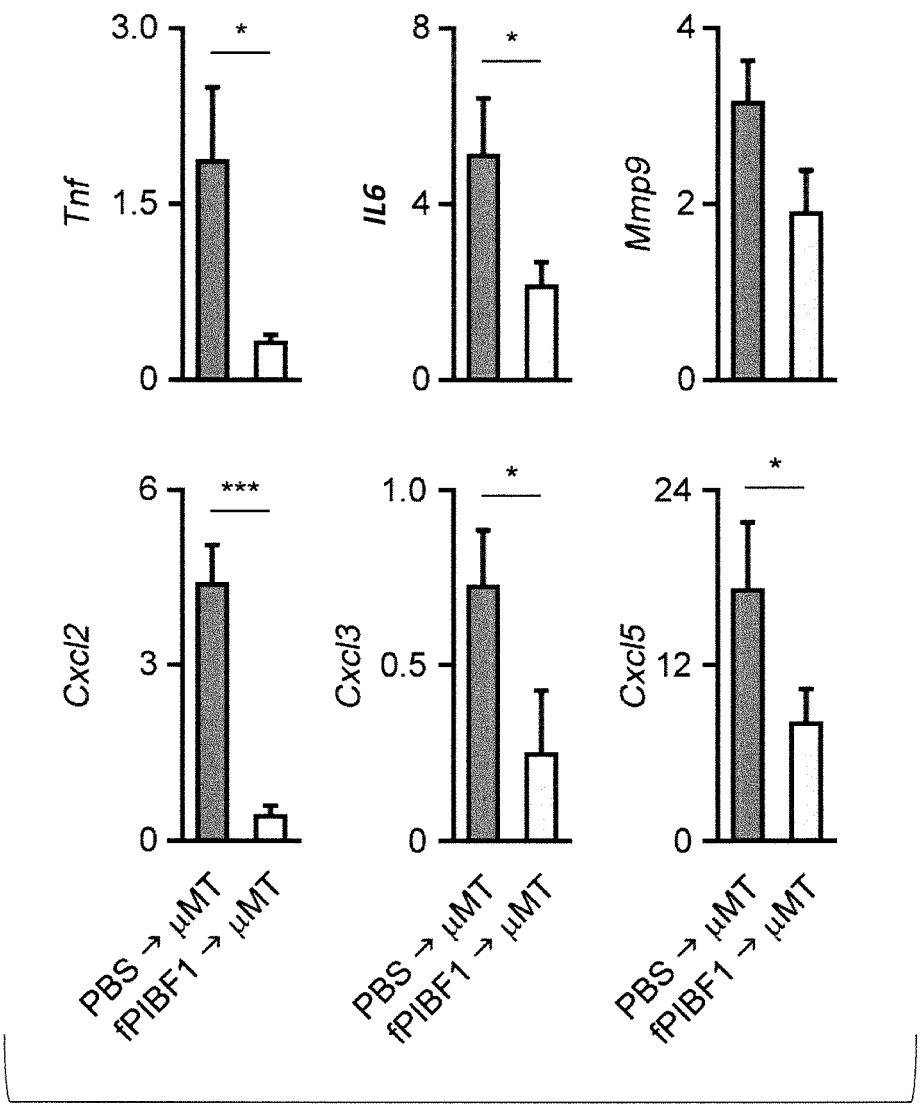
Figure 3L:
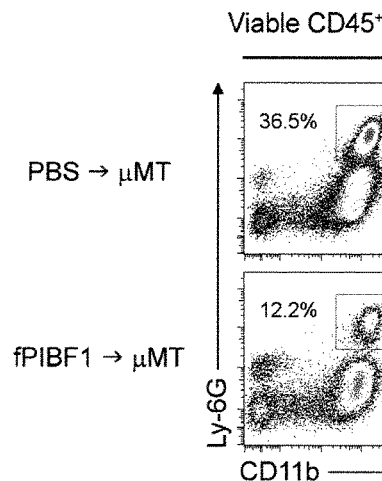
Figure 3M:
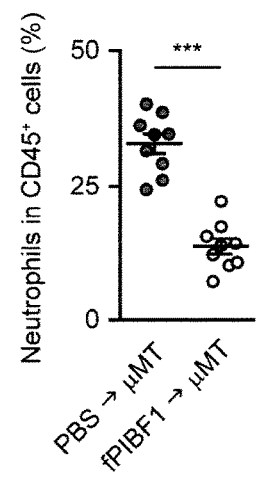
Figure 3N:
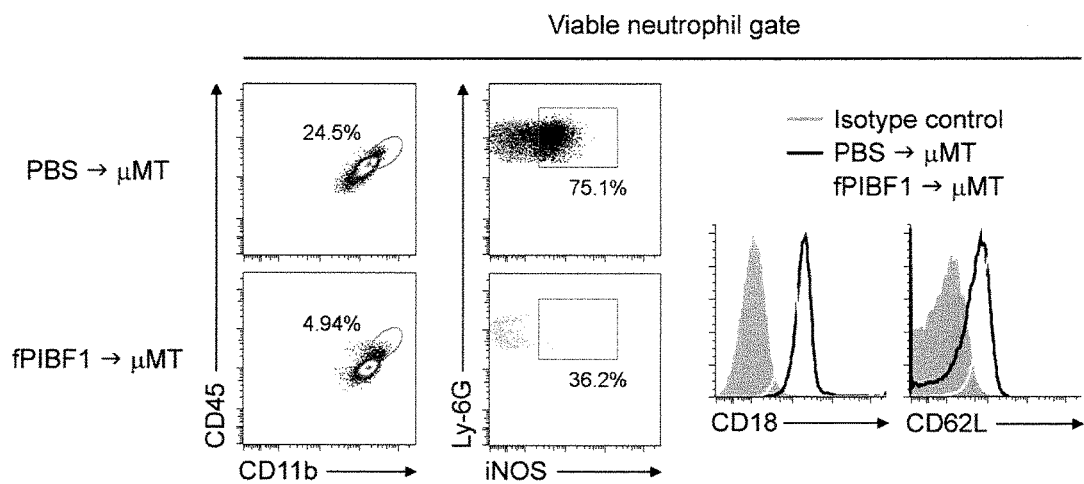
Figure 9A:
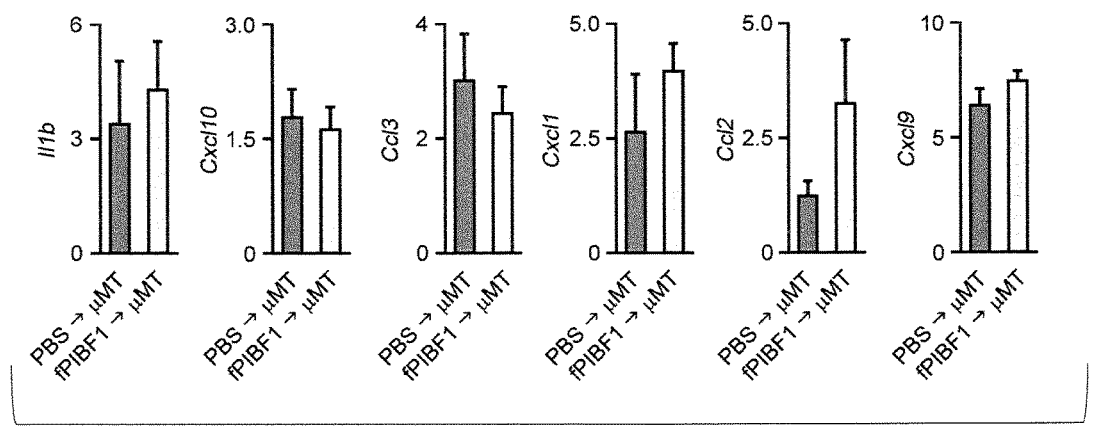
FIGS. 9A and 9B show that full-length PIBF1 administration reduces uterine inflammation and neutrophil activation in LPS-challenged pregnant μMT mice.
Figure 9B:
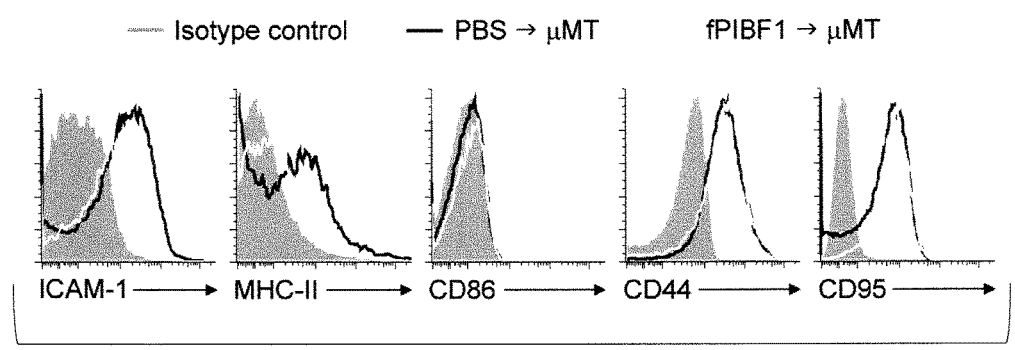
Figure 10A:
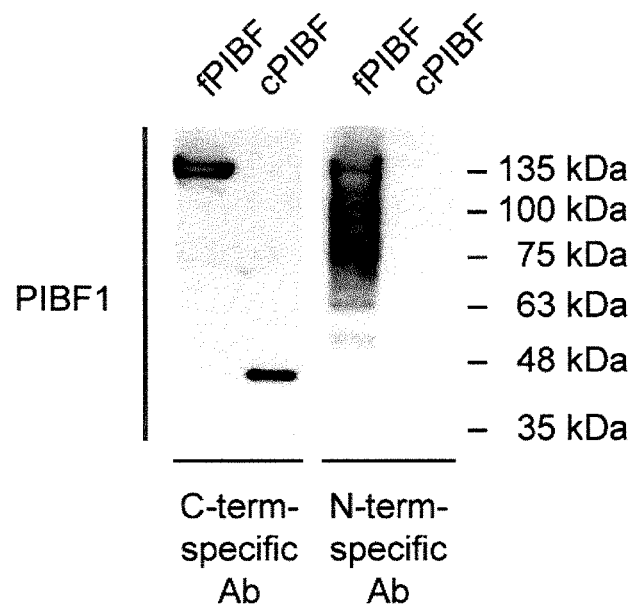
FIGS. 10A, 10B, 10C, 10D, 10E, and 10F demonstrate that a C-terminal fragment of PIBF1 does not protect μMT mice against LPS-induced PTL.
Figures 10B, 10C:
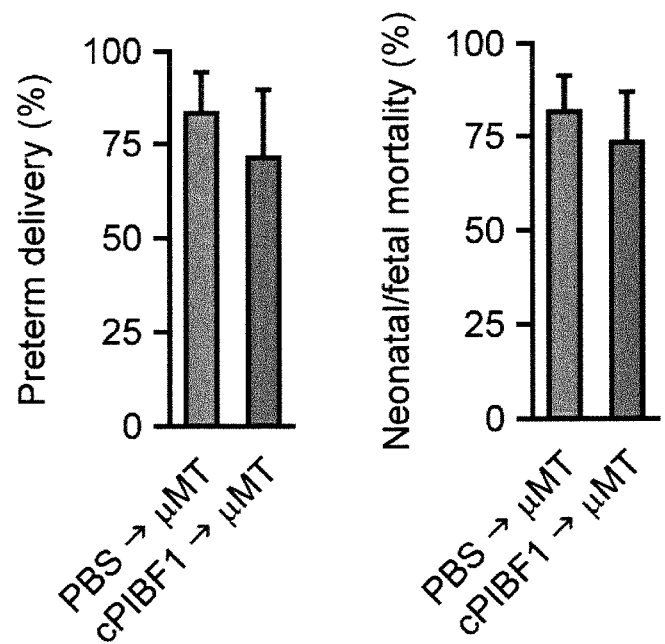
Figure 10D:
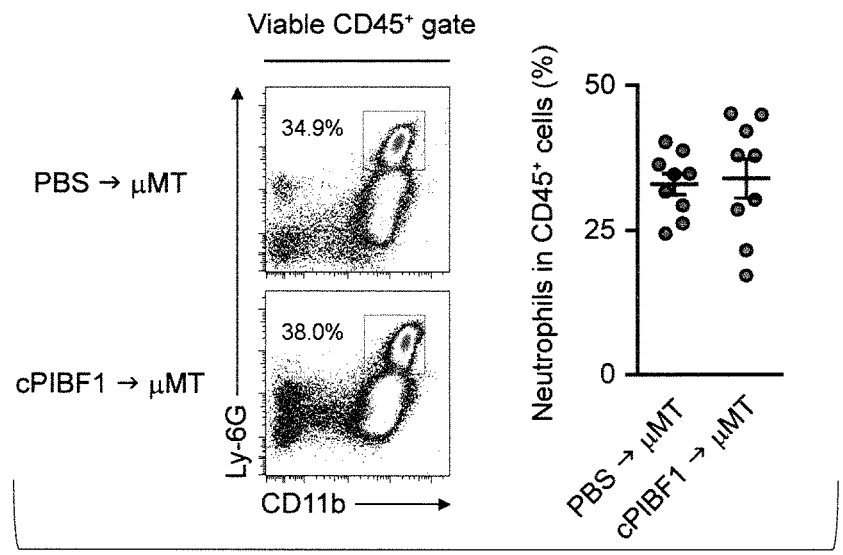
Figure 10E:
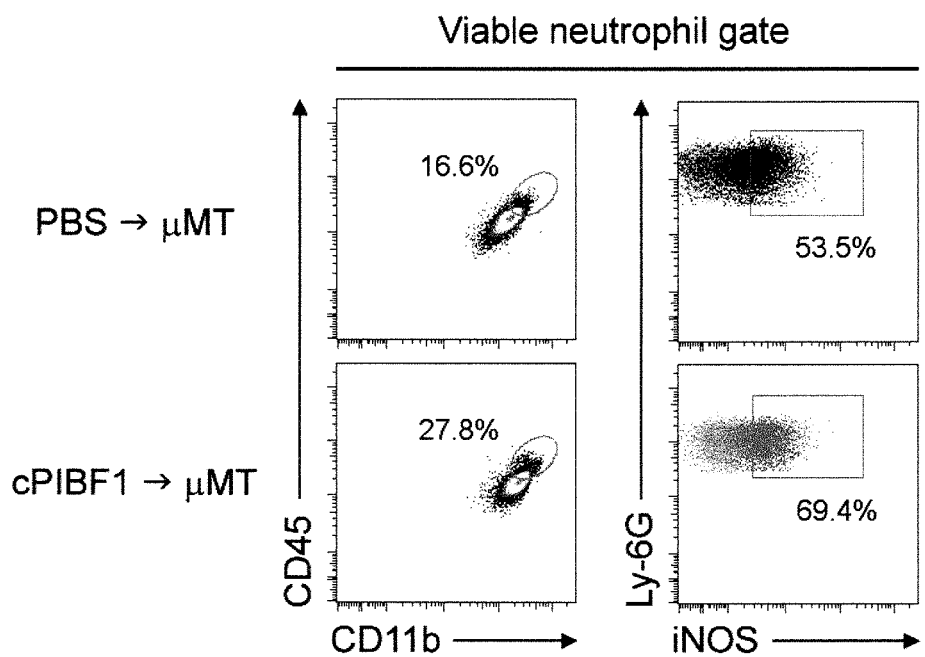
Figure 10F:
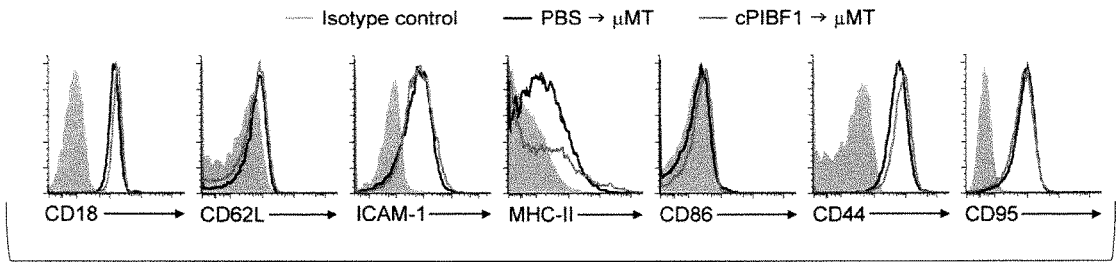

To test whether B cell-mediated protection against PTL was dependent on PIBF1 and whether therapeutic delivery of exogenous PIBF1 could restore resistance to PTL, μMT mice were administered with recombinant full-length PIBF1 (fPIBF1) before LPS challenge. fPIBF1 administration significantly reduced the rates of preterm delivery and neonatal/fetal mortality (FIGS. 3I and 3J), suppressed uterine induction of proinflammatory mediators (FIG. 3K and FIG. 9A) and inhibited neutrophil infiltration into the uterus (FIGS. 3L and 3M). Uterine neutrophils in fPIBF1-treated μMT mice exhibited reduced activation, with lower expression of CD11b, CD18, iNOS, ICAM-1 and MHC-II, and higher expression of CD62L (FIG. 3N and FIG. 9B). Administration of a recombinant C-terminal fragment of PIBF1 (cPIBF1) (FIG. 10A) neither mitigated PTL or neonatal/fetal death (FIGS. 10B and 10C) nor suppressed uterine neutrophil infiltration or activation (FIGS. 10D and 10E). Therefore, supplementation of PIBF1 is sufficient to restore resistance to PTL in μMT mice, and the protective activity of PIBF1 resides in its N-terminus. These data suggest that B cells protect against PTL via the provision of PIBF1.

Figure 11A:
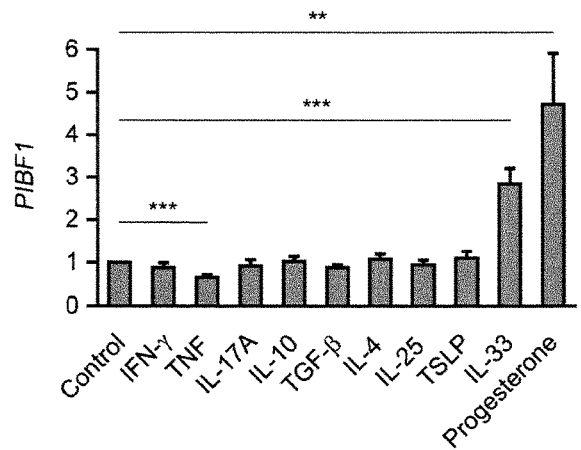
FIGS. 11A and 11B demonstrate that IFN-γ, TNF, IL-17A, IL-4, IL-10, TGF-β, IL-25 and TSLP do not induce PIBF1 expression by human B cells.
Figure 11B:
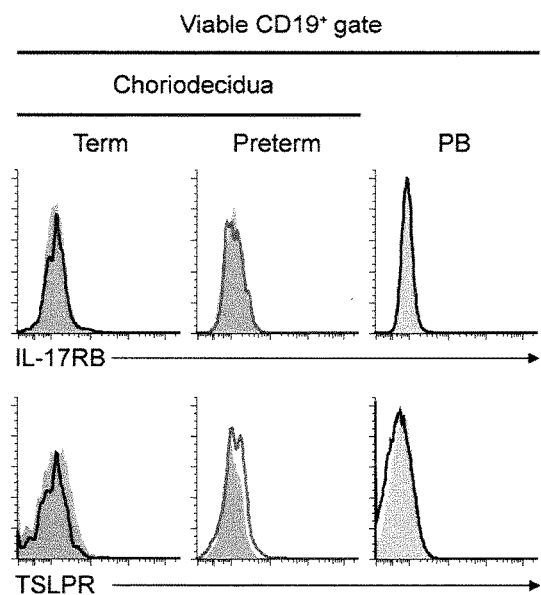

Regulation of PIBF1 expression by B cells was investigated and a panel of cytokines known to modulate B cell function was tested. qRT-PCR and Western Blot analyses showed that IL-33 promoted PIBF1 expression by human peripheral blood B cells (FIGS. 4A and 4B), similarly as progesterone, a known inducer of PIBF1. In contrast, interferon-γ (IFN-γ), IL-17A, IL-10 or TGF-β had no effect, and TNF had a suppressive effect (FIG. 11A). Of note, among the T helper type 2 (TH2) cytokines tested, including IL-4, IL-25, TSLP and IL-33, only IL-33 induced PIBF1 expression by B cells (FIG. 11A). Indeed, human peripheral blood or choriodecidual B cells do not express the receptor for IL-25 or TSLP (FIG. 11B). IL-33 also promotes PIBF1 expression by mouse uterine B cells during pregnancy, as evidenced by diminished PIBF1 in uterus and uterine B cells of IL-33−/− mice in late gestation (FIGS. 4C, 4D and FIGS. 12A, 12B, 12C, and 12D).

Figures 4C, 4D:
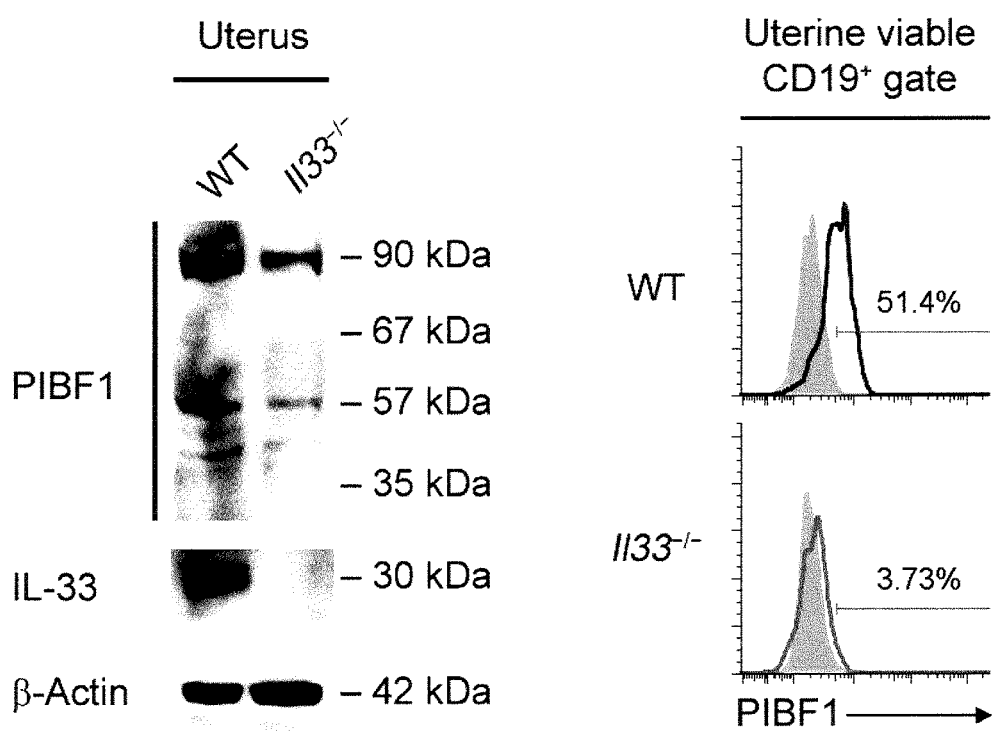
Figure 4E:
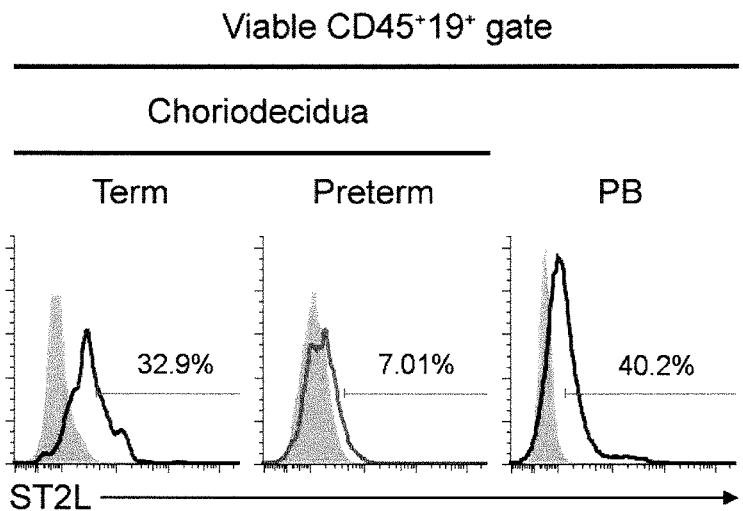
Figure 4F:
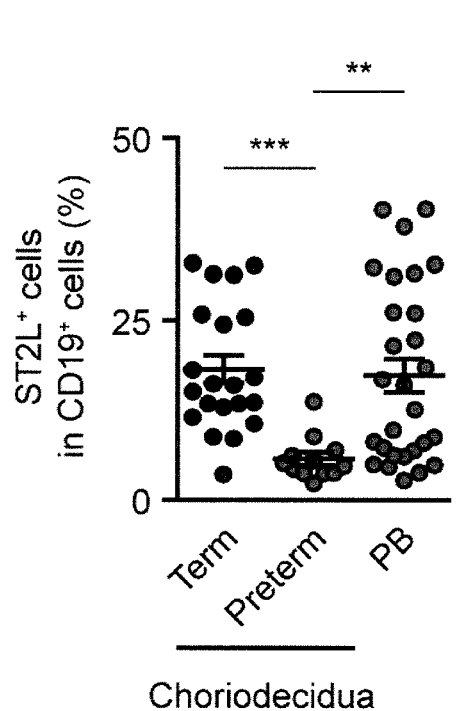
Figure 4G:
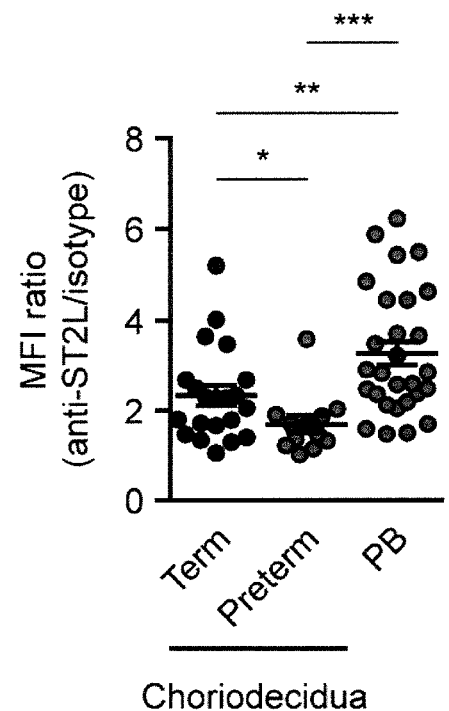
Figure 4H:
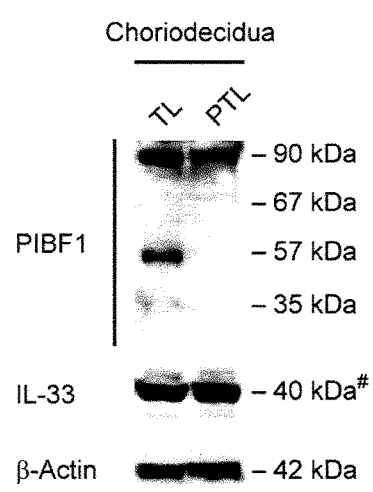
Figure 4I:
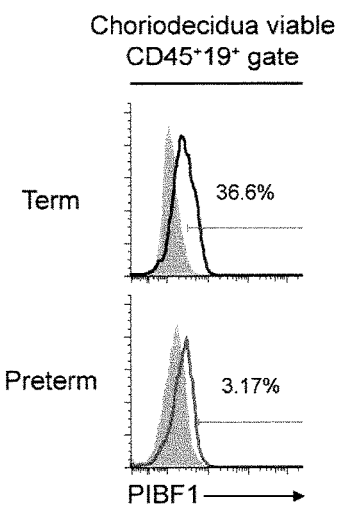
Figure 4J:
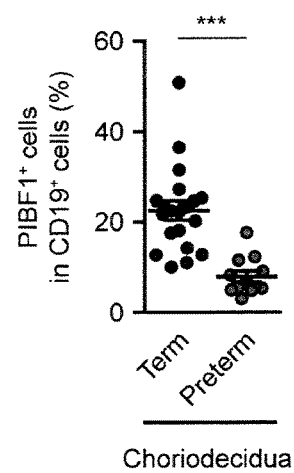
Figure 4K:
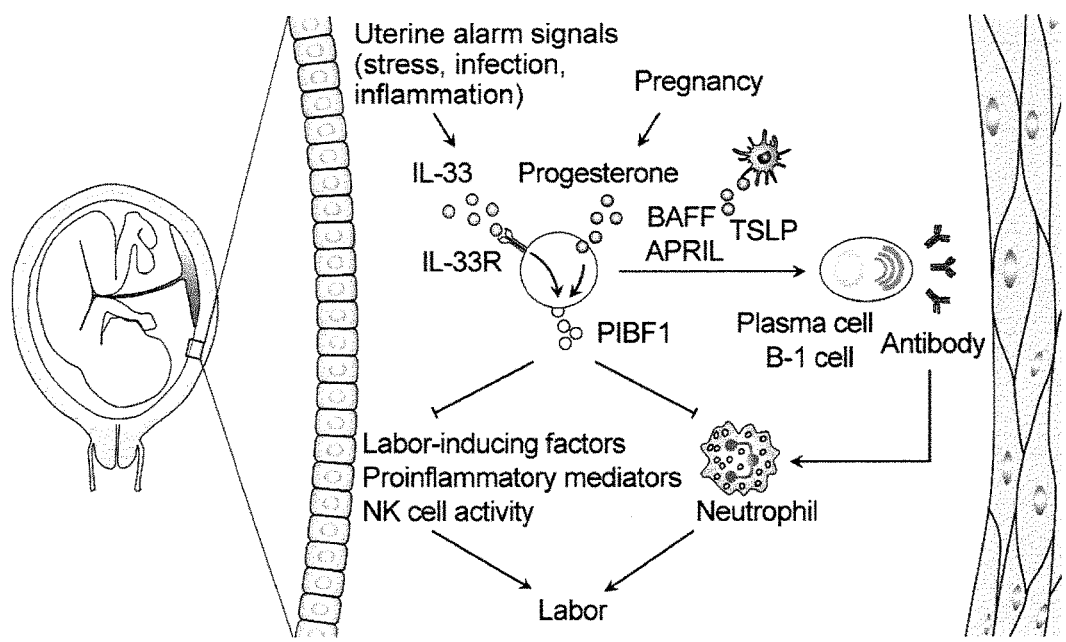
Figure 13A:
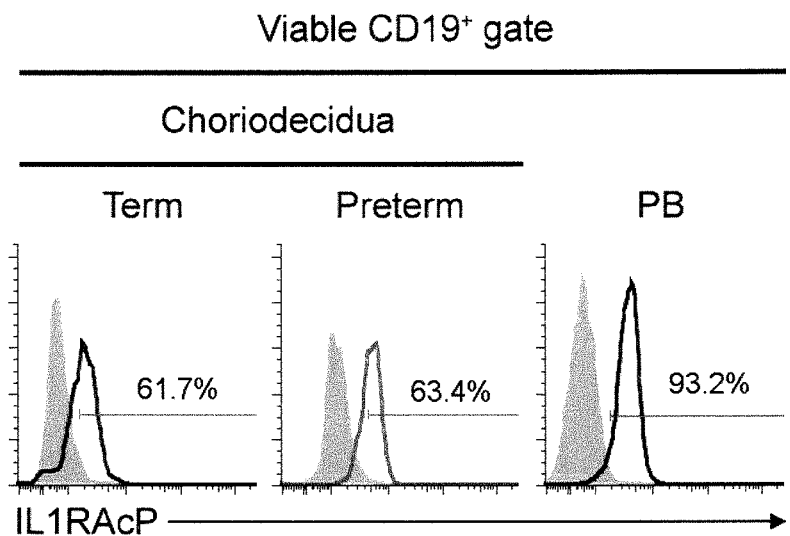
FIGS. 13A, 13B, and 13C demonstrate that peripheral blood and choriodecidual B cells constitutively express IL1RAcP.
Figure 13B:
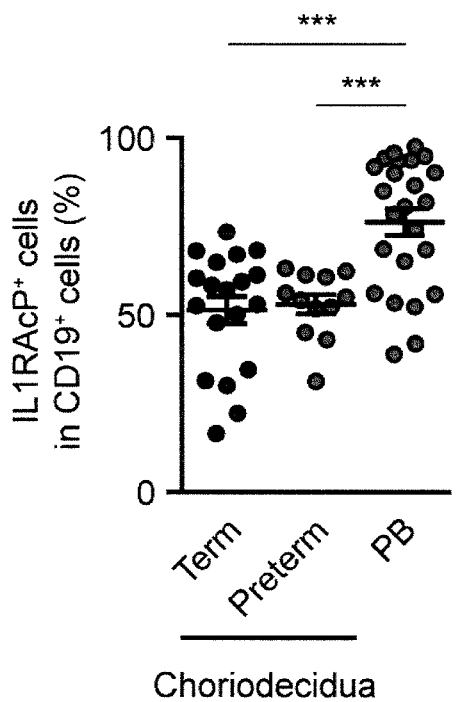
Figure 13C:
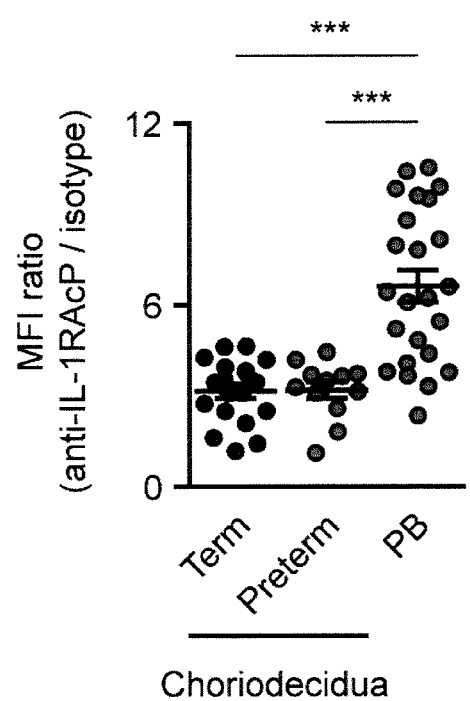

IL-33 is a mucosal alarmin that signals tissue damage following stress or infection and can induce immune cells with regulatory functions to maintain tissue homeostasis. Uterine stress and infection are causally linked to human PTL. While human peripheral blood and choriodecidual B cells constitutively expressed the β-chain of IL-33 receptor (IL-33R), interleukin-1 receptor accessory protein (IL1RAcP) (FIGS. 13A, 13B and 13C), the expression of the IL-33R α-chain, interleukin-1 receptor-like 1 (ST2L), was significantly diminished on choriodecidual B cells in PTL (FIGS. 4E, 4F and 4G). PIBF1 expression in choriodecidua and choriodecidual B cells of PTL patients was concomitantly diminished (FIGS. 4H, 4I, and 4J). Therefore, human PTL is associated with defects in IL-33 responsiveness of and PIBF1 production by choriodecidual B cells.

Tables

TABLE 1

Demographic and clinical characteristics of the study subjects‡

|  | Spontaneous TL (n = 30) | Spontaneous PTL (n = 15) | p |
|---|---|---|---|
| Maternal age (year) Median [interquartile range] | 27.5 [24.75-29] | 24 [23-28] | 0.202‡ |
| Race |  |  | 0.564# |
| African-American | 17 (56.6) | 10 (60) |  |
| White | 9 (30) | 3 (20) |  |
| Hispanic | 2 (6.7) | 2 (20) |  |
| Other | 2 (6.7) | 0 (0) |  |
| Gestational length (week) Median [interquartile range] | 39 [38-40] | 34 [33-35] | <0.0001$ |

‡Subjects with non-singleton gestation, current diagnosis of preeclampsia, a prior history or current diagnosis of diabetes, chronic hypertension, asthma, thyroid disease, pyelonephritis, active Chlamydia, Gonorrhea or Syphilis infections, active human papillomavirus (HPV) or herpes simplex virus (HSV) lesions, human immunodeficiency virus (HIV) infection and recreational drug use were excluded.
‡t-test.
$Kruskal - Wallis test.
Chi-squared test.

TABLE 2

Primers for human gene products

| Target gene | Sense (S) or Antisense (AS) | Primer sequence | SEQ ID NO: |
|---|---|---|---|
| GAPDH | S | 5'-GAAGGTGAAGGTCGGAGTC-3' | 13 |
|  | AS | 5'-GAAGATGGTGATGGGATTTC-3' | 14 |
| PIBF1 | S | 5'-CTTACAAAGATTGAAGAATTGGAGG-3' | 15 |
|  | AS | 5'-AATTCTTGATATTTGCTGGCATCTT-3' | 16 |
| TNFSF13 | S | 5'-CTGCACCTGGTTCCCATTAAC-3' | 17 |
|  | AS | 5'-AAGAGCTGGTTGCCACATCAC-3' | 18 |

TABLE 2-continued

Primers for human gene products

| Target gene | Sense (S) or Antisense (AS) | Primer sequence | SEQ ID NO: |
|---|---|---|---|
| TNFSF13B | S | 5'-ACCGCGGGACTGAAAATCT-3' | 19 |
|  | AS | 5'-CACGCTTATTTCTGCTGTTCTGA-3' | 20 |
| TSLP | S | 5'-CCCAGGCTATTCGGAAACTCAG-3' | 21 |
|  | AS | 5'-CGCCACAATCCTTGTAATTGTG-3' | 22 |

TABLE 3

Primers for mouse gene products

| Target gene | Sense (S) or Antisense (AS) | Primer sequence | SEQ ID NO: |
|---|---|---|---|
| Gapdh | S | 5'-AGGTCGGTGTGAACGGATTTG-3' | 23 |
|  | AS | 5'-TGTAGACCATGTAGTTGAGGTCA-3' | 24 |
| Tnf | S | 5'-GGAACACGTCGTGGGATAATG-3' | 25 |
|  | AS | 5'-GGCAGACTTTGGATGCTTCTT-3' | 26 |
| Il1b | S | 5'-GCAACTGTTCCTGAACTCAACT-3' | 27 |
|  | AS | 5'-ATCTTTTGGGGTCCGTCAACT-3' | 28 |
| Il6 | S | 5'-TAGTCCTTCCTACCCCAATTTCC-3' | 29 |
|  | AS | 5'-TTGGTCCTTAGCCACTCCTTC-3' | 30 |
| Mmp9 | S | 5'-GGACCCGAAGCGGACATTG-3' | 31 |
|  | AS | 5'-CGTCGTCGAAATGGGCATCT-3' | 32 |
| CXCl1 | S | 5'-CTGGGATTCACCTCAAGAACATC-3' | 33 |
|  | AS | 5'-CAGGGTCAAGGCAAGCCTC-3' | 34 |
| Cxcl5 | S | 5'-GCGGCTATGACTGAGGAAGG-3' | 35 |
|  | AS | 5'-GTTCCATCTCGCCATTCATGC-3' | 36 |
| Pibf1 | S | 5'-GCTGACAGAAGAGCAGTATG-3' | 37 |
|  | AS | 5'-CGAGCTCATAGAAGCGAATAG-3' | 38 |
| Cxcl2 | S | 5'-CCAACCACCAGGCTACAGG-3' | 39 |
|  | AS | 5'-GCGTCACACTCAAGCTCTG-3' | 40 |
| Ccl3 | S | 5'-TTCTCTGTACCATGACACTCTGC-3' | 41 |
|  | AS | 5'-CGTGGAATCTTCCGGCTGTAG-3' | 42 |
| Cxcl10 | S | 5'-CCAAGTGCTGCCGTCATTTTC-3' | 43 |
|  | AS | 5'-GGCTCGCAGGGATGATTTCAA-3' | 44 |
| Ccl2 | S | 5'-TTAAAAACCTGGATCGGAACCAA-3' | 45 |
|  | AS | 5'-GCATTAGCTTCAGATTTACGGGT-3' | 46 |
| Cxcl9 | S | 5'-TCCTTTTGGGCATCATCTTCC-3' | 47 |
|  | AS | 5'-TTTGTAGTGGATCGTGCCTCG-3' | 48 |
| Ebi3 | S | 5'-CTCTCCCCTGGTTACACTG-3' | 49 |
|  | AS | 5'-CCACGGGATACCGAGAAGC-3' | 50 |
| Il10 | S | 5'-GCTCTTACTGACTGGCATGAG-3' | 51 |
|  | AS | 5'-CGCAGCTCTAGGAGCATGTG-3' | 52 |
| Tgfb1 | S | 5'-CTTCAATACGTCAGACATTCGGG-3' | 53 |
|  | AS | 5'-GTAACGCCAGGAATTGTTGCTA-3' | 54 |

TABLE 4

Antibodies to human antigens

| Antigen | Conjugation | Isotype | Clone | Manufacturer | Use |
|---|---|---|---|---|---|
| APRIL | — | Goat IgG | — | Santa Cruz sc-5737 | IF |
| BAFF | PE | Mouse IgG1 | 1D6 | eBioscience 12-9017 | IF |
| BAFFR | PE | Mouse IgG1 | 11C1 | Biolegend 316906 | FC |
| BCMA | PE | Goat IgG | — | R&D FAB193P | FC |
| CCR10 | APC | Rat IgG2a | 314305 | R&D FAB3478A | FC |
| CCR6 | PE | Mouse IgG2b | G034E3 | Biolegend 353409 | FC |
| CCR7 | PE-Cy7 | Rat IgG2a | 3D12 | BD 557648 | FC |
| CCR9 | AF647 | Mouse IgG2a | BL/CCR9 | Biolegend 346301 | FC |
| CD10 | PE | Mouse IgG1 | MEM-78 | Thermo Fisher Scientific CD1004 | FC |
| CD11c | PE | Mouse IgG1 | B-ly6 | BD 555392 | FC |
| CD138 | PE | Mouse IgG1 | DL-101 | BD 555805 | FC |
| CD19 | APC-Cy7 | Mouse IgG1 | HIB19 | Biolegend 302218 | FC |
|  | PE-Cy7 | Mouse IgG1 | HIB19 | eBioscience 25-0199 | FC |
|  | Biotin | Mouse IgG1 | HIB19 | Biolegend 302204 | MACS, IF, IHC |
|  | PE-CF594 | Mouse IgG1 | HIB19 | BD 562321 | FC |
|  | QDot655 | Mouse IgG1 | SJ25C1 | Thermo Fisher Scientific Q10179 | FC |
| CD1d | PE | Mouse IgG2b | 51.1 | Biolegend 350305 | FC |
| CD20 | PE-Cy7 | Mouse IgG2b | 2H7 | Biolegend 302312 | FC |
|  | APC | Mouse IgG2b | 2H7 | Biolegend 302310 | FC |
| CD22 | PE | Mouse IgG2b | S-HCL-1 | BD 347577 | FC |
| CD23 | FITC | Mouse IgG1 | 9P25 | Beckman Coulter IM0529 | FC |
| CD24 | PE | Mouse IgG2a | ML5 | BD 555428 | FC |
|  | APC-eF780 | Mouse IgG1 | eBioSN3 | eBioscience 47-0247 | FC |
| CD25 | FITC | Mouse IgG1 | M-A251 | BD 555431 | FC |
| CD27 | AF647 | Mouse IgG1 | O323 | Biolegend 302812 | FC |
|  | PE | Mouse IgG1 | M-T271 | BD 555441 | FC |
| CD38 | PE-Cy7 | Mouse IgG1 | HIT2 | Biolegend 303510 | FC |
|  | APC | Mouse IgG1 | HIT2 | Biolegend 303516 | FC |
| CD40 | FITC | Mouse IgG1 | 5C3 | Biolegend 334305 | FC |
| CD43 | FITC | Mouse IgG1 | 84-3C1 | eBioscience 11-0439 | FC |
| CD44 | PE | Rat IgG2b | IM7 | Biolegend 103009 | FC |
| CD45 | eF450 | Mouse IgG1 | 2D1 | eBioscience 48-9459 | FC |
| CD5 | PE | Mouse IgG1 | UCHT2 | BD 555353 | FC |
| CD69 | PE | Mouse IgG1 | FN50 | BD 555531 | FC |
| CD70 | PE | Mouse IgG1 | 113-16 | Biolegend 355103 | FC |
| CD80 | PE | Mouse IgG1 | L307.4 | BD 557227 | FC |
| CD86 | PE | Mouse IgG1 | FUN-1 | BD 555658 | FC |
| CD95 | PE | Mouse IgG1 | DX2 | BD 555674 | FC |
| Cytokeratin-7 | — | Mouse IgG1 | RCK105 | Abcam ab9021 | IF |
| GAPDH | — | Mouse IgG | — | Bioss bsm-0978M | WB |
| IgD | Biotin | Goat IgG F(ab)$_2$ | — | Southern Biotech 2032-08 | FC, MACS |
|  | FITC | Mouse IgG2a | IA6-2 | BD 555778 | FC |
| IgM | FITC | Goat IgG F(ab)$_2$ | — | Thermo Fisher Scientific AHI1608 | FC |
| IL-10 | PE | Rat IgG1 | JES3-9D7 | eBioscience 12-7108 | FC |
| IL-17RB | AF488 | Rabbit IgG | — | Bioss bs-2610R-FITC | FC |
| IL1RAcP | PE | Recombinant Human IgG | REA558 | Miltenyi Biotec 130-108-756 | FC |
| IL-33 | — | Mouse IgG1 | 12B3C4 | Thermo Fisher Scientific MA5-15772 | WB |
| PD-L1 | FITC | Mouse IgG1 | MIH1 | BD 558065 | FC |
| PIBF1 | — | Sheep IgG | — | R&D AF5559 | WB, FC |
|  | — | Rabbit IgG | — | Antibodies-online ABIN2426350 | WB (FIG. 10A only) |
| ST2 | — | Goat IgG | — | R&D AF523SP | WB |
| ST2L | FITC | Mouse IgG1 | B4E6 | MDBioproducts 101002F | FC |
| TACI | PE | Mouse IgG1 | 165604 | R&D FAB1741P | FC |
| TSLP | — | Rabbit IgG | — | Rockland 600-401-FR6 | IF |
| TSLPR | PE | Mouse IgG1 | 1B4 | Biolegend 322806 | FC |
| $\alpha_4$ integrin | APC | Mouse IgG1 | 9F10 | Biolegend 304308 | FC |
| $\beta_7$ integrin | eF650NC | Rat IgG2a | FIB504 | eBioscience 95-5867 | FC |
| $\beta$-Actin | — | Mouse IgG1 | AC-15 | Sigma Aldrich A5441 | WB |

TABLE 5

Antibodies to mouse antigens

| Antigen | Conjugation | Isotype | Clone | Manufacturer | Use |
|---|---|---|---|---|---|
| B220 | APC-Cy7 | Rat IgG2a | RA3-6B2 | Biolegend 103224 | FC |
| CD11b | APC-Cy7 | Rat IgG2b | M1/70 | Biolegend 101226 | FC |
| CD11c | PE-Cy7 | Hamster IgG | N418 | Tonbo Biosciences 60-0114 | FC |
| CD16/CD32 | — | Rat IgG2b | 2.4G2 | Tonbo Biosciences 70-0161, BD Biosciences 553141 | Fc Block |

TABLE 5-continued

Antibodies to mouse antigens

| Antigen | Conjugation | Isotype | Clone | Manufacturer | Use |
| --- | --- | --- | --- | --- | --- |
| CD18 | PerCP-Cy5.5 | Rat IgG1 | H155-78 | Biolegend 141007 | FC |
| CD19 | PE-CF594 | Rat IgG2a | 1D3 | BD 562291 | FC |
| | BV650 | Rat IgG2a | 6D5 | Biolegend 115541 | FC |
| | FITC | Rat IgG2a | 1D3 | Tonbo Biosciences 35-0193 | FC |
| CD3 | APC-Cy7 | Rat IgG2b | 17A2 | Tonbo Biosciences 25-0032 | FC |
| CD44 | PE-Cy7 | Rat IgG2b | IM7 | BD 560569 | FC |
| CD45 | violetFluor450 | Rat IgG2b | 30-F11 | Tonbo Biosciences 75-0451 | FC |
| CD62L | PE-Cy7 | Rat IgG2a | MEL-14 | Biolegend 104418 | FC |
| CD86 | AF700 | Rat IgG2a | GL-1 | Biolegend 105024 | FC |
| CD95 | PE | Hamster IgG2 | Jo2 | BD 554258 | FC |
| F4/80 | PE | Rat IgG2a | BM8 | eBioscience 12-4801 | FC |
| ICAM-1 | Biotin | Rat IgG2b | YN1/1.7.4 | Biolegend 116103 | FC |
| IL-10 | PE | Rat IgG2b | JES6-16E3 | eBioscience 12-7101 | FC |
| IL-33 | — | Rabbit IgG | 13H20L1 | Thermo Fisher Scientific 700268 | WB |
| iNOS | PE | Rat IgG2a | CXNFT | eBioscience 12-5920 | FC |
| Ly-6C | PerCP-Cy5.5 | Rat IgG2c | HK1.4 | Biolegend 128012 | FC |
| Ly-6G | FITC | Rat IgG2a | 1A8 | Tonbo Biosciences 35-1276 | FC |
| MHC-II (I/A-I/E) | Biotin | Rat IgG2b | M5/114.15.2 | Biolegend 107603 | FC |
| NK1.1 | PE-Cy7 | Mouse IgG2a | PK136 | Biolegend 108718 | FC |
| | FITC | Mouse IgG2a | PK136 | Biolegend 108714 | FC |
| PIBF1 | — | Sheep IgG | — | R&D AF5559 | WB, FC |
| β-Actin | — | Mouse IgG1 | AC-15 | Sigma-Aldrich A5441 | WB |

TABLE 6

Isotype control and secondary antibodies used in this study

| Isotype | Conjugation | Clone | Manufacturer | Use |
| --- | --- | --- | --- | --- |
| Goat IgG | — | — | Santa Cruz sc-2028 | IF |
| | PE | Poly24030 | Biolegend 403004 | FC |
| Goat IgG F(ab')$_2$ | Biotin | — | Southern Biotech 0110-08 | FC |
| | FITC | — | Southern Biotech 0110-02 | FC |
| Hamster IgG2 | PE | B81-3 | BD 550085 | FC |
| Mouse IgG1 | — | MOPC-21 | BD 556648 | IF |
| | AF647 | MOPC-21 | Biolegend 400155 | FC |
| | APC | MOPC-21 | BD 555751, Biolegend 400120 | FC |
| | Biotin | MOPC-21 | Biolegend 400103 | FC, IF, IHC |
| | FITC | MOPC-21 | BD 555748 | FC |
| | PE | MOPC-21 | BD 555749 | FC |
| | PE-Cy7 | MOPC-21 | BD 555872, Biolegend 400126 | FC |
| Mouse IgG2a | AF647 | MOPC-173 | Biolegend 400234 | FC |
| | FITC | X39 | BD 349051 | FC |
| | PE | MOPC-173 | Biolegend 400212 | FC |
| Mouse IgG2b | FITC | MPC-11 | Biolegend 400310 | FC |
| | APC | 27-35 | BD 555745 | FC |
| | PE | eBMG2b | eBioscience 12-4732 | FC |
| | PE-Cy7 | MPC-11 | Biolegend 400326 | FC |
| | APC-eF780 | eBMG2b | eBioscience 47-4732 | FC |
| Rabbit IgG | — | — | Santa Cruz sc-2027 | IF |
| | FITC | — | Bioss bs-0295P-FITC | FC |
| Rat IgG1 | PE | eBRG1 | eBioscience 12-4301 | FC |
| | PerCP-Cy5.5 | A110-1 | BD 551072 | FC |
| Rat IgG2a | AF700 | RTK4530 | Biolegend 400628 | FC |
| | APC | RTK2758 | Biolegend 400511 | FC |
| | eF660 | eB149/10H5 | eBioscience 50-4031 | FC |
| | FITC | R35-95 | BD 554688 | FC |
| | PE | eBR2a | eBioscience 12-4321 | FC |
| | PE-Cy7 | RTK2758 | Biolegend 400521 | FC |
| Rat IgG2b | Biotin | RTK4530 | Biolegend 400603 | FC |
| | PE | A95-1 | BD 553989 | FC |
| | PE-Cy7 | RTK4530 | Biolegend 400617 | FC |
| Recombinant human IgG | PE | REA293 | Miltenyi Biotec 130-104-613 | FC |
| Sheep IgG | — | — | R&D 5-001-A | FC, IF |

| Secondary antibody/reagent | Conjugation | Manufacturer | Use |
| --- | --- | --- | --- |
| Anti-biotin IgG | Magnetic microbeads | Miltenyi Biotec 130-090-485 | MACS |
| Donkey anti-goat IgG | HRP | Santa Cruz sc-2020 | WB |
| Donkey anti-mouse IgG | AF594 | Thermo Fisher Scientific A21203 | IF |
| | CF647 | Sigma-Aldrich SAB4600176 | IF |
| | HRP | Santa Cruz sc-2318 | WB |

TABLE 6-continued

| Isotype control and secondary antibodies used in this study | | | |
|---|---|---|---|
| Donkey anti-sheep IgG | HRP | Santa Cruz sc-2473 | WB |
| Donkey F(ab')₂ anti-sheep IgG | AF647 | Jackson Immunoresearch 713-606-147 | IF |
| Goat F(ab')₂ anti-mouse IgG | Cy3 | Jackson Immunoresearch 115-166-006 | IF |
|  | FITC | Southern Biotech 1032-02 | IF |
| Goat F(ab')₂ anti-rabbit IgG | Cy3 | Jackson Immunoresearch 111-166-047 | IF |
| Goat anti-rabbit IgG | HRP | Santa Cruz sc-2004 | WB |
| Streptavidin | AF488 | Thermo Fisher Scientific S11223 | FC, IF |
|  | AF647 | Thermo Fisher Scientific S21374 | FC, IF |
|  | HRP | R&D 890803 | IHC |
|  | PerCP-Cy5.5 | BD 551419 | FC |
|  | QDot605 | Thermo Fisher Scientific Q10101MP | FC |

Sequences

Human PIBF1 is disclosed herein as SEQ ID NO: 1:
MSRKISKESKKVNISSSLESEDISLETTVPTDDISSSEEREGKVRITRQLIERKELLHNIQLLK
IELSQKTMMIDNLKVDYLTKIEELEEKLNDALHQKQLLTLRLDNQLAFQQKDASKYQELMKQEM
ETILLRQKQLEETNLQLREKAGDVRRNLRDFELTEEQYIKLKAFPEDQLSIPEYVSVRFYELVN
PLRKEICELQVKKNILAEELSTNKNQLKQLTETYEEDRKNYSEVQIRCQRLALELADTKQLIQQ
GDYRQENYDKVKSERDALEQEVIELRRKHEILEASHMIQTKERSELSKEVVTLEQTVTLLQKDK
EYLNRQNMELSVRCAHEEDRLERLQAQLEESKKAREEMYEKYVASRDHYKTEYENKLHDELEQI
RLKTNQEIDQLRNASREMYERENRNLREARDNAVAEKERAVMAEKDALEKHDQLLDRYRELQLS
TESKVTEFLHQSKLKSFESERVQLLQEETARNLTQCQLECEKYQKKLEVLTKEFYSLQASSEKR
ITELQAQNSEHQARLDIYEKLEKELDEIIMQTAEIENEDEAERVLFSYGYGANVPTTAKRRLKQ
SVHLARRVLQLEKQNSLILKDLEHRKDQVTQLSQELDRANSLLNQTQQPYRYLIESVRQRDSKI
DSLTESIAQLEKDVSNLNKEKSALLQTKNQMALDLEQLLNHREELAAMKQILVKMHSKHSENSL
LLTKTEPKHVTENQKSKTLNVPKEHEDNIFTPKPTLFTKKEAPEWSKKQKMKT (SEQ ID NO. 1)

A functional fragment of PIBF1 effective to prevent and/or inhibit preterm
labor in a pregnant subject-SEQ ID NO: 2:
MSRKISKESKKVNISSSLESEDISLETTVPTDDISSSEEREGKVRITRQLIERKELLHNIQLLK
IELSQKTMMIDNLKVDYLTKIEELEEKLNDALHQKQLLTLRLDNQLAFQQKDASKYQELMKQEM
ETILLRQKQLEETNLQLREKAGDVRRNLRDFELTEEQYIKLKAFPEDQLSIPEYVSVRFYELVN
PLRKEICELQVKKNILAEELSTNKNQLKQLTETYEEDRKNYSEVQIRCQRLALELADTKQLIQQ
GDYRQENYDKVKSERDALEQEVIELRRKHEILEASHMIQTKERSELSKEVVTLEQTVTLLQKDK
EYLNRQNMELSVRCAHEEDRLERLQAQLEESKKAREEMYEKYVASRDHYKTEYENKLHDELEQI
RLKTNQEIDQLRNASREMYERENRNLREARDNAVAEKERAVMAEKDALEKHDQLLDRYRELQLS
TESKVTEFLHQSKLKSFESERVQLLQEETARNLTQCQLECEKYQKKLEVLTKEFYSLQASSEKR
ITELQAQNSEHQARLDIYEKLEKELDEIIMQTAEIENEDEAERVLFSYGYGANVPTTAKRRLKQ
SVHLARRVLQLEKQNSLILKDLEHRKDQVTQLSQELDRANSLLNQTQQPYRYLIESVRQRDSKI
DSLTESIAQLEKDVSNLNK (SEQ ID NO: 2)

PIBF1 of SEQ ID NO: 1 is encoded by SEQ ID NO: 3:
atgtctcgaaaaatttcaaaggagtcaaaaaaagtgaacatctctagttctctggaatctgaag
atattagtttagaaacaacagttcctacggatgatatttcctcatcagaagagcgagagggcaa
agtcagaatcaccaggcagctaattgaacgaaaagaactacttcataatattcagttactaaaa
attgagctatcccagaaaactatgatgatcgacaatttgaagtggattatcttacaaagattg
aagaattggaggagaaacttaatgatgcacttcaccagaagcagctactaacattgagattaga
caaccaattggcttttcaacagaaagatgccagcaaatatcaagaaatactagaaccaagaaat
gaaaccatttttgttgagacagaaacaactagaagagacaaatcttcagctaagagaaaagctg
gagatgttcgtcgaaacctgcgtgactttgagttgacagaagagcaatatattaaattaaaagc
ttttcctgaagatcagctttctattcctgaatatgtatctgttcgcttctatgagctagtgaat
ccattaagaaaggaaatctgtgaactacaagtgaaaaagaaattcctagcagaagaattaagta
caaacaaaaccaactgaagcagctgacagagacatatgaggaagatcgaaaaaactactctga
agttcaaattagatgtcaacgtttggccttagaattagcagacaaaacagttaattcagcaa
ggtgactaccgtcaagagaactatgataaagtcaagagtgaacgtgatgcacttgaacaggaag
taattgagcttaggagaaaacatgaaatacttgaagcctctcacatgattcaaacaaaagaacg
aagtgaattatcaaaagaggtagtcaccttagagcaaactgttactttactgcaaaaggataaa
gaatatcttaatcgccaaaacatggagcttagtgttcgctgtgctcatgaagaggatcgccttg
aaagacttcaagctcaactggaagaaagcaaaaaggctagagaagagatgtatgaaaaatatgt
agcatccagagaccattataaaacagaatatgaaaataaactacatgatgaactagaacaaatc
agattgaaaaccaaccaagaaattgatcaacttcgaaatgcctctagggaaatgtatgaacgag
aaaacagaaatctccgagaagcaagggataatgctgtggctgaaaaggaacgagcagtgatggc
tgaaaaggatgcttagaaaaacacgatcagctcttagacaggtacagagaactacaacttagt
acagaaagcaaagtaacagaatttctccatcaaagtaaattaaaatctttgaaagtgagcgtg
ttcaacttctgcaagaggaaacagcaagaaatctcacacagtgtcaattggaatgtgaaaaata
tcagaaaaaattggaggttttaaccaaagaattttatagtctccaagcctcttctgaaaaacgc
attactgaacttcaagcacagaactcagagcatcaagcaaggctagacatttatgagaaactgg
aaaaagagcttgatgaaataataatgcaaactgcagaaattgaaaatgaagatgaggctgaaag
ggttcttttttcctacggctatggtgctaatgttcccacaacagccaaaagacgactaaagcaa
agtgttcacttggcaagaagagtgcttcaattagaaaaacaaaactcgctgattttaaaagatc
tggaacatcgaaaggaccaagtaacacagctttcacaagagcttgacagagccaattcgctatt
aaaccagactcaacagcct tacaggtatctcattgaatcagtgcgtcagagagattctaagatt
gattcactgacggaatctattgcacaacttgagaaagatgtcagcaacttaaataaagaaagt

```
cagctttactacagacgaagaatcaaatggcattagatttagaacaacttctaaatcatcgtga
ggaattggcagcaatgaaacagattctcgttaagatgcatagtaaacattctgagaacagctta
cttctcactaaaacagaaccaaaacatgtgacagaaaatcagaaatcaaagactttgaatgtgc
ctaaagagcatgaagacaatatatttacacctaaaccaacactctttactaaaaaagaagcacc
tgagtggtctaagaaacaaaagatgaagacctag PIBF1 functional fragment of SEQ ID NO: 2 is encoded by SEQ ID NO: 4:
atgtctcgaaaaatttcaaaggagtcaaaaaaagtgaacatctctagttctctggaatctgaag
atattagtttagaaacaacagttcctacggatgatatttcctcatcagaagagcgagagggcaa
agtcagaatcaccaggcagctaattgaacgaaaagaactacttcataatattcagttactaaaa
attgagctatcccagaaaactatgatgatcgacaatttgaaagtggattatcttacaaagattg
aagaattggaggagaaacttaatgatgcacttcaccagaagcagctactaacattgagattaga
caaccaattggcttttcaacagaaagatgccagcaaatatcaagaattaatgaaacaagaaatg
gaaccattttgttgagacagaaacaactagaagagacaaatcttcagctaagagaaaaagctg
gagatgttcgtcgaaacctgcgtgactttgagttgacagaagagcaatatattaaattaaaagc
ttttcctgaagatcagctttctattcctgaatatgtatctgttcgcttctatgagctagtgaat
ccattaagaaaggaaatctgtgaactacaagtgaaaaagaatatcctagcagaagaattaagta
caaacaaaaaccaactgaagcagctgacagagacatatgaggaagatcgaaaaaactactctga
agttcaaattagatgtcaacgtttggcctagaattagcagacacaaaacagttaattcagcaa
ggtgactaccgtcaagagaactatgataaagtcaagagtgaacgtgatgcacttgaacaggaag
taattgagcttaggagaaaacatgaaatacttgaagcctctcacatgattcaaacaaaagaacg
aagtgaattatcaaagagggtagtcaccttagagcaaactgttactttactgcaaaaggataaa
gaatatcttaatcgccaaaacatggagcttagtgttcgctgtgctcatgaagaggatcgccttg
aaagacttcaagctcaactggaagaaagcaaaaaggctagagaagagatgtatgaaaaatatgt
agcatccagagaccattataaaacagaatatgaaaataaactacatgatgaactagaacaaatc
agattgaaaaccaaccaagaaattgatcaacttcgaaatgcctctagggaaatgtatgaacgag
aaaacagaaatctccgagaagcaagggataatgctgtggctgaaaaggaacgagcagtgatggc
tgaaaaggatgctttagaaaaacacgatcagctcttagacaggtacagagaactacaacttagt
acagaaagcaaagtaacagaatttctccatcaaagtaaattaaaatctttttgaaagtgagcgtg
ttcaacttctgcaagaggaaacagcaagaaatctcacacagtgtcaattggaatgtgaaaaata
tcagaaaaaattggaggttttaaccaaagaattttatagtctccaagcctcttctgaaaaacgc
attactgaacttcaagcacagaactcagagcatcaagcaaggctagacatttatgagaaactgg
aaaaagagcttgatgaaataataatgcaaactgcagaaattgaaaatgaagatgaggctgaaag
ggttctttttttcctacggctatggtgctaatgttcccacaacagccaaaagacgactaaagcaa
agtgttcacttggcaagaagagtgcttcaattagaaaaacaaaactcgctgattttaaaagatc
tggaacatcgaaaggaccaagtaacacagctttcacaagagcttgacagagccaattcgctatt
aaaccagactcaacagccttacaggtatctcattgaatcagtgcgtcagagagattctaagatt
gattcactgacggaatctattgcacaacttgagaaagatgtcagcaacttaaataaa (SEQ ID
NO: 4)

Human IL-33-SEQ ID NO: 5:
MKPKMKYSTNKISTAKWKNTASKALCFKLGKSQQKAKEVCPMYFMKLRSGLMIKKEACYFRRET
TKRPSLKTGRKHKRHLVLAACQQQSTVECFAFGISGVQKYTRALHDSSITGISPITEYLASLST
YNDQSITFALEDESYEIYVEDLKKDEKKDKVLLSYYESQHPSNESGDGVDGKMLMVTLSPTKDF
WLHANNKEHSVELHKCEKPLPDQAFFVLHNMSHNCVSFECKTDPGVFIGVKDNHLALIKVDSSE
NLCTENILFKLSET (SEQ ID NO. 5)

Mouse IL-33-SEQ ID NO: 6:
MRPRMKYSNSKISPAKFSSTAGEALVPPCKIRRSQQKTKEFCHVYCMRLRSGLTIRKETSYFRK
EPTKRYSLKSGTKHEENFSAYPRDSRKRSLLGSIQAFAASVDTLSIQGTSLLTQSPASLSTYND
QSVSFVLENGCYVINVDDSGKDQEQDQVLLRYYESPCPASQSGDGVDGKKLMVNMSPIKDTDIW
LHANDKDYSVELQRGDVSPPEQAFFVLHKKSSDFVSFECKNLPGTYIGVKDNQLALVEEKDESC
NNIMFKLSKI (SEQ ID NO. 6)

IL-33 of SEQ ID NO: 5 is encoded by SEQ ID NO: 7:
ATGAGACCTAGAATGAAGTATTCCAACTCCAAGATTTCCCCGGCAAAGTTCAGCAGCACCGCAG
GCGAAGCCCTGGTCCCGCCTTGCAAAATAAGAAGATCCCAACAGAAGACCAAAGAATTCTGCCA
TGTCTACTGCATGAGACTCCGTTCTGGCCTCACCATAAGAAAGGAGACTAGTTATTTTAGGAAA
GAACCCACGAAAAGATATTCACTAAAATCGGGTACCAAGCATGAAGAGAACTTCTCTGCCTATC
CACGGGATTCTAGGAAGAGATCCTTGCTTGGCAGTATCCAAGCATTTGCTGCGTCTGTTGACAC
ATTGAGCATCCAAGGAACTTCACTTTTAACACAGTCTCCTGCCTCCCTGAGTACATACAATGAC
CAATCTGTTAGTTTTGTTTTGGAGAATGGATGTTATGTGATCAATGTTGACGACTCTGGAAAAG
ACCAAGAGCAAGACCAGGTGCTACTACGCTACTATGAGTCTCCCTGTCCTGCAAGTCAATCAGG
CGACGGTGTGGATGGGAAGAAGCTGATGGTGAACATGAGTCCCATCAAAGACACAGACATCTGG
CTGCATGCCAACGACAAGGACTACTCCGTGGAGCTTCAAAGGGGTGACGTCTCGCCTCCGGAAC
AGGCCTTCTTCGTCCTTCACAAAAAGTCCTCGGACTTTGTTTCATTTGAATGCAAGAATCTTCC
TGGCACTTACATAGGAGTAAAAGATAACCAGCTGGCTCTAGTGGAGGAGAAAGATGAGAGCTGC
AACAATATTATGTTTAAGCTCTCGAAAATCTAA (SEQ ID NO: 7)

IL-33 of SEQ ID NO: 6 is encoded by SEQ ID NO: 8:
ATGAGACCTAGAATGAAGTATTCCAACTCCAAGATTTCCCCGGCAAAGTTCAGCAGCACCGCAG
GCGAAGCCCTGGTCCCGCCTTGCAAAATAAGAAGATCCCAACAGAAGACCAAAGAATTCTGCCA
TGTCTACTGCATGAGACTCCGTTCTGGCCTCACCATAAGAAAGGAGACTAGTTATTTTAGGAAA
GAACCCACGAAAAGATATTCACTAAAATCGGGTACCAAGCATGAAGAGAACTTCTCTGCCTATC
CACGGGATTCTAGGAAGAGATCCTTGCTTGGCAGTATCCAAGCATTTGCTGCGTCTGTTGACAC
ATTGAGCATCCAAGGAACTTCACTTTTAACACAGTCTCCTGCCTCCCTGAGTACATACAATGAC
CAATCTGTTAGTTTTGTTTTGGAGAATGGATGTTATGTGATCAATGTTGACGACTCTGGAAAAG
```

```
ACCAAGAGCAAGACCAGGTGCTACTACGCTACTATGAGTCTCCCTGTCCTGCAAGTCAATCAGG
CGACGGTGTGGATGGGAAGAAGCTGATGGTGAACATGAGTCCCATCAAAGACACAGACATCTGG
CTGCATGCCAACGACAAGGACTACTCCGTGGAGCTTCAAAGGGGTGACGTCTCGCCTCCGGAAC
AGGCCTTCTTCGTCCTTCACAAAAAGTCCTCGGACTTTGTTTCATTTGAATGCAAGAATCTTCC
TGGCACTTACATAGGAGTAAAAGATAACCAGCTGGCTCTAGTGGAGGAGAAAGATGAGAGCTGC
AACAATATTATGTTTAAGCTCTCGAAAATCTAA (SEQ ID NO: 8)

A functional fragment of PIBF1 effective to prevent and/or inhibit
preterm labor in a pregnant subject-SEQ ID NO: 9
MSRKISKESKKVNISSSLESEDISLETTVPTDDISSSEEREGKVRITRQLIERKELLHNIQLLK
IELSQKTMMIDNLKVDYLTKIEELEEKLNDALHQKQLLTLRLDNQLAFQQKDASKYQELMKQEM
ETILLRQKQLEETNLQLREKAGDVRRNLRDFELTEEQYIKLKAFPEDQLSIPEYVSVRFYELVN
PLRKEICELQVKKNILAEELSTNKNQLKQLTETYEEDRKNYSEVQIRCQRLALELADTKQLIQQ
GDYRQENYDKVKSERDALEQEVIELRRKHEILEASHMIQTKERSELSKEVVTLEQTVTLLQKDK
EYLNRQNMELSVRCAHEEDRLERLQAQLEESKKAREEMYEKYVASRDHYKTEYENKLHDELEQI
RLKTNQEIDQLRNASREMYERENRNLREARDNAVA (SEQ ID NO: 9)

PIBF1 functional fragment of SEQ ID NO: 9 is encoded by SEQ ID NO: 10:
atgtctcgaaaaatttcaaaggagtcaaaaaaagtgaacatctctagttctctggaatctgaag
atattagtttagaaacaacagttcctacggatgatatttcctcatcagaagagcgagagggcaa
agtcagaatcaccaggcagctaattgaacgaaaagaactacttcataatattcagttactaaaa
attgagctatcccagaaaactatgatgatcgacaatttgaaagtggattatcttacaaagattg
aagaattggaggagaaacttaatgatgcacttcaccagaagcagctactaacattgagattaga
caaccaattggcttttcaacagaaagatgccagcaaatatcaagaattaatgaaacaagaaatg
gaaaccattttgttgagacagaaacaactagaagagacaaatcttcagctaagagaaaaagctg
gagatgttcgtcgaaacctgcgtgactttgagttgacagaagagcaatatattaaattaaaagc
ttttcctgaagatcagtttctattcctgaatatgtatctgttcgcttctatgagctagtgaat
ccattaagaaaggaaatctgtgaactacaagtgaaaaagaatatcctagcagaagaattaagta
caaacaaaaccaactgaagcagctgacagagacatatgaggaagatcgaaaaaactactctga
agttcaaattagatgtcaacgtttggccttagaattagcagacacaaaacagttaattcagcaa
ggtgactaccgtcaagagaactatgataaagtcaagagtgaacgtgatgcacttgaacaggaag
taattgagcttaggagaaaacatgaaatacttgaagcctctcacatgattcaaacaaaagaacg
aagtgaattatcaaaagaggtagtcaccttagagcaaactgttactttactgcaaaaggataaa
gaatatcttaatcgccaaaacatggagcttagtgttcgctgctcatgaagaggatcgccttg
aaagacttcaagctcaactggaagaaagcaaaaaggctagagaagagatgtatgaaaaatatgt
agcatccagagaccattataaaacagaatgaaaataaactacatgatgaactagaacaaatc
agattgaaaaccaaccaagaaattgatcaacttcgaaatgcctctaggggaaatgtatgaacgag
aaaacagaaatctccgagaagcaagggataatgctgtggct (SEQ ID NO: 10)

Recombinant full-length PIBF1 (fPIBF1) (aa 1-757; with an N-terminal
glutathione-S-transferase (GST) tag of 232 amino acids, Abnova
H00010464-P01-SEQ ID NO: 11)
MSPILGYWKIKGLVQPTRLLLEYLEEKYEEHLYERDEGDKWRNKKFELGLEFPNLPYYIDGDVKL
TQSMAIIRYIADKHNMLGGCPKERAEISMLEGAVLDIRYGVSRIAYSKDFETLKVDFLSKLPEML
KMFEDRLCHKTYLNGDHVTHPDFMLYDALDVVLYMDPMCLDAFPKLVCFKKRIEAIPQIDKYLKS
SKYIAWPLQGWQATFGGGDHPPKSDLVPRGSPGIHRDMSRKISKESKKVNISSSLESEDISLETT
VPTDDISSSEEREGKVRITRQLIERKELLHNIQLLKIELSQKTMMIDNLKVDYLTKIEELEEKLN
DALHQKQLLTLRLDNQLAFQQKDASKYQELMKQEMETILLRQKQLEETNLQLREKAGDVRRNLRD
FELTEEQYIKLKAFPEDQLSIPEYVSVRFYELVNPLRKEICELQVKKNILAEELSTNKNQLKQLT
ETYEEDRKNYSEVQIRCQRLALELADTKQLIQQGDYRQENYDKVKSERDALEQEVIELRRKHEIL
EASHMIQTKERSELSKEVVTLEQTVTLLQKDKEYLNRQNMELSVRCAHEEDRLERLQAQLEESKK
AREEMYEKYVASRDHYKTEYENKLHDELEQIRLKTNQEIDQLRNASREMYERENRNLREARDNAV
AEKERAVMAEKDALEKHDQLLDRYRELQLSTESKVTEFLHQSKLKSFESERVQLLQEETARNLTQ
CQLECEKYQKKLEVLTKEFYSLQASSEKRITELQAQNSEHQARLDIYEKLEKELDEIIMQTAEIE
NEDEAERVLFSYGYGANVPTTAKRRLKQSVHLARRVLQLEKQNSLILKDLEHRKDQVTQLSQELD
RANSLLNQTQQPYRYLIESVRQRDSKIDSLTESIAQLEKDVSNLNKEKSALLQTKNQMALDLEQL
LNHREELAAMKQILVKMHSKHSENSLLLTKTEPKHVTENQKSKTLNVPKEHEDNIFTPKPTLFTK
KEAPEWSKKQKMKT (SEQ ID NO: 11)

Recombinant C-terminal fragment of PIBF1 (cPIBF1) (aa 660-755 with an N-
terminal glutathione-S-transferase (GST) tag of 232 amino acids, Abnova
H00010464-Q01; SEQ ID NO: 12),
MSPILGYWKIKGLVQPTRLLLEYLEEKYEEHLYERDEGDKWRNKKFELGLEFPNLPYYIDGDVKL
TQSMAIIRYIADKHNMLGGCPKERAEISMLEGAVLDIRYGVSRIAYSKDFETLKVDFLSKLPEML
KMFEDRLCHKTYLNGDHVTHPDFMLYDALDVVLYMDPMCLDAFPKLVCFKKRIEAIPQIDKYLKS
SKYIAWPLQGWQATFGGGDHPPKSDLVPRGSPGIHRDEKSALLQTKNQMALDLEQLLNHREELAA
MKQILVKMHSKHSENSLLLTKTEPKHVTENQKSKTLNVPKEHEDNIFTPKPTLFTKKEAPEWSKK
QKM (SEQ ID NO: 12)
```

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A method of preventing and/or inhibiting preterm labor in a pregnant subject, comprising:
administering a therapeutically effective amount of a protein selected from the group consisting of: PIBF1 protein comprising SEQ ID NO:1 or SEQ ID NO:2, a variant thereof that is at least 99% identical to SEQ ID NO: 1, wherein substitution mutations in the variant are conservative substitutions, a variant thereof that is at least 99% identical to SEQ ID NO: 2, wherein substitution mutations in the variant are conservative substitutions, a variant thereof that is encoded by the complement of a nucleic acid that hybridizes under highly stringent conditions with the nucleotide sequence of SEQ ID NO: 3, and a variant thereof that is encoded by the complement of a nucleic acid that hybridizes under highly stringent conditions with the nucleotide sequence of SEQ ID NO: 4, wherein the highly stringent conditions comprise hybridization in 6×SSC, 5×Denhardt's solution, 30% formamide, and 100 microgram/ml denatured salmon sperm at 37° C. overnight followed by washing in a solution of 0.1×SSC and 0.1% SDS at 60° C. for 15 minutes: IL-33, a fragment or variant thereof; and a combination of any two or more thereof, to a pregnant subject in need thereof.

2. The method of claim 1, wherein the IL-33 is a protein comprising the amino acid of SEQ ID NO: 5, a fragment or variant thereof wherein the protein, fragment or variant thereof is effective to prevent and/or inhibit preterm labor in the pregnant subject.

3. The method of claim 1, wherein the IL-33 is a protein comprising the amino acid of SEQ ID NO: 6, a fragment or variant thereof wherein the protein, fragment or variant thereof is effective to prevent and/or inhibit preterm labor in the pregnant subject.

4. The method of claim 1, wherein the IL-33 is a protein encoded by the complement of a nucleic acid that hybridizes under the highly stringent conditions with the nucleotide sequence of SEQ ID NO: 7.

5. The method of claim 1, wherein the IL-33 is a protein encoded by the complement of a nucleic acid that hybridizes under the highly stringent conditions with the nucleotide sequence of SEQ ID NO: 8.

6. The method of claim 1, wherein the IL-33 is a protein comprising an amino acid sequence that is at least 95% identical to SEQ ID NO: 5.

7. The method of claim 1, wherein the IL-33 is a protein comprising an amino acid sequence that is at least 95% identical to SEQ ID NO: 6.

8. The method of claim 1, wherein the subject is human.

9. The method of claim 1, further comprising administering an additional therapeutic agent.

10. The method of claim 9, wherein the additional therapeutic agent is a tocolytic agent.

11. A composition for preventing and/or inhibiting preterm labor in a pregnant subject in need thereof, comprising 1) a protein selected from the group consisting of: PIBF1 protein comprising SEQ ID NO:1 or SEQ ID NO:2, a PIBF1 variant that is at least 99% identical to SEQ ID NO: 1, wherein substitution mutations in the variant are conservative substitutions, a PIBF1 variant that is at least 99% identical to SEQ ID NO: 2, wherein substitution mutations in the variant are conservative substitutions, a PIBF1 variant that is encoded by the complement of a nucleic acid that hybridizes under highly stringent conditions with the nucleotide sequence of SEQ ID NO: 3 or a PIBF1 variant that is encoded by the complement of a nucleic acid that hybridizes under highly stringent conditions with the nucleotide sequence of SEQ ID NO: 4, a combination of any two or more thereof, and a combination of PIBF1 of SEQ ID NO:1 or SEQ ID NO:2, a PIBF1 variant that is at least 99% identical to SEQ ID NO: 1, wherein substitution mutations in the variant are conservative substitutions, a PIBF1 variant that is at least 99% identical to SEQ ID NO: 2, wherein substitution mutations in the variant are conservative substitutions, a PIBF1 variant that is encoded by the complement of a nucleic acid that hybridizes under highly stringent conditions with the nucleotide sequence of SEQ ID NO: 3, a PIBF1 variant that is encoded by the complement of a nucleic acid that hybridizes under highly stringent conditions with the nucleotide sequence of SEQ ID NO: 4, and IL-33 or a variant thereof; and a pharmaceutically acceptable carrier; or 2) an expression vector encoding a protein selected from the group consisting of: PIBF1 of SEQ ID NO:1 or SEQ ID NO:2, a PIBF1 variant that is at least 99% identical to SEQ ID NO: 1, wherein substitution mutations in the variant are conservative substitutions, a PIBF1 variant that is at least 99 identical to SEQ ID NO: 2, wherein substitution mutations in the variant are conservative substitutions a PIBF1 variant that is encoded by the complement of a nucleic acid that hybridizes under highly stringent conditions with the nucleotide sequence of SEQ ID NO: 3, a PIBF1 variant that is encoded by the complement of a nucleic acid that hybridizes under highly stringent conditions with the nucleotide sequence of SEQ ID NO: 4, a combination of any two or more thereof, and a combination of PIBF1 of SEQ ID NO:1 or SEQ ID NO:2, a PIBF1 variant that is at least 99% identical to SEQ ID NO: 1, wherein substitution mutations in the variant are conservative substitutions, a PIBF1 variant that is at least 99% identical to SEQ ID NO: 2, wherein substitution mutations in the variant are conservative substitutions a PIBF1 variant that is encoded by the complement of a nucleic acid that hybridizes under highly stringent conditions with the nucleotide sequence of SEQ ID NO: 3, a PIBF1 variant that is encoded by the complement of a nucleic acid that hybridizes under highly stringent conditions with the nucleotide sequence of SEQ ID NO: 4, and IL-33 or a variant thereof; and a pharmaceutically acceptable carrier, or 3) a combination of both 1) and 2), wherein the highly stringent conditions comprise hybridization in 6×SSC, 5×Denhardt's solution, 30% formamide, and 100 micro-rams/ml denatured salmon sperm at 37° C. overnight followed by washing in a solution of 0.1×SSC and 0.1% SDS at 60° C. for 15 minutes.

12. The composition of claim 11, further comprising an additional therapeutic agent.

* * * * *

UNITED STATES PATENT AND TRADEMARK OFFICE
CERTIFICATE OF CORRECTION

PATENT NO. : 10,391,148 B2
APPLICATION NO. : 15/692517
DATED : August 27, 2019
INVENTOR(S) : Kang Chen It is certified that error appears in the above-identified patent and that said Letters Patent is hereby corrected as shown below:

In the Claims

Column 77, Line 60: Claim 1 Replace "microgram/ml" with --micrograms/ml--;

Column 77, Line 62: Claim 1 Replace "minutes:" with --minutes;--;

Column 80, Line 2: Claim 11 Replace "99" with --99%--;

Column 80, Line 4: Claim 11 After "stitutions" insert --,--; and

Column 80, Line 27: Claim 11 Replace "micro-rams/ml" with "micrograms/ml--.

Signed and Sealed this
Eighth Day of October, 2019

Andrei Iancu
*Director of the United States Patent and Trademark Office*